United States Patent [19]

Jacobs et al.

[11] Patent Number: 5,681,840
[45] Date of Patent: Oct. 28, 1997

[54] TRICYCLIC ANTIPSYCHOTIC COMPOUNDS

[75] Inventors: Robert Toms Jacobs, Wilmington, Del.; Michael Thaddeus Klimas, Exton, Pa.; Cyrus John Ohnmacht; Marc Ornal Terpko, both of Wilmington, Del.

[73] Assignee: Zeneca Limited, London, England

[21] Appl. No.: 584,634

[22] Filed: Jan. 11, 1996

Related U.S. Application Data

[63] Continuation of Ser. No. 139,239, Oct. 19, 1993, Pat. No. 5,512,575, which is a continuation-in-part of Ser. No. 927,023, Aug. 6, 1992, abandoned.

[30] Foreign Application Priority Data

Aug. 15, 1991 [GB] United Kingdom ............. 9117639
Jul. 9, 1993 [GB] United Kingdom ............. 9314250

[51] Int. Cl.$^6$ .................. A61K 31/445; C07D 217/00
[52] U.S. Cl. ............................................ 514/325; 546/203
[58] Field of Search ............................ 514/325; 546/203

[56] References Cited

U.S. PATENT DOCUMENTS

| | | | |
|---|---|---|---|
| 3,399,201 | 8/1968 | Schmidt et al. | 544/380 |
| 3,422,106 | 1/1969 | Boissier et al. | 544/271 |
| 3,455,928 | 7/1969 | Schmidt et al. | 544/380 |
| 3,489,799 | 1/1970 | Schmidt et al. | 564/219 |
| 3,632,653 | 1/1972 | Schmidt et al. | 568/439 |
| 3,706,765 | 12/1972 | Wilhelm et al. | 564/378 |
| 3,778,467 | 12/1973 | Wilhelm et al. | 560/250 |
| 3,870,796 | 3/1975 | Hunger et al. | 514/655 |
| 4,017,542 | 4/1977 | Wilhelm et al. | 564/355 |
| 4,045,560 | 8/1977 | Sunagawa et al. | 514/239.5 |
| 4,045,580 | 8/1977 | Wilhelm et al. | 514/653 |
| 4,153,629 | 5/1979 | Tanida et al. | 514/644 |
| 4,216,231 | 8/1980 | Tanida et al. | 514/644 |
| 4,224,344 | 9/1980 | Sunagawa et al. | 514/649 |
| 4,318,926 | 3/1982 | Schimdt-Ruppin et al. | 514/654 |
| 4,358,620 | 11/1982 | Sunagawa et al. | 568/439 |

FOREIGN PATENT DOCUMENTS

| | | |
|---|---|---|
| 610863 | 10/1961 | Belgium . |
| 843875 | 7/1975 | Belgium . |
| 918677 | 1/1973 | Canada . |
| 2556-143 | 12/1974 | Germany . |
| 2068-170 | 12/1975 | Japan . |
| 2122-358 | 4/1976 | Japan . |
| 3005-176 | 5/1976 | Japan . |
| 52-007953 | 1/1977 | Japan . |
| 6907455 | 5/1965 | Netherlands . |
| 533079 | 3/1973 | Switzerland . |

OTHER PUBLICATIONS

Klimas et al. "Putative atypical antipsychotics with mixed dopaminergic . . ." CA 123:246036 1995.
Sunagawa et al., "Dibenzotetracyclic Derivatives II. Synthesis of 9-Aminoalkyl-9,10-dihydro-9,10-methanoanthracenes" *Chem. Pharm. Bull.* (1979), 27, 1806–1812.
Pitchet et al., "An Efficient Asymmetric Oxidation of Sulfides to Sulfoxides:" *J. Am. Chem. Soc.* (1984), 8188–8193.
Davis et al., "Chemistry of Oxaziridines. 3.$^1$ Asymmetric Oxidation of Organosulfur Compounds Using Chiral 2-Sulfonyloxaziridines" *J. Am. Chem. Soc.* (1982), 104, 5412.

*Primary Examiner*—Ceila Chang
*Attorney, Agent, or Firm*—Michael D. Alexander

[57] ABSTRACT

Compounds of formula I or I',

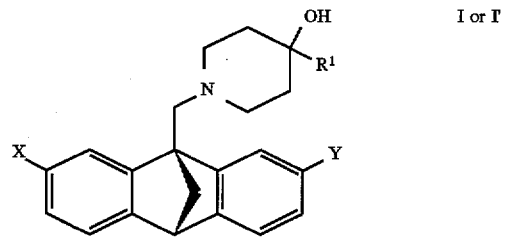

wherein
X and Y are independently selected from hydrogen, halo, and (1–6C)alkoxy;
R$^1$ is selected from
(A) (1–6C)alkyl;
(B) phenyl and naphthyl or substituted versions thereof;
(C) phenyl(1–3C)alkyl and naphthyl(1–3C)alkyl;
(D) five- and six-membered heteroaryl rings;
(E) heteroaryl(1–3C)alkyl and pharmaceutically acceptable salts thereof, useful in the treatment of neuropsychiatric disorders such as psychoses; pharmaceutical compositions comprising a compound of formula I or I' and a pharmaceutically acceptable diluent or carrier; and methods of treating neuropsychiatric disorders comprising administering to a mammal (including man) in need of such treatment an effective amount of a compound of formula I or I', or a pharmaceutically acceptable salt thereof are claimed. The invention also relates to novel processes for producing enantiomeric methanoanthracenyl sulfoxides.

13 Claims, No Drawings

TRICYCLIC ANTIPSYCHOTIC COMPOUNDS

This application is a continuation of prior application Ser. No. 08/139,239, filed Oct. 19, 1993, now U.S. Pat. No. 5,512,575 which in turn is a continuation-in-part of U.S. Ser. No. 07/927,023 filed on Aug. 6, 1992 now abandoned. This invention relates to methanoanthracene compounds useful because they have been determined to be antagonists of dopamine at $D_2$ receptors. The compounds exhibit antidopaminergic activity and are useful in alleviating neuropsychiatric disorders such as psychoses, as antipsychotics, and as neuroleptics. In addition, as $D_2$ antagonists, compounds according to the invention may also be useful in the amelioration of other disorders in which dopaminergic activity has been implicated, for example gastrointestinal disorders, emesis, and tardive dyskinesia.

The present invention further relates to novel piperidinyl compounds which contain a chiral sulfoxide moiety and processes related to their synthesis and production. The compounds and the pharmaceutical compositions containing the active ingredient are useful as dopamine antagonists and are particularly useful as antipsychotic agents in humans. The compounds may also be useful in other neurological and psychiatric disorders including schizophrenia. The present invention relates to methanoanthracenyl compounds that are essentially or substantially pure chiral sulfoxide enantiomers or diastereomers and pharmaceutical compositions containing said active ingredients wherein the compounds are useful as D1 and D2 dopamine antagonists as well as 5HT2 serotonin antagonists. The claimed enantiomeric or diastereomeric compounds have an improved, balanced and more favorable D1/D2 dopamine antagonist ratio which may be predictive of an improved clinical profile in humans. The present compounds are also serotonin 5HT2 antagonists. The present invention also relates to novel syntheses of chiral methanoanthracenyl sulfoxides wherein the process utilizes several oxidation methods to selectively oxidize a methanoanthracenyl sulfide to an enantiomerically enriched sulfoxide mixture which can be further purified to a pure or substantially pure methanoanthrancenyl sulfoxide. In addition, the present invention relates to a process for recycling racemic materials or those enriched in the undesired methanoanthrancenyl sulfoxide enantiomer which may be readily coupled with the enantioselective oxidation to produce pure enantiomeric material.

According to the invention there is provided a compound of formula I (formula set out, together with other formulae referred to by Roman Numerals, on pages following the Examples), or a pharmaceutically acceptable salt thereof, wherein X and Y are independently selected from hydrogen, halo, and (1–6C)alkoxy;

$R^1$ is selected from (A) (1–6C)alkyl;

(B) phenyl and naphthyl each of which may bear 0–3 substituents independently selected from the group consisting of
(1–6C)alkyl, (1–6C)alkoxy, hydroxy, halo, cyano, nitro, phenyl, benzyloxy, benzoyl, trifluoromethyl;
aminosulfonyl having the formula $SO_2NR^aR^b$, and aminocarbonyl having the formula $CONR^cR^d$ wherein $R^a$, $R^b$, $R^c$ and $R^d$ are independently selected from hydrogen, 2-pyrrolidinyl, and (1–6C)alkyl, or wherein $R^a$ and $R^b$, and $R^c$ and $R^d$, together with the nitrogen atom to which each is attached, form a 5-membered or 6-membered heterocyclic ring in which the said nitrogen is the only heteroatom; and
$R^hR^iN$(1–3C)alkyl wherein $R^h$ and $R^i$ are independently selected from hydrogen and (1–3C)alkyl;

(C) phenyl(1–3C)alkyl and naphthyl(1–3C)alkyl wherein the phenyl and naphthyl moieties may bear 0–3 substituents selected from the values of phenyl and naphthyl substituents given in (B).

(D) five- and six-membered heteroaryl rings containing from 1–3 heteroatoms selected from nitrogen, oxygen, and sulfur, and benz derivatives thereof, which may bear 0–2 substitutents selected from (1–6C)alkyl, hydroxy, (1–6C)alkoxy which may bear a trifluoromethyl group, (1–6C)alkoxycarbonyl, (1–6C)hydroxyalkyl, benzyloxy, halo, (1–3C)alkylaminocarbonyl(1–3C)alkyl, aminocarbonyl as defined in (B), $R^eS(O)_n$, $R^fNH$, and $R^gS$ wherein $R^e$ and $R^f$ are independently selected from hydrogen and (1–6C)alkyl and n is 0, 1 or 2, and $R^g$ is selected from (1–3C)alkylcarbonylaminophenyl and di(1–3C)alkylamino(1–6C)alkyl; and (E) heteroaryl(1–3C)alkyl wherein the heteroaryl moiety is a five- or six-membered ring as defined in (D) and wherein the heteroaryl moiety may bear 0–2 substituents selected from the values of heteroaryl substituents given in (D).

The invention further provides a pharmaceutical composition comprising a compound of formula I as defined above, or a pharmaceutically acceptable salt thereof, and a pharmaceutically acceptable diluent or carrier.

The invention further provides a method for the treatment of neuropsychiatric disorders, comprising administering to a mammal (including man) in need of such treatment an effective amount of a compound of formula I as defined above, or a pharmaceutically acceptable salt thereof.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo" is inclusive of fluoro, chloro, bromo, and iodo unless noted otherwise.

It will be appreciated by those skilled in the art that compounds of formula I may contain an asymmetrically substituted carbon and/or sulfur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of psychoses, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of psychoses by the standard tests described hereinafter.

Particular values of (1–6C)alkyl include methyl, ethyl, propyl, isopropyl, butyl, isobutyl, sec-butyl, tert-butyl, pentyl, isopentyl, neopentyl, hexyl, and isohexyl.

Particular values of (1–3C)alkyl include methyl, ethyl, and propyl.

Particular values of (1–6C)alkoxy include methoxy, ethoxy, propoxy, isopropoxy, butoxy, isobutoxy, sec-butoxy, tert-butoxy, pentoxy, isopentoxy, neopentoxy, hexoxy, and isohexoxy.

Particular values of (1–3C)alkoxy include methoxy, ethoxy, and propoxy.

Particular values of five- and six-membered heteroaryl rings containing from 1–3 heteroatoms selected from nitrogen, oxygen, and sulfur include 2,3-, and 4-pyridyl, 2-pyrazinyl, 2- and 4-pyrimidinyl, 3- and 4-pyridazinyl, 3-, 4- and 5-isothiazolyl, 2-, 4- and 5-oxazolyl, 2-, 4- and 5-thiazolyl, 4- and 5-oxadiazolyl, 2- and 3-furyl, 2-, 4-, and 5-imidazolyl, and 2- and 3-thienyl. The preceding rings can optionally bear the substituents previously noted.

Particular values of benz derivatives of five- and six-membered heteroaryl groups include the various quinolinyl, isoquinolyl, and benzothiazolyl groups, which may be substituted as previously defined.

Particular values of (1–6C)hydroxyalkyl include hydroxymethyl, 1-hydroxyethyl, 2-hydroxyethyl, 1-hydroxypropyl, 2-hydroxypropyl, 3-hydroxypropyl, 1-hydroxyprop-2-yl, 1-hydroxybutyl, 2-hydroxybutyl, and 3-hydroxybutyl.

More particular values of X and Y include hydrogen and halo.

More particular values of (1–6C)alkyl include values of (1–3C)alkyl, including methyl, ethyl, propyl, isopropyl, and tert-butyl.

More particular values of (1–6C)alkoxy include values of (1–3C)alkoxy, including methoxy, ethoxy, propoxy, and isopropoxy.

More particular values of five- and six-membered heteroaryl rings containing from 1–3 heteroatoms selected from nitrogen, oxygen, and sulfur include 2, 3-, and 4-pyridyl, 3-, 4- and 5-isothiazolyl, 2-, 4- and 5-thiazolyl, and 2- and 4-imidazolyl, which rings may be optionally substituted as previously defined.

More particular values of benz derivatives of five- and six-membered heteroaryl groups include 3-quinolyl, 4-isoquinolinyl, 2-methoxy-3-quinolyl, 2-benzothiazolyl, 6-methoxy-2-benzothiazolyl, and 2-benzthienyl.

More particular values of (1–6C)hydroxyalkyl include values of (1–3C)hydroxyalkyl, including hydroxymethyl, 1-hydroxyethyl, 2-hydroxyethyl, 1-hydroxypropyl, 2-hydroxypropyl, and 3-hydroxypropyl.

Preferred values of X and Y include hydrogen and chloro.

A preferred value of $R^1$ as (1–6C)alkyl is tert-butyl (also referred to herein as a 1,1-dimethylethyl group).

Preferred values of $R^1$ as phenyl and naphthyl substituted with 0–3 substituents include 2- and 3-methoxyphenyl, and phenyl substituted at the 2- or 3-position with aminosulfonyl of formula $R^a R^b NSO_2$ wherein $R^a$ and $R^b$ are independently selected from hydrogen, methyl and ethyl.

Preferred values of $R^1$ as a five-membered heteroaryl ring substituted with 0–2 substituents include thienyl and furyl.

Preferred values of $R^1$ as a six-membered heteroaryl ring substituted with 0–2 substituents include 3-pyridyl, either unsubstituted or substituted at the 2-position with (1–6C)alkylthio, (1–6C)alkylsulfinyl, or (1–6C)alkoxy.

A preferred compound has formula I wherein:

X and Y are independently selected from hydrogen and chloro;

$R^1$ is selected from the group consisting of:
  (i) tert-butyl;
  (ii) 2- and 3-methoxyphenyl, and phenyl substituted at the 2- or 3-position with aminosulfonyl of formula $R^a R^b NSO_2$ wherin $R^a$ and $R^b$ are independently selected from hydrogen, methyl and ethyl;
  (iii) thienyl, furyl, and 3-pyridyl optionally substituted at the 2-position by (1–6C)alkoxy, (1–6C)alkylthio, or (1–6C)alkylsulfinyl.

Specifically preferred compounds include:

1-((9S,10S)-2-Chloro-9,10-dihydro-9,10-methanoanthracen-9-yl-methyl)-4-(1,1-dimethylethyl) piperidin-4-ol;

1-(9,10-Dihydro-9,10-methanoanthracen-9-ylmethyl)-4-(2-ethylsulfinyl-3-pyridyl)piperidin-4-ol;

1-(9,10-Dihydro-9,10-methanoanthracen-9-ylmethyl)-4-(2-ethylthio-3-pyridyl)piperidin-4-ol; and 1-(2-Chloro-9,10-dihydro-9,10-methanoanthracen-9-ylmethyl)-4-(2-methoxy-3-pyridyl)piperidin-4-ol.

When X is chloro and Y is hydrogen, in general, 9S,10S stereochemistry is preferred. In this case, stereochemistry can be determined by coupling an acid chloride of formula III (G=chloro) with a chiral compound, such as an oxazolidinone of formula IV, to yield two diastereomers. Separation and recrystallization of the diastereomers followed by X-ray structure determination provides absolute stereochemistry at the 9 and 10 positions.

A compound of formula I can be made by processes which include processes known in the chemical arts for the production of structurally analogous compounds. Such processes for the manufacture of an amide of formula I as defined above are provided as further features of the invention together with chemical intermediates involved therein, and are illustrated by the following procedures in which the meanings of generic radicals are as given above unless otherwise qualified. Such a process can be effected, generally, (a) by treating a piperidone having formula II with a corresponding compound of formula $R^1 Li$ in an aprotic solvent such as THF. The lithium compound can be conveniently generated in situ by reacting a compound of formula $R^1 Z$, wherein Z is a halo group or, in some cases hydrogen, with a (1–6C)alkyllithium compound, for example n-butyllithium, generally in a temperature in the range of –20° to –100° C.

(b) by treating a corresponding amide of formula IIa with a suitable reducing agent, for example lithium aluminum hydride or borane dimethylsulfide complex;

(c) by treating an aldehyde of formula III (G is hydrogen) with a corresponding piperidine of formula IV in the presence of a reducing agent, for example such as sodium cyanoborohydride;

(d) for a compound of formula I wherein a value of (1–6C)alkoxy for either of X and Y is desired, by treating a corresponding compound of formula I wherein the value for X or Y is hydroxy, with a corresponding (1–6C)alkyl halide in the presence of a base (such as an alkali metal hydride). The reaction can be conducted at a temperature of 0° C. to room temperature and in an appropriate solvent such as THF. A sequence of reactions for generating a hydroxy precursor is exemplified by Examples 89–91.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples. It is noted that compounds having the formula $R^1 Z$ can be made by techniques analogous to or as reported in Brandsma et. al., *Preparative Polar Organometallic Chemistry I*, Springer-Verlag, 1$^{st}$ edition, 1987. In the discussion which follows and the reaction Schemes pertaining thereto, standard chemical abbreviations and acronyms have been employed, including: "Et" for ethyl; "THF" for tetrahydrofuran; "Bu" for tert-butyl; "RT" for room temperature; "DMSO" for dimethylsulfoxide; "Me" for methyl; "Cbz" for carbobenzyloxy; and "Ph" for phenyl. "Z" means a halo group such as chloro when referring to Grignard agents or alkyllithium compounds.

A common intermediate for making compounds according to the invention is an acid (G is hydroxyl) or acid halide (G is a halo group such as chloro) of formula III. This intermediate can be made as illustrated in Scheme I (set out, together with other schemes referred to herein, on pages following the Examples and formulae). An anthraquinone of formula 10 can be reduced to the corresponding anthracene of formula 12 using zinc and aqueous ammonia. Anthracene 12 can then be converted to the corresponding 9-aldehyde 14 using phosphorus oxytrichloride and N-methylformanilide. Reaction of aldehyde 14 with vinyl acetate (Diels-Alder reaction) affords the bridged compound 16 which can then be oxidized with chromium trioxide (in the presence of sulfuric acid) to the corresponding acid 18. Acid 18 can then be successively treated with thionyl chloride (in, for example, toluene) to make the corresponding 9-acid chloride, followed by sodium azide (in, for example, a mixture of water and acetone) to make the corresponding 9-acyl azide, followed by heating (in, for example, toluene) to effect rearrangement to the corresponding isocyanate, followed by treatment with an alkali metal hydroxide (in an alcohol such as ethanol) to cleave the acetyl group to hydroxy and hydrolyze the isocyanate to amino, thereby yielding the 9-amine 20. Amine 20 can then be treated with an alkali metal (for example, sodium) nitrite (in, for example, acetic acid) to effect a ring contraction and thereby yield the 9-aldehyde of formula 22. Aldehyde 22 can be oxidized with chromium trioxide in the presence of sulfuric acid to yield the corresponding 9-acid of formula 24 (corresponding to the acid of formula III, G=hydroxyl). The corresponding 9-acid chloride can be obtained by treating acid 24 with thionyl chloride or oxalyl chloride.

It is noted that if a 2,7-dihalo substituted methanoanthracene is desired, it can be prepared, as illustrated in the examples herein, starting with an (unresolved) acid 24 which is mono-substituted at the 2-position with a desired halo (e.g., chloro) substituent, although in the discussion which follows it is to be understood that an optically enriched isomer (such as 26) can be employed if a corresponding optically enriched dihalo substituted product is desired. Acid 24 can be reacted with thionyl chloride to make the corresponding 9-acid chloride followed by the addition of a lower alcohol (such as methanol or ethanol) to afford a lower 9-alkyl ester. The 2-halo ester can then be nitrated at the 7-position by reaction with a suitable nitrating agent such as a combination of trifluoroacetic anhydride and ammonium nitrate under an inert gas (e.g., nitrogen) atmosphere. This reaction will generally produce a mixture of 2-halo-6-nitro and 2-halo-7-nitro positional isomers which can be separated by conventional separation techniques such as recrystallization or flash chromatography over silica gel. The 2-halo-7-nitro isomer can be reduced to the corresponding 7-amino-2-halo compound by a suitable reducing agent such as stannous chloride, and the 7-amino-2-halide thus obtained can be converted to the corresponding 2,7-dihalo alkyl ester by reaction with a diazotizing agent such as tert-butyl nitrite followed by treatment with a cuptic halide such as cuptic chloride or cuptic bromide. The ester can then be cleaved with a suitable base (such as an alkali metal hydroxide) to afford the corresponding 2,7-dihalo substituted acid.

It is further noted that if an oxygenated substituted methanoanthracene (for example a 2-chloro-7-methoxy derivative) is desired, it can be prepared as illustrated in the examples herein, starting with a 7-amino-2-halo derivative as described above. The amine is treated with a diazotizing agent such as tert-butyl nitrite followed by treatment with the salt of a suitable acid such as trifluoroacetic acid (the salt for example being formed with potassium carbonate in trifluoroacetic acid as the solvent). The resulting trifluoroacetate can be hydrolyzed by conventional means and (1–6C)alkyl groups attached to the oxygen by treatment with base in the presence of a corresponding (1–6C)alkyl halide (such as methyl iodide).

As indicated by the R,S notation in Scheme I, acid 24 is racemic. Resolution of racemic acid 24 can be accomplished by fractional crystallization of diastereomeric salts, formed by addition of a chiral amine such as (+)-pseudoephedrine, from a suitable solvent such as ethanol to yield optically enriched acid 26. Treatment of 26 with thionyl chloride yields a correspondingly optically enriched acid chloride. Optically enriched intermediates can be employed in chiral syntheses to make optically enriched compounds according to the invention.

An amide of formula IIa can be made by treating an acid chloride of formula III (G is chloro) with a piperidine of formula IV in the presence of a base such as a trialkylamine, for example triethylamine.

A piperidone of formula II can be made, as illustrated in Scheme II, by oxidizing a corresponding hydroxypiperidine of formula 32 using an appropriate oxidizing agent such as (1) chromium trioxide in the presence of sulfuric acid and using a suitable solvent such as acetone; (2) sulfur trioxide-pyridine complex in the presence of a base such as a trialkylamine (triethylamine being shown for purposes of illustration) and using a suitable solvent such as a combination of methylene chloride and DMSO; or (3) a combination of oxalyl chloride and DMSO followed by treatment with a base such as a trialkylamine and using a solvent such as methylene chloride.

A hydroxypiperidine of formula 32 can be made by either of the routes also illustrated in Scheme II. 9-Aldehyde 22 can be treated directly with 4-hydroxypiperidine followed by reduction (in the presence of a drying agent such as a molecular sieve) with sodium cyanoborohydride in a suitable solvent such as methanol to make hydroxypiperidine 32.

Alternatively, 9-aldehyde 22 can first be oxidized and converted to the corresponding 9-acid chloride as previously described, followed by treatment with 4-hydroxypiperidine, either in excess or with added base such as a trialkylamine (for example, triethylamine) to yield the corresponding amide 30. Reduction of amide 30 with lithium aluminum hydride in diethyl ether or tetrahydrofuran can then be conducted to afford hydroxypiperidine 32.

Piperidines having formula IV can be synthesized as illustrated in Scheme III. 4-hydroxypiperidine 50 can be reacted with carbobenzyloxy chloride (Cbz-Cl) in the presence of a base such as $Et_3N$ to protect the piperidino nitrogen and thereby yield the corresponding 1-(carbobenzyloxy)piperidine-4-ol 52. Oxidation of piperidine-4-ol 52 with oxalyl chloride and DMSO followed by treatment with a base ($Et_3N$) and in a solvent such as methylene chloride yields the corresponding protected 4-piperidone 54. Piperidone 54 can be treated with an organolithium compound $R^1Li$ or a Grignard agent $R^1MgZ$, at a temperature of $-20°$ to $-70°$ C. and in a solvent such as THF or $Et_2O$ to yield the corresponding protected hydroxypiperidine 56. Protected hydroxypiperidine 56 can be deprotected by treatment with a palladium-on-carbon catalyst (for example 10% Pd/C) and cyclohexene in a solvent such as ethanol, thereby yielding the desired hydroxypiperidine of formula IV.

It is noted that many of the starting materials for synthetic methods as described above are commercially available and/or widely reported in the scientific literature.

Examples of suitable pharmaceutically acceptable salts are organic acid addition salts formed with acids which form a physiologically acceptable anion, for example, tosylate, methanesulfonate, acetate, tartrate, citrate, succinate, benzoate, ascorbate, α-ketoglutarate, and α-glycerophosphate. Suitable inorganic salts may also be formed such as sulfate, nitrate, and hydrochloride. Pharmaceutically acceptable salts may be obtained using standard procedures well known in the art, for example by reacting a compound of formula I with a suitable acid affording a physiologically acceptable anion.

When used to treat psychoses, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous, intravesicular, subcutaneous or intramuscular injection or infusion; or in the form of a patch for transdermal administration. Oral administration is preferred.

The dose of compound of formula I which is administered will necessarily be varied according to principles well known in the art taking account of the route of administration, the severity of the psychotic condition, and the size and age of the patient. In general, a compound of formula I will be administered to a warm blooded animal (such as man) so that an effective dose is received, generally a daily dose in the range of about 0.01 to about 40 mg/kg body weight. For example, if the compound is administered intramuscularly, it is administered in the range of about 0.01 to about 10 mg/kg body weight. If it is administered orally, it is administered in the range of about 0.1 to about 40 mg/kg body weight.

It will be apparent to those skilled in the art that a compound of formula I can be co-administered with other therapeutic or prophylactic agents and/or medicaments that are not medically incompatible therewith. In general, compounds within the scope of the invention do not show any indication of overt toxicity in laboratory test animals at several multiples of the minimum effective dose.

The compounds of Formula I are antagonists of dopamine D-2 receptors, and as such are predicted to be useful as antipsychotic drugs. D-2 antagonism can be shown by standard tests such as antagonism of [$^3$H]-spiperone binding (Test A), and/or antagonism of apomorphine-induced climbing and apomorphine-induced disruption of swimming (Test B).

Test A

The receptor binding assay used to measure affinities of various compounds for the dopamine (DA) D-2 receptor subtype was that described by Saller and Salama in J Pharmacol Exp Ther 236, page 714, 1986.

Specifically, rat striatal membranes were used. Tissue membranes were prepared and washed once in 50 volumes of the appropriate Tris HCl buffer. For the D-2 receptor binding assay, striatal membranes were suspended to a final concentration of 8 mg/ml in 50 mM Tris HCl with 40 nM ketanserin, pH 7.7. Nonspecific binding to D-2 receptors was measured in the presence of 1.0 μM (+)-butaclamol. $IC_{50}$s (drug concentration which produced a 50% displacement) for the displacement of 0.5 nM [$^3$H] spiperone were determined using at least five concentrations of each drug in triplicate. One-half milliliter of membrane suspension was incubated with the compound of interest or vehicle or nonspecific drug, ligand and appropriate Tris HCl buffer. The final reaction volume totaled 1 ml for each tube and was incubated at 37° C. for 15 min to facilitate binding and ensure equilibrium had been met. A Brandel filtering system equipped with GF/B filters was used to separate bound from free drug. The amount of drug bound to the membranes was assessed using liquid scintillation counting techniques. $IC_{50}$ values were obtained from a least squares regression of a logit-log transformation of the data. Typical $IC_{50}$ results in this test were 3nM (nanomolar) for the compound of Example 49 and 12 nM for the compound of Example 5.

Test B

Female Swiss-Webster mice weighing approximately 20 g were deprived of food for approximately 24 h and then dosed orally with various doses of either the vehicle or test agent over a range of doses (N=20 mice per treatment group). Thirty minutes later they were dosed with apomorphine HCl at 1.25 mg/kg, sc, and placed into climbing cages. The climbing cages were 9 cm wide, 15 cm deep and 30 cm high. One wall had 27 horizontal rungs spaced 1 cm apart. Thirteen minutes after apomorphine each mouse was observed continuously for 1 min and the highest and lowest rung reached by its front paws was recorded. The mean of these two scores was used as the score for that mouse. (The highest and lowest scores were 27 and 0, respectively.) Immediately after the 1-min climbing observation period each mouse was placed into a circular swimming tank for 2 min and the number of swims was counted. The height of the tank was 15 cm and the diameter was 28 cm. A circular obstacle measuring 10.5 cm in diameter and having a height of 17 cm was placed into the center of the tank, creating a circular swimming channel 8.75 cm wide. The water level was 5.5 cm and the water was kept at room temperature. Marks were placed on the floor and side of the tank 180 degrees apart. A "swim" was scored each time a mouse swam from one mark to the other. The mice were observed through overhead mirrors and the number of 180 degree swims was recorded for each mouse. Activity in this test was indicated by a decrease in the climbing score accompanied by an increase in the swimming score at a given dose of the test compound. Typical results in this test for minimum effective dose values were 1.3 mg/kg for the compound of Example 49 and 20 mg/kg for the compound of Example 5.

The present invention also relates to novel methanoanthracenyl piperidinyl sulfoxide compounds and their pharmaceutically acceptable salts of the formula as described and set out on the first page following the Examples section wherein the various groups on the formula I' (X, Y and R1) are defined as follows:

X and Y are independently selected from hydrogen, halogen and C1–6 alkoxy;

R1 is selected from:

Five- and six-membered heteroaryl rings containing from 1–3 heteroatoms selected from nitrogen, oxygen, and sulfur, and benz derivatives thereof, which may bear 1–2 substituents selected from C1–6 alkyl, hydroxy, C1–6 alkoxy which may bear a trifloromethyl group, C1–6 alkoxycarbonyl, C1–6 hydroxyalkyl, benzyloxy, halo, C1–3 alkylaminocarbonylC1–3alkyl, aminocarbonyl having the formula: $CONR^cR^d$ wherein $R^c$ and $R^d$ are independently selected from hydrogen, 2-pyrrolidinyl, and $C_{1-6}$ alkyl or wherein $R^c$ and $R^d$ together with the nitrogen atom to which each is attached form a 5- or 6-membered heterocyclic ring in which said nitrogen is the only heteroatom, $R^eS(O)_n$, $R^fNH$, and $R^gS$ wherein $R^e$ and $R^f$ are independently selected from hydrogen and $C_{1-6}$ alkyl and n is 0, 1 or 2 and $R^g$ is selected from $C_{1-3}$ alkylcarbonylaminophenyl and di$(C_{1-3})$alkylamino$(C_{1-6})$ alkyl wherein at least one of the substituents on the five- and/or six-membered heteroaryl ring is a chiral sulfoxide of the formula $C_{1-4}$alkylSO.

The invention further provides a pharmaceutical composition comprising a compound of formula I' as defined above and shown on the pages following the examples and to pharmaceutically acceptable salts thereof and a pharmaceutically acceptable diluent or excipient. The claimed composition may be administered to a patient in need of treatment thereof in a suitable dosage form via an effective delivery system to provide D1 and D2 dopaminergic antagonist activity and to relieve or treat or prevent neurological and psychiatric disorders wherein antipsychotics are a prescribed treatment.

The invention further provides a method of treating neurological disorders comprising administering to a patient in need of treatment thereof a pharmaceutically effective amount of a compound according to formula I' or a pharmaceutically acceptable salt thereof. The invention also relates to a method of treating psychosis comprising administering a pharmaceutically effective amount of a pharmaceutical composition containing an active ingredient as described in formula I' and a pharmaceutically acceptable carrier or diluent. The invention further relates to a method of antagonizing a D1 and D2 dopamine receptor in humans comprising administering an antipsychotic amount of the compound according to formula I' or a pharmaceutical composition containing the compound of formula I' as the active ingredient.

In this specification with respect to Formula I' or species dependent thereon, the terms "alkyl" and "alkoxy" include both straight and branched chain radicals, but it is understood that references to individual radicals such as "propyl" or "propoxy" embrace the straight chain radical and branched chains such as "isopropyl" or "isopropoxy" are referred to specifically.

The term "halo" is inclusive of fluoro, chloro, bromo, and iodo unless otherwise specified. The term "hydroxy" is given its ordinary meaning and may be included as a substituent as further shown herein. Particular values of $C_{1-6}$ alkyl include methyl, ethyl, propyl, isopropyl, butyl, sec-butyl, tert-butyl, pentyl, isopentyl, neopentyl, and isohexyl. Particular values of $C_{1-3}$ alkyl include methyl, ethyl, and propyl. Particular values of $C_{1-6}$ alkoxy include methoxy, ethoxy, propoxy, isopropoxy, butoxy, isobutoxy, sec-butoxy, tert-butoxy, pentoxy, isopentoxy, neopentoxy, hexoxy, and isohexoxy. Particular values of $C_{1-3}$ alkoxy include methoxy, ethoxy, and propoxy.

Particular values of five- and six-membered heteroaryl rings containing from 1–3 heteroatoms selected from nitrogen, oxygen, and sulfur include 2, 3- and 4-pyridyl, 2-pyrazinyl, 2- and 4-pyrimidinyl, 3- and 4-pyridazinyl, 3-, 4- and 5-isothiazoyl, 2-, 4- and 5-oxazolyl, 2-, 4- and 5-thiazolyl, 4- and 5-oxadiazoyl, 2- and 3-furyl, 2-, 4- and 5-imidazolyl, and 2- and 3-thienyl. The preceding rings can optionally bear the substituents listed above in the preceding paragraphs. Particular values of benz derivatives of five- and six-membered heteroaryl groups include the various quinolinyl, isoquinolyl, and benzothiazolyl groups which may also be substituted with halo or $C_{1-6}$ alkyl or alkoxy groups as shown above.

Particular values of $C_{1-6}$ hydroxyalkyl include hydroxymethyl, 1-hydroxyethyl, 2-hydroxyethyl, 1–3 hydroxypropyl, 1-hydroxyprop-2-yl, and 1–3 hydroxybutyl.

More particular values of X and Y include hydrogen and halo. More particular values of $C_{1-6}$ alkyl include $C_{1-4}$ alkyl, including methyl, ethyl, propyl, isopropyl, butyl, tert-butyl and isobutyl. More particular values of $C_{1-6}$ alkyloxy (alkoxy) include values of $C_{1-4}$ alkoxy, including methoxy, ethoxy, propoxy, isopropoxy, butoxy, isobutoxy and tert-butoxy. More particular values of five- and six-membered heteroaryl rings containing from 1–3 heteroatoms selected from nitrogen, oxygen and sulfur include 2, 3-, and 4-pyridyl, 3-, 4- and 5-isothiazoyl, 2-, 4- and 5-thiazoyl, and 2- and 4-imidazoyl wherein the rings may optionally be substituted with the substituents as defined above. More particular values of benz derivatives of five- and six-membered heteroaryl groups include 3-quinolyl, 4-isoquinolinyl, 2-methoxy-3-quinolyl, 2-benzothiazoyl, and 2-benzthienyl. More particular values of $C_{1-6}$ hydroxyalkyl include values of $C_{1-3}$ hydroxyalkyl such as hydroxymethyl, 1 or 2 hydroxyethyl, 1–3 hydroxypropyl.

The preferred values for X and Y as defined herein with respect to formula I' are hydrogen and chloro with hydrogen being most preferred. The preferred value of $R^1$ is as a six-membered heteroaryl ring substituted with 1–2 substituents and particularly includes 3-pyridyl substituted at the 2-position with $C_{1-4}$ alkylsulfinyl wherein the $C_{1-4}$ alkylsulfinyl lends chirality to the preferred compounds described herein.

A preferred compound may be selected from formula I' as shown following the examples wherein:

X and Y are hydrogen;

$R^1$ is 3-pyridyl substituted at the 2-position with $C_{1-4}$ alkylsulfinyl. A specifically preferred compound is (−)-1-(9,10-Dihydro-9,10-methanoanthracen-9-ylmethyl)-4-(2-ethylsulfinyl-3-pyridyl)piperidin-4-ol. The present invention also includes enantiomeric mixtures of the above preferred compound wherein the (−) enantiomer is present in excess over the (+) enantiomer.

When X is chloro and Y is hydrogen, in general, 9S,10S stereochemistry may be preferred. The stereochemistry can be determined by standard methods such as coupling an acid chloride at the 9-position of the methanoanthracene ring with a chiral resolving reagent to produce a mixture of diastereomers which can be separated by recrystallization or via high performance liquid chromatography ("HPLC") or other chromatographic methods to produce the pure diastereomer whose absolute stereochemistry can then be determined. Diastereomeric adducts may also, in some circumstances, be separated by fractional crystallization.

The compounds produced and claimed herein of formula I' may be selectively produced by chiral oxidation means of a sulfide moiety present on the described heteroaryl rings. The selective oxidation of the sulfide moiety to produce an enantiomerically enriched mixture wherein one enantiomer predominates as further described herein may also be coupled to a recycling process whereby the non-desired sulfinyl enantiomer may be reduced and reoxidized to form additional desired product. In general, a compound of formula I' may readily be obtained by synthetic methods described herein. An alkylthio moiety may be prepared prior to the chiral oxidation and/or recycling procedure. A process for preparing a compound of formula I' may proceed as follows:

(a) by treating a piperidone having formula II with a corresponding compound of formula $R^1Li$ in an aprotic solvent such as THF. The lithium compound can be conveniently generated in situ by reacting a compound of formula $R^1Z$, wherein Z is a halo group or, in some cases hydrogen, with a $C_{1-6}$ alkyl lithium compound such as n-butyl lithium in a temperature range of −20 to −100 degrees C.;

(b) by treating a corresponding amide of formula IIa with a suitable reducing agent, for example, lithium aluminum hydride or borane dimethylsulfide complex;

(c) by treating an aldehyde of formula III (G is hydrogen) with a corresponding piperidine of formula IV in the presence of a reducing agent such as, for example, sodium cyanoborohydride;

(d) for a compound of formula I wherein the value of $C_{1-6}$ alkoxy for either X or Y is desired, by treating a corresponding compound of formula I wherein X or Y is hydroxy with a desired base and alkylhalide to form the alkoxy compound(s).

The $C_{1-4}$ alkylthio derivatives used as precursors to the preferred chiral sulfoxides of the instant invention may readily be prepared according to the following basic procedure. To a solution of, for example, 1-(9,10-dihydro-9,10-methanoanthracen-9-ylmethyl)-4-(2-fluoro-3-pyridyl) piperidin-4-ol (which is prepared from reacting the anion of 2-fluoropyridine with 1-(9,10-dihydro-9,10-methanoanthracen-9-ylmethyl)-4-piperidone and lithium bromide) in a suitable solvent such as THF is added the sodium salt of a $C_{1-4}$ alkylthio compound which displaces the flouro group. The sodium alkylthiolate is readily prepared from the $C_{1-4}$ alkylthiol compound and sodium hydride under standard conditions. The reaction between the alkylthiolate and the 2-fluoro derivative is allowed to proceed under reflux for about a minimum of three hours and is subsequently quenched by pouring into water. The aqueous phase is extracted with ether or other suitable organic solvent and the resultant product is purified by suitable chromatographic means such as flash chromatography to obtain a 1-(9,10-dihydro-9,10-methanoanthrancen-9-ylmethyl)-4-(2-$C_{1-4}$ alkylthio-3-pyridyl)piperidin-4-ol compound. The preferred compound produced in this manner is the 2-ethylthio derivative. Of course, a suitable flouro-substituted heteroaryl compound as described herein may also be reacted with an alkylthiolate salt to produce suitable precursors to the claimed chiral sulfoxides.

The above 2-ethylthio derivative or other $C_{1-4}$ alkylthio derivative as described herein may then be oxidized enantioselectively to form a desired and biologically active dopemine receptor antagonist. The selective oxidation procedure of the described alkylthio compounds may proceed as follows. To a cooled solution (−20 degrees C.) of (−)-diethyl D-tartrate in a suitable solvent such as dry (anhydrous) toluene under a nitrogen atmosphere is added titanium tetraisopropoxide in a dropwise fashion. The mixture is stirred for about five minutes with the subsequent addition of an alkylthio derivative such as 1-(9,10-dihydro-9,10-methanoanthracen-9-ylmethyl)-4-(2-ethylthio-3-pyridyl)piperidin-4-ol which is added in one portion. The reaction is maintained at the above temperature for about 25 minutes and is then cooled to about −78 degrees C. before the addition of freshly dried t-butyl hydroperoxide (in slight molar excess) via syringe. The reaction is allowed to warm to −15 degrees C. over a several hour period (about 3 hours) and is then placed without stirring in a 15 degree freezer for about 18 hours. The reaction is then quenched by adding aqueous sodium hydroxide (about 1N). The suspension is then diluted with methylene chloride and the mixture is filtered through diatomaceous earth. After work-up, the product is purified by chromatographic means such as flash chromatography to give an enantiomeric mixture of chiral sulfoxides wherein the enantiomeric ratio is about 1:3.7 of (+)$C_{1-4}$ alkylsulfinyl methanoanthrancenyl compound to (−)$C_{1-4}$ alkylsulfinyl methanoanthracenyl compound (as determined by HPLC analysis of the enantiomers). Recrystallization of the product mixture in a suitable solvent such as hot toluene leads to an enantiomeric mixture with a ratio of 1:99 wherein the (−)-enantiomer predominates in the mother liquors. Crystallization of the mother liquor leads to a pure (−)-enantiomer as a crystalline solid. Scheme 4 depicts the specific chiral oxidation(s) of either the pyridyl ethyl thio compound or the heteroaryl (het) $C_{1-4}$ alkyl thio compound(s) to form the respective sulfinyl compound. In Scheme 4, het refers to the five and six membered heteroaryl rings as defined herein for R1. The preferred enantiomer produced in this manner is (−)-1-(9,10-Dihydro-9,10-methanoanthrancen-9-ylmethyl)-4-(2-ethylsulfinyl-3-pyridyl)piperidin-4-ol. The present invention therefore relates to a process for producing chiral sulfinyl methanoanthracenyl compounds comprising the steps of (a) reacting a compound of the formula I' wherein X and Y and $R^1$ are as defined herein except $R^1$ includes a $C_{1-4}$ alkylthio moiety with (b) an asymmetric oxidizing reagent selected from (1) titanium/tartrate/peroxide or (2) a chiral oxaziridine wherein the reaction proceeds enantioselectively to produce a chiral enantiomeric mixture of oxides of formula I'. The present invention also relates to a process comprising the steps as described above plus an additional recrystallization to afford an enantiomerically pure sulfinyl enantiomer of formula I'. Of course, the invention also encompasses those diastereomeric mixtures which result wherein at least one of the heteroaryl substituents is a chiral sulfinyl moiety and an additional chiral substituent is present on the heteroaryl group as defined herein or on the methanoanthracenyl nucleus. The present process produces significant enantiomeric excess and thus the present invention is directed to a novel process for producing enantiomeric methanoanthracenyl sulfoxides. A process for asymmetrically oxidizing aryl-alkyl sulfides of specific formulae to sulfoxides is described generally in Pitchen et al. J. Am. Chem. Soc. 1984, 106, 8188–8193. An oxaziridine procedure is generally described in Davis et al., J. Am. Chem. Soc. 1982, 104 5412. The processes described herein are directed to chiral sulfide oxidations of complex methanoanthracenyl alkyl sulfides. Other chiral oxidation processes which could be utilized under appropriate conditions include enzymatic means (via chloroperoxidase) or oxidation in the presence of bovine serum albumin. Enantiomeric ratios could vary also depending upon the particular heteroaryl moiety.

The present invention also relates to a process whereby the non-desired sulfoxide is reduced back to the sulfide which is then prepared for an additional enantioselective oxidation to produce the preferred enantiomer or diastereomer. For example, a compound such as a 1-(9,10-dihydro-9,10-methanoanthracen-9-ylmethyl)-4-($C_{1-4}$alkylthio-3-heteroaryl)piperidin-4-ol derivative may be synthesized by reducing the corresponding $C_{1-4}$alkylsulfinyl-3-heteroaryl derivative with a suitable reducing agent such as zinc dust/titanium tetrachloride. The preferred compound recycled in this manner is the racemate of or material containing the (+)-1-(9,10-dihydro-9,10-methanoanthrancen-9-ylmethyl)-4-(2-ethylsulfinyl-3-pyridyl)piperidin-4-ol which, after reduction, yields 1-(9,10)-dihydro-9,10-methanoanthrancen-9-ylmethyl)4-(2-ethylthio-3-pyridyl)piperidin-4-ol. Advantageously, this compound is then oxidized via the enantioselective process described herein to form additional (−)-enantiomer. Therefore, the present invention relates to a selective and dual process for preparing specific enantiomers or diastereomers of $C_{1-4}$ alkylsulfinyl methanoanthrancenyl compounds via a selective oxidation and recycling procedure. This process yields specific enantiomers or diastereomers which are useful as D1/D2 dopamine receptor antagonists such as the preferred (−)-1-(9,10-dihydro-9,10-methanoanthracen-9-ylmethyl)-4-(2-ethylsulfinyl-3-pyridyl)piperidin-4-ol compound. This compound has a surprisingly improved D1/D2 ratio which can generally be indicative of an improved clinical therapeutic profile in patients in need of treatment of disorder such as psychoses. Its D1 receptor antagonist activity is closer to its D2 receptor antagonist activity thus leading to a balanced D1/D2 profile which may be predictive of an improved clinical profile over conventional antipsychotic agents. Surprisingly, the (−)-enantiomer has an improved D1/D2 profile over the racemate of the same chemical formula.

Examples of suitable pharmaceutically acceptable salts of formula I' are organic addition salts formed with acids which form a physiologically acceptable anion, for example, tosylate, methanesulfonate, acetate, tartrate, citrate, succinate, benzoate, ascorbate, fumurate, maleate, alpha-ketoglutarate, and alpha-glycerophosphate. Suitable inorganic salts may also be formed such as sulfate, nitrate, phosphate and hydrochloride. Pharmaceutically acceptable salts may be obtained using standard procedures well known in the art, for example, by reacting a compound of formula I' with a suitable acid to afford a pharmaceutically acceptable salt.

When used to treat psychoses or other neurological disorders as recited herein, a compound of formula I' or preferably the compound (−)-1-(9,10)-Dihydro-9,10-methanoanthracen-9-ylmethyl)-4-(2-ethylsulfinyl-3-pyridyl)piperidin-4-ol is preferably used. This compound may be admixed with a pharmaceutically acceptable carrier or diluent and administered in a pharmaceutically effective amount to a patient in need of treatment thereof. The particular composition chosen may be dependent upon or adapted for the desired route of administration. Of course, these suitable pharmaceutical compositions are a further feature of the invention described herein. These compositions may be obtained by utilizing conventional procedures and by incorporating conventional pharmaceutical binders, excipients, fillers, inert ingredients, disintegrants and the like. The active compounds and/or the pharmaceutical compositions described herein may be prepared in a variety of dosage forms depending upon the preferred route of administration. Oral dosage forms may include tablets, capsules, solutions or suspensions. Intravenous, intravesicular, subcutaneous, or intramuscular injection or infusion dosage forms may be in the form of sterile solutions or suspensions. Suppository compositions may be prepared if rectal administration is necessary. Oral administration is the preferred route of administration for soluble salts within the scope of the present invention. Advantageously, the less soluble free amines or non-salt forms within the scope of the present invention are administered to a patient in a sustained release or DEPOT formulation wherein the active ingredient is slowly released over a period of days or other suitable period to a patient in need of treatment thereof. The present invention therefore also relates to a method of administering a therapeutically effective amount of the active compounds as disclosed herein via oral or DEPOT delivery means. Sustained release formulations and drug delivery means are generally described in Remingtons Pharmaceutical Sciences. There is a need for a long acting dosage form in the treatment of psychoses with sustained release properties capable of providing therapeutic 5HT2 serotonin, D1 and D2 dopamine antagonist plasma concentrations.

A DEPOT formulation containing the described active ingredients may be administered by implantation (for example, subcutaneously, transcutaneously or intramuscularly) or by intramuscular injection. These formulations may therefore be formulated with pharmaceutical excipients such as suitable polymeric or hydrophobic materials (e.g. as emulsions in oil) or as a sparingly soluble salt. The dosages of the DEPOT formulation are chosen to administer a pharmaceutically effective amount of the described D1/D2/5HT2 antagonist over an extended period of time.

The dose of a compound of formula I' which is administered to a patient in need of treatment thereof will necessarily vary depending upon the particular patient and the severity of their condition and their body weight and particular biochemistry. A clinician or physician of ordinary skill in the art can readily determine the suitable dosage from the ranges described herein and from the patients particular characteristics. In general, a compound of formula I' will be administered to a patient in need of treatment thereof (such as man) so that a pharmaceutically effective amount is received and this dosage is generally in the range of about 0.01 to about 10 mg/kg body weight. If a drug is administered intramuscularly, it is administered in the range of about 0.01 to about 5 mg/kg body weight. If it is administered orally, it is administered in the range of about 0.1 to about 10 mg/kg body weight. It will be apparent to those skilled in the art that a compound of formula I' can be co-administered with other therapeutic or prophylactic agents and/or medicaments that are not contraindicated therewith.

The compounds of formula I' are antagonists of both D1 and D2 dopamine receptors and therefore are useful as antipsychotic drugs. In addition, the compounds of formula I' are useful as 5HT2 serotonin receptor antagonists and thus are further useful as antipsychotics. These compounds therefore have significant serotonin antagonist activity as well as a balanced D1/D2 profile. D1 and D2 and 5HT2 antagonism may be shown by standard tests as described below. D2 antagonism can be shown by standard tests such as antagonism of [$^3$H]-spiperone binding and/or antagonism of apomorphine-induced climbing and apomorphine-induced disruption of swimming. Additional tests are described below. The following are non-limiting examples of the antagonism of the compounds of the invention of formula I' on the D1, D2 and 5HT2 receptors and clearly show an improved and balanced receptor antagonist profile.

TEST C

Receptor binding assays used to quantitate the affinities of compounds for the Dopamine D-1, Dopamine D-2 and Serotonin 5HT2 receptors were performed according to Saller and Salama (J Pharm Exp Ther 236 pg. 714, 1986) and Saller et al. (J Pharm Exp Ther 253 pg. 1162, 1990) with minor modifications. In brief, the Dopamine D-1 binding assays were carried out at 37° C. for 15 minutes in 1.0 ml of 50 mM Tris-HCl containing 120 mM NaCl, 5 mM KCl, 2 mM CaCl2 and 1 mM MgCl2 (pH=7.4), membranes from 3 mgs tissue from rat striatum and 0.3 nM [$^3$H]SCH 23390. The Dopamine D-2 binding assays were carried out at 37° C. for 15 minutes in 1.0 ml of 50 mM Tris-HCl (pH=7.7) containing 40 nM ketanserin, membranes from 4 mgs tissue from rat striatum and 0.1 nM [$^3$H]Spiperone. The Serotonin 5HT2 binding assays were carried out at 37° C. for 15 minutes in 1.0 ml of 50 mM Tris-HCl (pH=7.7), membranes from 5 mgs tissue from rat frontal cortex and 0.5 nM [$^3$H]Ketanserin. All assays reactions were terminated by rapid filtration over Whatman GF/B filters. Radioactivity on the filter was determined by scintillation counting. Nonspecific binding for D-1, D-2 and 5HT2 assays was defined as the binding activity in the presence of 1 μM SCH 23390, butaclamol or ketanserin, respectively, and was subtracted from the total binding to determine specific binding. Each assay was carried out at least three times in triplicate. $IC_{50}$ values were determined from a least squares regression of a logit-log transformation of the data. Ki values were calculated from the determinations using the following equation: $Ki=IC50/(L+Kd)$, where L=ligand concentrations used in the assays and Kd=equilibrium dissociation constant of the radioligands as determined from saturation experiments. The $K_i$ values of, for example, racemic 1-(9,10-dihydro-9,10-methanoanthracen-9-ylmethyl)-4-(2-ethylsulfinyl-3-pyridyl)piperidin-4-ol were 118 nM, 10 nM, and 21 nM for the D1, D2 and 5HT2 receptors respectively. The pure (about 100%) levorotatory isomer of the above compound gave 13 nM, 42 nM and 39 nM.

TEST D

Female Swiss-Webster mice weighing approximately 20 g were deprived of food for approximately 24 h and then dosed orally with various doses of either the vehicle or test agent over a range of doses (N=20 mice per treatment group). Thirty minutes later they were dosed with amorphine HCl at 1.25 mg/kg, sc, and placed into climbing cages. The climbing cages were 9 cm side, 15 cm deep and 30 cm high. One wall had 27 horizontal rungs spaced 1 cm apart. Thirteen minutes after apomorphine administration, each mouse was observed continuously for 1 min and the highest and lowest rung reached by its front paws was recorded. The mean of these two scores was used as the score for that mouse (the highest and lowest scores were 27 and 0, respectively). Immediately after the 1-min climbing observation period each mouse was placed into a circular swimming tank for 2 min and the number of swims was counted. The height of the tank was 15 cm and the diameter was 28 cm. A circular obstacle measuring 10.5 cm in diameter and having a height of 17 cm was placed into the center of the tank, creating a circular swimming channel 8.75 cm wide. The water level was 5.5 cm and the water was kept at room temperature. Marks were placed on the floor and the side of the tank 180 degrees apart. A "swim" was scored each time a mouse swam from one mark to the other. The mice were observed through overhead mirrors and the number of 180 degree swims was recorded for each mouse. Activity in this test was indicated by a decrease in the climbing score accompanied by an increase in the swimming score at a given dose of the test compound. Results are expressed as ED50s for climbing and swimming,.i.e., dose at which there was a 50% decrease in climbing and dose at which there was a 50% increase in swimming. Typical results for climbing and swimming respectively were ED50s of 0.54 and 1.7 mg/kg po for the racemate described above and 1.3 and 1.6 mg/kg po for the pure levorotatory isomer.

TEST E

Ten μg of 6-hydroxydopamine dissolved in 2 μl physiological saline containing 0.1 mg/ml ascorbic acid was injected into the left substantia nigra of male Sprague Dawley rats under sodium pentobarbital anesthesia at least one month prior to the experiment, according to the method of Perese et al. (Brain Research, 494, pg 285, 1989). The stereotaxic coordinates from Bregma were: AP −5.2, L +2.0, V −7.5. Ipsiversive and contraversive rotational behavior was monitored using Plexiglas cylinder rotometers (Columbus Instruments; Rota-Count-8) and the number of rotations made in 5 minute intervals was recorded for the entire duration of drug effect. Animals exhibiting >500 contralateral rotations/2.5 hour post-injection period in response to L-DOPA (50 mg/kg i.p.; t=0) and benzerazide (30 mg/kg i.p.; t=−15 min) were used for further testing. Contraversive rotational behavior also was dose-dependently induced by the Dopamine D-1 selective agonist, SKF 38393. We examined the antagonism of a subthreshold dose (20 mg/kg i.p.) of SKF 38393-induced circling behavior with the racemate described above and the respective 95% pure isomer. SKF 38393 and the racemate or the 95% pure isomer were administered simultaneously (t=0) and rotational behavior was measured for 60 minutes. We found that the racemate described above had an IC50 value (drug concentration which produced a 50% inhibition of SKF 38393-induced rotations) of 3.95 mg/kg (i.p.) and the member of the heteroaryl $C_{1-4}$ alkyl sulfinyl class described above (95% pure $C_{1-4}$ alkyl sulfinyl levorotatory isomer) had an IC50 value of 1.98 mg/kg (i.p.).

Test F

Male Sprague Dawley rats weighing 60–120 g were deprived of food for approximately 24 h and then dosed orally with either vehicle or test agent over a range of doses (N=9 rats per treatment group). Twenty minutes later they are dosed with quipazine dimaleate, 2.5 mg/kg i.p. and placed singly in plexiglass chambers. Five minutes after dosing with quipazine, the number of head twitches are counted for a fifteen minute period. Results are analyzed by determining mean head twitch scores and percent inhibition for the drug treated vs the vehicle treated groups and reported as ED50s, i.e., dose at which there is a 50% reduction in head twitch scores. Typical results in this test were ED50s of 0.61 mg/kg po for the racemic agent and 1.38 mg/kg po for the pure isomer (100%).

In general, compounds were considered active if they provided an $IC_{50}$ value of 500 nM or less in Test A, and/or were active following an oral dose of 40 mg/kg or less in Test B.

The invention will now be illustrated by the following non-limiting examples in which, unless stated otherwise:

(i) temperatures are given in degrees Celsius (C.); operations were carried out at room or ambient temperature, that is, at a temperature in the range of 18°–25° C.

(ii) evaporation of solvent was carried out using a rotary evaporator under reduced pressure (600–4000 pascals; 4.5–30 mmHg) with a bath temperature of up to 60° C.;

(iii) flash chromatography was carried out on Merck Kieselgel (Art 9385) or Baker Flash silica gel; thin layer chromatography (TLC) was carried out on Analtech 0.25 mm silica gel GHLF plates (Art 21521), obtainable from Analtech, Newark, Del., U.S.A.;

(iv) high pressure liquid chromatography (HPLC) for analysis of enantiomeric purity determinations of chiral compounds was carried out on either a 25cm×4.6mm Chiralcel¤ OD or a 15cm×4.6 mm Ultron Ovomucoid column available from J. T. Baker, Inc.; HPLC analyses for most reactions and final products was carried out on either a 25cm×4.6 mm Supelcosil¤ LC-8-DB, a 25 cm×4.6 mm Supelcosiln¤ LC-18-DB column, available from Supelco, State College, Pennsylvania, U.S.A. or a 25 cm×4.6 mm Zorbax RX column.

(v) in general, the course of reactions was followed by TLC and/or HPLC and reaction times are given for illustration only;

(vi) melting points are uncorrected and (dec) indicates decomposition; the melting points given are those obtained for the materials prepared as described; polymorphism may result in isolation of materials with different melting points in some preparations;

(vii) all final products were essentially pure by TLC and/or HPLC and had satisfactory nuclear magnetic resonance (NMR) spectra and microanalytical data;

(viii) yields are given for illustration only;

(ix) reduced pressures are given as absolute pressures in pascals (Pa); other pressures are given as gauge pressures in bars;

(x) chemical symbols have their usual meanings; the following abbreviations have also been used: v (volume), w (weight), mp (melting point), L (liters), mL (milliliters), g (grams), mmol (millimoles), mg (milligrams), min (minutes), h (hour); and (xi) solvent ratios are given in volume: volume (v/v) terms.

EXAMPLE 1

1-(2-Chloro-9,10-dihydro-9,10-methanoanthracen-9-ylmethyl)-4-(3-pyridyl)piperidin-4-ol To a cooled solution (−90° C.) of n-butyllithium (2.5M in hexane, 2.40 mL, 6.0 mmol, 1.5 eq) in tetrahydrofuran (40 mL) under nitrogen was added freshly distilled 3-bromopyridine (0.540 mL, 5.6 mmol, 1.4 eq). The metal-halogen exchange reaction was warmed to −75° C. and maintained for 1.5 h. During that time a dark green solution evolved with the appearance of fine particulate. A solution of 1-(2-chloro-9,10-dihydro-9,10-methanoanthracen-9-ylmethyl)-4-piperidinone (1.35 g, 4.0 mmol) in tetrahydrofuran (10 mL) was then added dropwise with considerable lightening of the solution color to a deep yellow. The reaction was warmed to room temperature over 1 h and quenched with water (50 mL). The aqueous phase was extracted with ethyl acetate (3×60 mL). Combined organic extracts were dried over anhydrous magnesium sulfate, filtered, and reduced to an oil. The reaction mixture was purified by flash chromatography over silica gel (80 mL, eluent: ethyl acetate) to yield 1.35 g (81%) of the title compound as a white solid. TLC analysis ($R_f$ 0.20, ethyl acetate). 1H NMR ($D_6$-DMSO, 300 MHz) 8.69 (br s, 1H), 8.41 (d, J=4.5 Hz, 1H), 7.83 (dt, J=8.0 Hz, 1H), 7.29 (m, 5H), 6.95 (m, 3H), 5.05 (s, 1H), 4.35 (s, 1H), 3.41 (m, 2H), 3.34 (s, 1H), 2.75 (m, 4H), 1.92 (m, 2H), 1.62 (m, 2H) MS (CI, $CH_4$) m/z 417 (M+1,100), 419 (36), 445 (M+29,15), 399 (15) The free base was dissolved in diethyl ether containing a small amount of methylene chloride, acidified with ethereal HCl, and the hydrochloride salt suspension was diluted with additional ether. The salt was filtered, washed with fresh ether and dried in vacuo (50° C., 13 pascal, 18 h) to yield a white solid, mp 225°–228° C. (dec).

Analysis for $C_{26}H_{25}ClN_2O.2.1HCl.H_2O$: Calculated: C, 61.04; H, 5.73; N, 5.48 Found: C, 60.91; H, 5.64; N, 5.29

The starting piperidinone was prepared as follows:

a. 2-Chloroanthracene

A stirred suspension of 2-chloroanthraquinone (1260 g, 5.19 mol) in concentrated ammonium hydroxide (7.5 L) and water (2.5 L) was warmed to 40° C. Zinc dust (845 g, 12.93 mol) was added in one portion, changing the color to deep red. The mixture was stirred for 45 min at 50° C., then cautiously treated with a second portion of zinc dust (845 g). After the addition, the stirred mixture was heated gradually over 3 h to 90° C., then maintained at 90°–95° C. for 2 h (red color dissipated). TLC analysis (silica gel; hexane:methylene chloride (3:1)) showed complete conversion of the anthraquinone ($R_f$ 0.35) to the desired anthracene ($R_f$ 0.80). The reaction mixture was stirred overnight as it cooled to room temperature. The cooled mixture was treated with methylene chloride (4 L), stirred for 2 h, then filtered through Celite to remove the excess zinc. The filter cake was washed with methylene chloride (6×1L). The methylene chloride layer was separated from the aqueous, then treated with 6N hydrochloric acid (3 L) and stirred for 2 h. A first crop of 2-chloroanthracene was collected by filtration and washed with water (4×1 L). Vacuum drying afforded a light yellow crystalline product weighing 804.6 g (mp 220°–221° C.). The methylene chloride portion of the filtrate was concentrated in vacuo to 10% of it's original volume. This produced an additional 158.5 g of the desired compound for a total yield of 963.1 g (87.2%). 1H NMR ($CDCl_3$) 8.39 (s, 1H), 8.30 (s, 1H), 7.96 (s, 4H), 7.49 (s, 2H), 7.36 (d, J=8.7 Hz, 1H)

b. 2-Chloro-9-formylanthracene

N-methylformanilide (2.45 kg, 18.12 mol) was treated with phosphorus oxychloride (2.66 kg, 17.35 mol) over a 40 min period at ambient temperature. The intermediate Viismeler complex was stirred for 2 h at room temperature, then treated with 2-chloroanthracene (described in example 1a) (963 g, 4.53 mol), and o-dichlorobenzene (1.0 L). The resulting bright yellow mixture was heated gradually over 1.5 h to 9° C. at which point an exotherm ensued raising the reaction temperature to 115° C. The heat was removed until the exotherm subsided (45 min), after which time the mixture was heated for 9 h at 90° C., then cooled. TLC analysis (silica gel; ethyl acetate:hexane 1:4) showed a small amount of unreacted anthracene ($R_f$ 0.90), a small amount of the 3-chloro isomer ($R_f$ 0.65), and the 2-chloro isomer ($R_f$ 0.58) as the major component. The cooled reaction mixture was poured into ice/water (27 L) precipitating a dark brown tar. The aqueous layer was decanted away from the tar and extracted with methylene chloride (5×2 L). The combined extracts were used to redissolve the tar. The methylene chloride solution was washed with 3N hydrochloric acid (4×1.5 L), followed by water (2 L), then dried over magnesium sulfate. The extracts were filtered, then pressure-filtered through a bed of silica gel, eluting with methylene chloride until all of the desired compound had been recovered. The eluent was concentrated on the rotary evaporator to give a slurry of bright yellow crystals (in o-dichlorobenzene). The crystals were collected by filtration, washed with diethyl ether (2×500 ml), then vacuum dried to afford 619.7 g (56.9%) of the desired 2-chloro-9-formylanthracene (mp 148°–150° C.). 1H NMR ($CDCl_3$) 11.35 (s, 1H), 9.02 (d, J=0.9 Hz, 1H), 8.81 (d, J=8.9 Hz, 1H), 8.56 (s, 1H), 7.98 (m, 1H), 7.90 (d, J=8.9 Hz, 1H), 7.66 (m, 1H), 7.53 (m, 1H), 7.42 (m, 1H)

c. 12-Acetoxy-2-chloro-9-formyl-9,10-dihydro-9,10-ethanoanthracene (E and Z isomers)

A mixture of 2-chloro-9-formylanthracene (described in example 1b) (100.0 g, 0.415 mol) and vinyl acetate (400 ml, 374 g, 4.34 mol) was placed in a stainless steel bomb (PARR) and heated at 200° C. (sand bath temp.) for 24 h, then cooled. The reaction mixture was concentrated on the rotary evaporator to remove the excess vinyl acetate, leaving the crude product as a tan crystalline solid. The crude product from several batches, which consumed 670.0 g (2.78 mol) of the 2-chloro-9-formylanthracene, was pooled. Trituration with diethyl ether (1.0 L) gave an off-white crystalline solid which was collected by filtration, washed with diethyl ether (2×300 ml), then vacuum dried to afford 629.0 g (69.1%) of the title compound (mp 145°–153° C.). 1H NMR (CDCl$_3$) 10.58 (s) and 10.64 (s, 1H), 7.63 (m) and 7.76 (d, J=1.5 Hz, 1H), 7.15–7.36 (m, 6H), 5.46 (m, 1H), 4.29 (s, 1H), 2.55 (m, 1H), 1.88 (s) and 1.91 (s, 1H), 1.55 (m, 1H)

Evaporation of the filtrates and washes gave a thick brown oil, which was purified by column chromatography over silica gel eluting with a solvent mixture of methylene chloride:hexane (1:1). The recovered solid was recrystallized from diethyl ether:hexane (1:1); 400 mL) to afford an additional 175.5 g (19.3%) of the desired compound.

d. 12-Acetoxy-2-chloro-9,10-dihydro-9,10-ethano-9-anthracenecarboxylic acid (E and Z isomers).

A stirred solution of 12-acetoxy-2-chloro-9-formyl-9,10-dihydro-9,10-ethanoanthracene (described in example 1c) (629.0 g, 1.925 mol) dissolved in acetone (8.0 L) was treated with Jones Reagent (1.50 L, approx. 1.93 mol, prepared as described in Fieser & Fieser Vol. 1: pp 142) over a period of 1 h at 10°–20° C. After the addition of the Jones Reagent, the reaction mixture was stirred for 4 h at room temperature. TLC analysis (silica gel, methylene chloride) showed complete consumption of the aldehyde (R$_f$ 0.73). Isopropanol (100 mL) was added and the reaction stirred for 18 h to quench any excess Jones Reagent, resulting in a white suspension over a green-black sludge (chromium salts). The white supernatant was drawn off, and the sludge washed with acetone (5×500 mL). The acetone washes were combined with the supernatant and concentrated on the rotary evaporator to a final volume of 2 L. The residue was poured into ice/water (10 L) and stirred vigorously for 5 h yielding an off-white solid. The material was collected by filtration, washed with water (3×1L), then vacuum dried to give 665.3 g (quantitative) of the desired carboxylic acid (mp 270°–273° C. (dec)) 1H NMR (D$_6$-DMSO) 13.95 (s, 1H), 7.79 (m) and 7.87 (s, 1H), 7.12–7.45 (m, 6H), 5.27 (d, J=6.4 Hz, 1H), 4.48 (s, 1H), 2.35 (m, 1H), 1.81 (s) and 1.84 (s, 3H), 1.38 (m, 1H) IR max (KBr) 1690 cm−1, C=O, —COOH; 1740 cm−1, C=O, —COCH$_3$ e. 12-Acetoxy-2-chloro-9,10-dihydro-9,10-ethano-9-anthracen-9-ylcarbonyl chloride (E and Z isomers).

12-Acetoxy-2-chloro-9,10dihydro-9,10-ethano-9-anthracenecarboxylic acid (described in example 1d) (665.0 g, 1.94 mol) was suspended in toluene (8.0 L). Thionyl chloride (400 g, 3.36 mol) was added in one portion at room temperature followed by a catalytic amount (2 mL) of N,N-dimethylformamide. The mixture was heated gradually to reflux (80° C.) over 1 h, then maintained at reflux for 8 h, yielding a clear amber solution. The cooled reaction mixture was concentrated on the rotary evaporator under pump vacuum to remove the toluene. The crude acid chloride was isolated as a waxy brown solid (804 g, 115% of theoretical), and was used crude in the next reaction. A small sample of the material was dried under high vacuum to provide a sample for spectral characterization. 1H NMR (CDCl$_3$) 7.87 (m, 1H), 7.18–7.40 (m, 6H), 5.57 (m, 1H), 4.29 (s, 1H), 2.58 (m, 1H), 1.91 (s) and 1.94 (s, 3H), 1.50 (m, 1H) IR max (neat film): 1750 cm−1, C=O, —COCH$_3$; 1790 cm−1, C=O, —COCl f. 12-Acetoxy-2-chloro-9,10-dihydro-9,10-ethanoanthracen-9-ylcarbonyl azide (E and Z isomers).

The crude 12-acetoxy-2-chloro-9,10dihydro-9,10-ethano-9-anthracen-9-ylcarbonyl chloride (described in example 1e) (804 g, approx 1.94 mol) was dissolved in acetone (8.0 L) and the resulting solution cooled by an ice/methanol bath to −5 C. The stirred mixture was treated with an aqueous solution of sodium azide (380 g, 5.84 mol in 1.0 L of water) added over a period of 30 min The resulting tan suspension was stirred for 3 h at 0° C., then allowed to warm to room temperature. The mixture was concentrated on the rotary evaporator at 15°–20° C. using pump vacuum to remove the acetone. The residue was partitioned between water (5 L) and toluene (5 L), stirred for 1 h, then filtered. The two-phase filtrate was separated and the aqueous portion extracted with toluene (5×1 L). The toluene extracts were used to redissolve the filter cake isolated earlier. The combined toluene solutions were washed with brine solution (2 L), then dried over magnesium sulfate. The toluene was filtered, then concentrated to ½ volume on the rotary evaporator at 15–20 C. under pump vacuum. This gave a toluene solution of the acyl azide (yield assumed to be quantitative), which was used in the next reaction. A small sample of the solution was evaporated under high vacuum to isolate a sample of the acyl azide as an off-white sticky solid for spectral characterization. 1H NMR (CDCl$_3$) 7.80 (m, 1H), 7.16–7.33 (m, 6H), 5.39 (m, 1H), 4.27 (t, J=2.6 Hz, 1H), 2.50 (m, 1H), 1.89 (s) and 1.92 (s, 3H), 1.47 (m, 1H) IR max (nujol): 1720 cm−1, C=O, —CON3; 1750 cm−1, C=O, —COCH$_3$: 2160 cm−1, —N=N=N g. 12-Acetoxy-2-chloro-9-isocyanato-9,10-dihydro-9,10-ethanoanthracene (E and Z isomers).

The toluene solution of the crude acyl azide isolated in the previous reaction (approx 713.5 g, 1,94 mol in 6.0 L of toluene) was heated gradually over a 30 min period to 65° C. At this point, rapid evolution of nitrogen ensued, accompanied by an exotherm which raised the temperature of the reaction mixture to 95° C. The heating mantle was removed until the exotherm subsided (30 min), after which time the reaction was heated at reflux for 3 h, then allowed to cool. The toluene was removed on the rotary evaporator using pump vacuum, isolating the crude isocyanate as a thick amber oil (738.5 g, 112% of theoretical). This material was used in the next reaction without further purification. A sample of the oil was dried under high vacuum to provide a sample for spectral characterization. 1H NMR (CDCl$_3$) 7.54 (m, 2H), 7.15–7.30 (m, 5H), 5.03 (m, 1H), 4.26 (t, J=2.6 Hz, 1H), 2.55 (m, 1H), 1.98 (s) and 2.00 (s, 3H), 1.56 (m, 1H) IR max (neat film): 1750 cm−1, C=O, —COCH$_3$; 2260 cm−1, —N=C=O h. 9-Amino-2-chloro-12-hydroxy-9,10-dihydro-9,10-ethanoanthracene (E and Z isomers).

The crude isocyanate from the previous reaction (738.5 g, 1.94 mol) was dissolved in absolute ethanol (7.0 L) giving a light amber solution. The stirred solution was treated with 20% aqueous sodium hydroxide solution (800 g, 20.0 mol in 4.0 L of water) added in one portion at room temperature. The reaction mixture turned red-brown immediately upon addition of the base. The mixture was heated at reflux for 8 h, then cooled. TLC analysis (silica gel, methylene chloride) showed complete consumption of the isocyanate (R$_f$ 0.80). The reaction mixture was concentrated on the rotary evaporator to remove the ethanol, leaving an aqueous suspension of the product which was extracted with methylene chloride (3×5 L). The combined extracts were washed with water (2 L) and brine solution (1L), then dried over magnesium sulfate. Filtration, followed by removal of the solvent in vacuo, yielded the crude amino alcohol as a sticky yellow-brown solid. Trituration with diethyl ether (1.0 L) afforded the pure compound as a cream colored powder weighing 445.8 g (84.5%) (mp 164°–167° C. ). 1H NMR (CDCl$_3$)

7.09–7.43 (m, 7H), 4.21 (t, J=2.6 Hz, 1H), 3.77 (m, 1H), 2.35 (m, 1H), 2.25 (br s, 3H), 1.48 (m, 1H)

i. 2-Chloro-9-formyl-9,10-dihydro-9,10-methanoanthracene

The 9-amino-2-chloro-12-hydroxy-9,10-dihydro-9,10-ethanoanthracene (described in example 1h) (445.5 g, 1.64 mol) was dissolved in glacial acetic acid (4.0 L), and the resulting solution cooled to 10° C. A solution of sodium nitrite (340.0 g, 4.93 mol) in water (1.4 L) was added to the reaction mixture over a period of 1.75 h. The temperature of the mixture was maintained at 10° C. during the addition of the nitrite, and for 4 h thereafter. The mixture was then stirred overnight and allowed to warm to room temperature. TLC analysis (silica gel, toluene:ethyl acetate (4:1)) showed complete conversion of the amino alcohol ($R_f$ 0.12) to 2-chloro-9-formyl-9,10-dihydro-9,10-methanoanthracene ($R_f$ 0.80). The reaction mixture was diluted with water (4 L) which caused precipitation of a reddish-brown tar. The aqueous supernatant was decanted away from the tar, diluted with an equal volume of crushed ice, then adjusted to pH 5–6 with solid sodium hydroxide. The resulting aqueous mixture was extracted with ethyl acetate (3×1.5 L). The combined ethyl acetate extracts were used to redissolve the tar, and the resulting solution washed with brine (2×1 L) then dried over magnesium sulfate. Filtration, followed by removal of the solvent in vacuo, gave the crude product as a thick brown oil. Purification of this material by column chromatography over silica gel, eluting with a solvent mixture of methylene chloride:hexane (1:1), afforded a thick yellow oil which crystallized on standing (311.7 g, 74.6%). Trituration with diethyl ether:hexane (1:6, 700 mL) gave a first crop of pure title compound as an off-white crystalline solid weighing 224.1 g (53.6%, mp 91°–92° C.). 1H NMR (CDCl$_3$) 10.39 (s, 1H), 7.50 (d, J=1.9 Hz, 1H), 7.39 (m, 1H), 7.31 (m, 1H), 7.20 (d, J=7.8 Hz, 1H), 7.01 (m, 3H), 4.37 (s, 1H), 2.80 (m, 2H)

Material recovered from the mother liquors and washes was repurified by column chromatography as previously described to give an additional 65.0 g (15.5%) of the title compound.

j. 2-Chloro-9,10-dihydro-9,10-methano-9-anthracenecarboxylic acid

To a cooled solution (0° C.) of 2-chloro-9-formyl-9,10-dihydro-9,10-methanoanthracene (described in example 1i) (20.0 g, 78.5 mmol) in acetone (260 mL) was added Jones reagent (24 mL; 27 g chromium trioxide, 23 mL water diluted up to 100 mL of reagent solution) in portions. The reagent was added until an orange color persists. The reaction, containing a significant amount of reduced chromium salts, was warmed to room temperature. The solvents were removed in vacuo and replaced with water (300 mL) saturated with sodium chloride. The aqueous phase was extracted with ethyl acetate (3×300 mL). Combined organic extracts were extracted with 2.5N NaOH (3×400 mL). The basic aqueous extracts were acidified with 3N HCl, saturated with sodium chloride, and extracted with ethyl acetate (4×300 mL). Combined organic extracts were dried over anhydrous magnesium sulfate, filtered, and reduced to a off-white solid. The procedure yielded 26.66 g (quantitative) of the title compound. No additional purification was required. 1H NMR (D$_6$-DMSO, 300 MHz) 13.2 (donfield) 7.46 (br s, 1H), 7.36 (m, 3H), 7.02 (m, 3 H), 4.45 (s, 1H), 2.67 (s, 2H) MS (CI, CH4) m/z 271 (M+1,100), 273 (34), 299 (M+29,17), 253 (33), 243 (22), 227 (20)

k. 1-(2-Chloro-9,10-dihydro-9,10-methanoanthracen-9-ylcarbonyl)piperidin-4-ol

To a solution of 2-chloro-9,10-dihydro-9,10-methano-9-anthracenecarboxylic acid (described in example 1j) (6.51 g, 24.1 mmol) in toluene (70 mL) was added thionyl chloride (2.28 mL, 31.3 mmol, 1.3 eq). The reaction was heated to reflux monitoring gas evolution with a mineral oil bubbler. The system reached a steady state within 40 min at which time it was slightly cooled and 4-hydroxypiperidine (6.08 g, 60.3 mmol, 2.5 eq) was added portionwise. A significant amount of heat is evolved and the reaction becomes dark. The suspension was heated to reflux for 2 h, cooled to room temperature and stirred for 18 h. The reaction was diluted with ethyl acetate (200 mL) and washed with 3 N HCl (2×100 mL), 2.5 N NaOH (2×100 mL) and saturated brine (200 mL). The organic phase was dried over anhydrous magnesium sulfate, filtered, and reduced to an oil. The procedure yielded 6.95 g (82%) of the title compound as a viscous oil. No addition purification was required. 1H NMR (D$_6$-DMSO, 250 MHz) 7.63 (m, 1H), 7.21 (m, 6H), 4.41 (s, 1H), 4.18 (m, 1H), 3.65 (m, 2H), 3.25 (m, 2H), 2.76 (m, 2H), 1.90 (m, 2H), 1.38 (m, 2H) MS (CI, CH4) m/z 354 (M+1, 100), 356 (36), 382 (M+29,19), 336 (27), 318 (9)

l. 1-(2-Chloro-9,10-dihydro-9,10-methanoanthracen-9-ylmethyl)piperidin-4-ol

To a cooled suspension (0° C.) of 1-(2-chloro-9,10-dihydro-9,10-methanoanthracen-9-ylcarbonyl)piperidin-4-ol (described in example 1k) (6.95 g, 19.6 mmol) in diethyl ether (200 mL) under nitrogen was added lithium aluminum hydride (1.49 g, 39.2 mmol, 8 eq of hydride) in portions. The suspension was stirred at 0° C. for 30 min and warmed to room temperature. After 18 h at room temperature, the excess reagent was carefully quenched with the following in sequence: water (1.5 mL), 2.5N NaOH (1.5 mL) and additional water (4.5 mL). The suspension was stirred vigorously until the aluminum salts became a granular white solid. The suspension was diluted with ethyl acetate (100 mL), dried with a small amount of anhydrous magnesium sulfate and filtered. The filter cake was rinsed thoroughly with ethyl acetate. The solvent was removed to yield 6.16 g (92%) of the title compound as a white solid. No additional purification was required. TLC analysis ($R_f$ 0.15, 50% ethyl acetate in hexane). 1H NMR (CDCl$_3$, 300 MHz) 7.20 (m, 4H), 6.95 (m, 3H), 4.60 (s, 1H), 4.24 (s, 1H), 3.70 (m 1H), 3.34 (s, 2H), 2.88 (m, 2H), 2.58 (s, 2H), 2.37 (m, 2H), 1.85 (m, 2H), 1.57 (m, 2H) MS (CI, CH4) m/z 340 (M+1,98), 342 (33), 322 (100), 368 (M+29,22), 114 (26)

m. 1-(2-Chloro-9,10-dihydro-9,10-methanoanthracen-9-ylmethyl)-4-piperidinone

To a cooled solution (−78° C.) of oxalyl chloride (3.06 mL, 35.1 mmol, 2 eq) in methylene chloride (100 mL) under nitrogen was added distilled dimethylsulfoxide (5.00 mL, 70.2 mmol, 4 eq). After 10 min 1-(2-chloro-9,10-dihydro-9,10-methanoanthracen-9-ylmethyl)piperidin-4-ol (described in example 1l) (5.96 g, 17.5 mmol) was added as a methylene chloride solution (10 mL). The reaction was stirred at −78° C. for 30 min prior to the addition of triethylamine (19.6 mL, 140 mmol, 8 eq). The cooling bath was removed and the reaction warmed to room temperature over 1.5 h. The reaction was poured into 2.5N NaOH (100 mL) and the aqueous phase extracted with methylene chloride (3×100 mL). Combined organic extracts were dried over anhydrous magnesium sulfate, filtered, and reduced to an oil. The crude reaction mixture was purified by flash chromatography over silica gel (400 mL, eluent: 20% ethyl acetate in hexane) to yield 5.53 g (93%) of the title compound. TLC analysis ($R_f$ 0.21, 20% ethyl acetate in hexane). 1H NMR (CDCl$_3$, 250 MHz) 7.26 (m, 1H), 7.13 (m, 3H), 6.95 (m, 3H), 4.28 (s, 1H), 3.49 (s, 2H), 2.94 (t, J=6.1Hz, 4H), 2.62 (s, 2H), 2.43 (t, J=6.0 Hz, 4H) MS (CI, CH4) m/z 338 (M+1,100), 340 (35), 366 (M+29,31)

The chloromethanoanthracene acid was resolved as follows:

n. Optical resolution of (9S,10S) 2-chloro-9,10-dihydro-9,10-methano-9-anthracenecarboxylic acid To a solution of racemic 2-chloro-9,10-dihydro-9,10-methano-9-anthracenecarboxylic acid (described in example 1j) (100 g, 0.37 mol) in ethyl acetate (1.5 L) and methanol (75 mL) was added solid (1S,2S)-(+)-pseudoephedrine (61.1 g, 0.37 mol). With efficient agitation the mixture was warmed to reflux, held at reflux for 30 and slowly cooled to 25 C. After a minimum of 2 h the slurry was filtered and washed with ethyl acetate to yield enriched diastereomeric salt (88.6 g, 0.20 mol, 55%; diastereomeric ratio 80:20 as determined by HPLC). The enriched salt was slurried in 3% methanolic ethyl acetate (2.74 L), warmed to reflux, and held at reflux for 30 min. The slurry was cooled to 25° C. slowly, stirred for 2 h, filtered, and washed with ethyl acetate to provide additional enriched salt (70 g, 0.16 mol, 79%, diastereomeric ratio 95:5 as determined by HPLC) Treatment of the enriched salt with 5% methanolic ethyl acetate using the same procedure yielded highly enriched salt (60.0 g, 0.14 mol, 85%, diastereomeric ratio 99:1 as determined by HPLC) This salt (60 g, 0.14 mol) was added to water (1 L) and the resulting suspension acidified to pH 2–3 with concentrated hydrochloric acid (15 mL) and then extracted with diethyl ether (3×500 mL). The combined organic extracts were washed with brine, dried over anhydrous magnesium sulfate and evaporated to an oil. Hexane was added and reduced in vacuo to afford enantiomerically enriched acid (36 g, 0.13 mol, 98% recovery, enantiomeric ratio 99:1 as determined by HPLC) as a white solid. Crystallization from a mixture of hexane (360 mL) and cyclohexane (720 mL) afforded enantiomerically pure (9S,10S)-2-chloro-9,10-dihydro-9,10-methano-9-anthracenecarboxylic acid as a white solid (30 g, 0.11 mol, 81%) mp 172°–173° C. rotation alpha (sodium D): +101 degrees (c=2, CHCl$_3$)

Analysis for C$_{16}$H$_{11}$ClO$_2$: Calculated: C, 70.99; B, 4.10 Found C, 70.81; H, 4.21

1H NMR 7.48–7.62 (m, 2H), 7.27–7.35 (m, 1H), 7.22 (d, J=7.8 Hz, 1H),6.90–7.10 (m, 3H), 4.35 (s, 1H), 2.80–2.95 (m, 2H)

HPLC analysis: Column: Ultron Ovomucoid (ES-OVM) 15 cm×6 mm Eluent: 15% acetonitrile/85% aqueous KH2PO4 buffer (10 mM) adjusted to pH 5.5 with 1M potassium hydroxide. Flow: 1 mL/min Wavelength: 230 nm Retention times: (+) enantiomer 15.4 min/(−) enantiomer 19.6 min. The (9R,10R) 2-Chloro-9,10-dihydro-9,10-methano-9-anthracenecarboxylic acid was resolved as follows:

o.

Using a procedure similar to that described in example 1n, except employing (1R,2R)-(−)-pseudoephedrine as the resolving agent, the (9R,10R)-(−)-2-chloro-9,10-dihydro-9,10-methano-9-anthracenecarboxylic acid was obtained, mp 169–170 C. rotation alpha (sodium D): 100.8 degrees (c=2.0, CHC13)

Analysis for C$_{16}$H$_{11}$ClO$_2$: Calculated: C, 70.99; H, 4.10 Found: C, 70.75; H, 4.18

1H NMR 7.48–7.64 (m, 2H), 7.27–7.36 (m, 1H), 7.23 (d, J=7.8 Hz, 1H), 6.90–7.12 (m, 3H), 4.36 (s, 1H), 2.80–2.95 (m, 2H)

EXAMPLE 2

1-(2-Chloro-9,10-dihydro-9,10-methanoanthracen-9-ylmethyl)-4-(6-quinolinyl)piperidin-4-ol Using a procedure similar to that described in example 1 except employing 7-bromoquinoline, the title compound was formed in 63% yield as a white solid, mp 210°–215° C. (dec). free base: 1H NMR (CDCl$_3$, 250 MHz) 8.87 (dd, J=1.6, 4.2 Hz, 1H), 8.14 (d, J=7.1Hz, 1H), 8.07 (d, J=8.9 Hz, 1H), 7.92 (d, J=1.9 Hz, 1H), 7.86 (dd, J=2.0, 8.8 Hz, 1H), 7.38 (dd, J=4.2, 8.3 Hz, 1H), 7.20 (m, 4H), 6.95 (m, 3H), 4.26 (s, 1H), 3.46 (s, 2H), 2.87 (m, 2H), 2.78 (m, 2H), 2.64 (d, J=1.4 Hz, 2H), 2.24 (m, 2H), 1.89 (s, 1H), 1.80 (m, 2H) MS (CI, CH4) m/z 467 (M+1,100), 469 (38), 495 (M+29, 19), 449 (15) hydrochloride salt:

Analysis for C$_{30}$H$_{27}$N$_2$OCl..2HCl.H$_2$O: Calculated: C, 64.58; H, 5.60; N, 5.02 Found: C, 64.18; H, 5.54; N, 4.87

EXAMPLE 3

1-(2-Chloro-9,10-dihydro-9,10-methanoanthracen-9-ylmethyl)-4-(3-quinolinyl)piperidin-4-ol Using a procedure similar to that described in example 1 except employing 3-bromoquinoline, the title compound was formed in 50% yield as a white solid, mp 215°–217° C. free base: 1H NMR (CDCl$_3$, 250 MHz) 9.07 (d, J=2.0 Hz, 1H), 8.21 (d, J=1.3 Hz, 1H), 8.09 (d, J=8.4 Hz, 1H), 7.80 (d, J=8.1Hz, 1H), 7.69 (dd, J=7.5, 7.6 Hz, 1H), 7.53 (dd, J=7.6, 6.8 Hz, 1H), 7.22 (m, 4H), 6.98 (m, 3H), 4.28 (s, 1H), 3.48 (s, 2H), 2.96 (m, 2H), 2.79 (m, 2H), 2.65 (s, 2H), 2.43 (m, 2H), 2.03 (s, 1H), 1.84 (m, 2H) MS (CI, CH4) m/z 467 (M+1,100), 495 (M+29,20), 449 (15), 469 (37) hydrochloride salt:

Analysis for C$_{30}$H$_{27}$N$_2$OCl.2HCl.H$_2$O: Calculated: C, 64.58; H, 5.60; N, 5.02 Found: C, 64.24; H, 5.49; N, 4.92

EXAMPLE 4

1-(2-Chloro-9,10-dihydro-9,10-methanoanthracen-9-ylmethyl)-4-(2-thiazyl)piperidin-4-ol Using a procedure similar to that described in example 1 except employing 2-bromothiazole, the title compound was formed in 78% yield as a white solid, mp 195°–199° C. (dec). free base: 1H NMR (CDCl$_3$, 300 MHz) 7.71 (d, J=3.2 Hz, 1H), 7.23 (m, 2H), 7.19 (m, 2H), 6.96 (m, 4H), 4.25 (br s, 1H), 3.43 (s, 2H), 2.89 (m, 2H), 2.76 (m, 2H), 2.60 (d, J=1.4 Hz, 2H), 2.25 (m, 2H), 1.88 (m, 2H) MS (CI, CH4) m/z 423 (M+1,100), 425 (43), 451 (M+29,10), 405 (17) hydrochloride salt:

Analysis for C$_{24}$H$_{23}$ClN$_2$OS.2HCl.0.5H$_2$O: Calculated: C, 57.09; H, 5.19; N, 5.55 Found: C, 56.94; H, 5.03; N, 5.23

EXAMPLE 5

1-(9,10-Dihydro-9,10-methanoanthracen-9-ylmethyl)-4-(3-pyridyl)piperidin-4-ol

Using a procedure similar to that described in example 1 except starting with 1-(9,10-dihydro-9,10-methanoanthracen-9-ylmethyl)-4-piperidinone, the title compound was formed in 66% yield as a white solid, mp 188°–190° C. (dec). free base: 1H NMR (D$_6$-DMSO, 300 MHz) 8.68 (d, J=2.2 Hz, 1H), 8.40 (dd, J=3.3 Hz, 1H), 7.84 (m, 1H), 7.28 (m, 5H), 6.92 (m, 4H), 5.03 (br s, 1H), 4.32 (br s, 1H), 3.31 (s, 2H), 2.79 (m, 2H), 2.70 (m, 2H), 1.91 (m, 2H), 1.60 (m, 2H) MS (CI, CH4) m/z 383 (M+1,100), 411 (M+29,13), 365 (17), 304 (11), 80 (16) hydrochloride salt:

Analysis for C$_{26}$H$_{26}$N$_2$O.2HCl.0.7H$_2$O: Calculated: C, 66.72; H, 6.33; N, 5.99 Found: C, 66.76; H, 6.60; N, 5.87

The starting piperidinone was prepared as follows:

a. 9,10-Dihydro-9,10-methano-9-anthracenecarboxylic acid

Using a procedure similar to that described in example 1j except starting with 9-formyl-9,10-dihydro-9,10- methanoanthracene (literature preparation: H. Sunagawa, et al; Chem. Pharm. Bull. Vol. 27 (1979) pp 1806–1812; U.S. Pat. No. 4,224,344 Sunagawa et al, Sumitomo, Ltd.; Sep. 23, 1980; U.S. Pat. No. 4,358,620 Sunagawa et al, Sumitomo, Ltd.; Nov. 9, 1982), the title compound was formed in 80% yield as a white solid. MS (CI, CH4) m/z 237 (M+1,100), 265 (M+29,10), 219 (22), 209 (15), 193 (20)

b. 1-(9,10-Dihydro-9,10-methanoanthracen-9-ylcarbonyl)piperidin-4-ol

Using a procedure similar to that described in example 1k except starting with 9,10-dihydro-9,10-methano-9-anthracenecarboxylic acid (described in example 5a), the title compound was formed in quantitative yield as a viscous oil. TLC analysis ($R_f$ 0.54, 10% methanol in chloroform). MS (CI, CH4) m/z 320 (M+1,100), 348 (M+29,22), 302 (16)

c. 1-(9,10-Dihydro-9,10-methanoanthracen-9-ylmethyl)piperidin-4-ol

Using a procedure similar to that described in example 1l except starting with 1-(9,10-dihydro-9,10-methanoanthracen-9-ylcarbonyl)piperidin-4-ol (described in example 5b), the title compound was formed in 88% yield as a white solid. TLC analysis ($R_f$ 0.59, 10% methanol in chloroform). MS (CI, CH4) m/z 306 (M+1,100), 334 (M+29,14), 288 (62), 114 (8)

d. 1-(9,10-Dihydro-9,10-methanoanthracen-9-ylmethyl)-4-piperidinone

Using a procedure similar to that described in example 1m except starting with 1-(9,10-dihydro-9,10-methanoanthracen-9-ylmethyl)piperidin-4-ol (described in example 5c), the title compound was formed in 801 yield as a white solid. TLC analysis ($R_f$ 0.31, 2% methanol in methylene chloride). MS (CI, CH4) m/z 304 (M+1,100), 332 (M+29,21)

EXAMPLE 6

1-(9,10-Dihydro-9,10-methanoanthracen-9-ylmethyl)-4-(3-furanyl)piperidin-4-ol

Using a procedure similar to that described in example 1 except starting with 1-(9,10-dihydro-9,10-methanoanthracen-9-ylmethyl)-4-piperidinone (described in example 5d) and employing 3-bromofuran, the title compound was formed in 71% yield as a white solid, mp 275°–276° C. (dec). free base: 1H NMR (CDCl$_3$, 300 MHz) 7.36 (m, 2H), 7.23 (dd, J=2.5, 5.6 Hz, 2H), 7.17 (dd, J=2.0, 5.4 Hz, 2H), 6.93 (m, 4H), 6.40 (m, 1H), 4.27 (s, 1H), 3.44 (s, 2H), 2.80 (m, 2H), 2.70 (dt, J=2.8, 11.2 Hz, 2H), 2.60 (d, J=1.5 Hz, 2H), 1.99 (dt, J=4.2, 12.1 Hz, 2H), 1.80 (m, 2H), 1.55 (s, 1H) MS (CI, CH4) m/z 372 (M+1,100), 400 (M+29,21), 354 (57), 180 (16) hydrochloride salt:

Analysis for C$_{25}$H$_{25}$NO$_2$.HCl.1H$_2$O: Calculated: C, 73.28; H, 6.44; N, 3.42 Found: C, 73.24; H, 6.49; N, 3.30

EXAMPLE 7

4-(5-Bromo-2-methoxy-3-pyridyl)-1-(9,10-dihydro-9,10-methanoanthracen-9-ylmethyl)piperidin-4-ol Using a procedure similar to that described in example 1 except starting with 1-(9,10-dihydro-9,10-methanoanthracen-9-ylmethyl)-4-piperidinone (described in example 5d) and employing 3,5-dibromo-2-methoxypyridine (literature preparation: J. M. Barger, J. K. Dulworth, M. T. Kenny, R. Massao, J. K. Daniel, T. Wilson, R. T. Sargent J. Med. Chem. 1986, 29, 1590), the title compound was formed in 63% yield as an off-white solid, mp 250°–251° C. (dec). free base: 1H NMR (CDCl$_3$, 300 MHz) 8.08 (d, J=2.3 Hz, 1H), 7.61 (d, J=2.3 Hz, 1H), 7.21 (m, 4H), 6.90 (m, 4H), 4.26 (s, 1H), 3.97 (s, 3 H), 3.56 (s, 1H), 3.47 (s, 2H), 2.86 (m, 2H), 2.77 (dt, J=2.6, 11.4 Hz, 2H), 2.60 (d, J=1.4 Hz, 2H), 1.96 (m, 4H) MS (CI, CH4) m/z 491 (M+1,100), 483 (89), 492 (37), 494 (26), 521 (M+29, 13), 473 (28) hydrochloride salt:

Analysis for C$_{27}$H$_{27}$BrN$_2$O$_2$.HCl: Calculated: C, 61.43; H, 5.35; N, 5.31 Found: C, 61.42; H, 5.42; N, 5.25

EXAMPLE 8

4-(5-Chloro-2-methoxy-3-pyridyl)-1-(9,10-dihydro-9,10-methanoanthracen-9-ylmethyl)piperidin-4-ol Using a procedure similar to that described in example 1 except starting with 1-(9,10-dihydro-9,10-methanoanthracen-9-ylmethyl)-4-piperidinone (described in example 5d) and employing 3-bromo-5-chloro-2-methoxypyridine, the title compound was formed in 25% yield as a white solid, mp 195–200 C, (dec). free base: 1H NMR (CDCl$_3$, 250 MHz) 7.99 (d, J=2.4 Hz, 1H), 7.50 (d, J=2.4 Hz, 1H), 7.20 (m, 4H), 6.93 (m, 4H), 4.27 (s, 1H), 3.99 (s, 3H), 3.58 (s, 1H), 3.47 (s, 2H), 2.82 (m, 4H), 2.60 (d, J=0.8 Hz, 2H), 2.00 (m, 4H) MS (CI, CH4) m/z 447 (M+1,100), 475 (M+29,18), 429 (34), 449 (36) hydrochloride salt:

Analysis for C$_{27}$H$_{27}$ClN$_2$O$_2$.HCl.0.6H$_2$O: Calculated: C, 65.61; H, 5.95; N, 5.67 Found: C, 65.48; H, 5.76; N, 5.58

The starting methoxypyridine derivative was prepared as follows:

a. 5-Chloro-2-methoxypyridine

Sodium hydride (60% in mineral oil, 5.50 g, 115 mmol, 2 eq) was added portionwise to dry methanol (distilled from Mg, 25 mL) under a nitrogen atmosphere. To this solution was added 2,5-dichloropyridine (10.0 g, 68 mmol). After refluxing the resulting solution for 18 h, the reaction was cooled and treated with excess solid potassium bicarbonate. The reaction was filtered and concentrated to 50% of its original volume upon which the solution solidified. The solids were washed with hexane and combined washes were concentrated to an oil. The title compound was purified by reduced pressure distillation (102° C., 2400 pascal) to yield 6.30 g (65%) of a colorless oil. HS (CI, CH4) m/z 144 (M+,100), 146 (44), 172 (M+28,19), 124 (9)

b. 3-Bromo-5-chloro-2-methoxypyridine

Using a procedure similar to that described in example 7 except starting with 5-chloro-2-methoxy pyridine (described in example 8a), the title compound was obtained in 41% yield. MS (CI,CH4) 222 (M+1,74), 224 (100), 226 (24), 250 (5), 252 (6), 254 (1)

EXAMPLE 9

1-(9,10-Dihydro-9,10-methanoanthracen-9-ylmethyl)-4-(3-quinolinyl)piperidin-4-ol Using a procedure similar to that described in example 1 except starting with 1-(9,10-dihydro-9,10-methanoanthracen-9-ylmethyl)-4-piperidinone (described in example 5d) and employing 3-bromoquinoline, the title compound was formed in 44% yield as a white solid, mp 205°–207° C. free base: 1H NMR (CDCl$_3$, 300 MHz) 9.06 (d, J=3.6 Hz, 1H), 8.20 (d, J=3.0 Hz, 1H), 8.08 (d, J=8.1Hz, 1H), 7.80 (d, J=8.1Hz, 1H), 7.68 (dd, J=6.0, 5.9 Hz, 1H), 7.54 (dd, J=8.5, 9.0 Hz, 1H), 7.23 (m, 4H), 6.94 (m, 4H), 4.30 (s, 1H), 3.52 (s, 2H), 2.98 (m, 2H), 2.78 (m, 2H), 2.64 (d, J=1.4 Hz, 2H), 2.24 (dt, J=3.9, 11.6 Hz, 2H), 1.99 (s, 1H), 1.83 (m, 2H) MS (CI, CH4) m/z 433 (M+1.17), 415 (4), 211 (12), 89 (100), 79 (45), 73 (13) hydrochloride salt:

Analysis for $C_{30}H_{28}N_2O\cdot 2HCl/2.5H_2O$: Calculated: C, 65.45; H, 6.41; N, 5.09 Found: C, 65.47; H, 5.93; N, 4.94

EXAMPLE 10

4-(4-Isoquinolinyl)-1-(9,10-dihydro-9,10-methanoanthracen-9-ylmethyl)piperidin-4-ol Using a procedure similar to that described in example 1 except starting with 1-(9,10-dihydro-9,10-methanoanthracen-9-ylmethyl)-4-piperidinone (described in example 5d) and employing 4-bromo-isoquinoline, the title compound was formed in 53% yield as a white solid, mp 256°–259° C. (dec). free base: 1H NMR (CDCl$_3$, 250 MHz) 9.10 (s, 1H), 8.82 (d, J=7.5 Hz, 1H), 8.50 (s, 1H), 7.95 (d, J=8.0 Hz, 1H), 7.67 (m, 1H), 7.58 (m, 1H), 7.26 (m, 4H), 6.94 (m, 4H), 4.29 (s, 1H), 3.53 (s, 2H), 2.91 (m, 4H), 2.64 (d, J=1.3 Hz, 2H), 2.28 (m, 4H) MS (CI, CH4) m/z 433 (M+1,100), 461 (M+29,14), 415 (26), 123 (12) hydrochloride salt:

Analysis for $C_{30}H_{28}N_2O\cdot 2.5H_2O$: Calculated: C, 66.50; H, 6.05; N, 5.12 Found: C, 66.37; H, 5.89; N, 5.03

EXAMPLE 11

1-(9,10-Dihydro-9,10-methanoanthracen-9-ylmethyl)-4-(2-methoxy-5-pyridyl)piperidin-4-ol Using a procedure similar to that described in example 1 except starting with 1-(9,10-dihydro-9,10-methanoanthracen-9-ylmethyl)-4-piperidinone (described in example 5d) and employing 5-bromo-2-methoxypyridine, the title compound was formed in 81% yield as a white solid, mp 218°–222° C. free base: 1H NMR (CDCl$_3$, 250 MHz) 8.28 (d, J=2.5 Hz, 1H), 7.69 (dd, J=2.6, 8.7 Hz, 1H), 7.22 (m, 4H), 6.95 (m, 4H), 6.71 (d, J=8.7 Hz, 1H), 4.28 (s, 1H), 3.93 (s, 3H), 3.48 (s, 2H), 2.91 (m, 2H), 2.78 (dt, J=2.4, 11.7 Hz, 2H), 2.62 (d, J=1.4 Hz, 2H), 2.07 (dt, J=4.4, 12.8 Hz, 2H), 1.75 (m, 2H), 1.59 (s, 1H) MS (CI, CH4) m/z 413 (M+1, 100), 441 (M+29,12), 395 (19) hydrochloride salt: Analysis for $C_{27}H_{28}N_2O_2\cdot 2HCl\cdot 0.5H_2O$: Calculated: C, 65.59; H, 6.32; N, 5.67 Found: C, 65.48; H, 6.14; N, 5.35

The starting methoxypyridine derivative was prepared as follows:

a. 5-Bromo-2-methoxypyridine

Using a procedure similar to that described in example 8a except starting with 2,5-dibromopyridine, the title compound was obtained in 73% yield. MS (CI, CH4) m/z 188 (M+1,90), 190 (100), 216 (16), 218 (15), 137 (27), 110 (35)

EXAMPLE 12

1-(9,10-Dihydro-9,10-methanoanthracen-9-ylmethyl)-4-(5-pyrimidinyl)piperidin-4-ol Using a procedure similar to that described in example 1 except starting with-(9,10-dihydro-9,10-methanoanthracen-9-ylmethyl)-4-piperidinone (described in example 5d) and employing 5-bromopyrimidine, the title compound was formed in 60% yield as a white solid, mp 298°–300° C. (dec). free base: 1H NMR (CDCl$_3$, 250 MHz) 9.12 (s, 1H), 8.86 (s, 2H), 7.26 (m, 2H), 7.18 (m, 2H), 6.94 (m, 4H), 4.29 (s, 1H), 3.49 (s, 2H), 2.96 (m, 2H), 2.70 (dt, J=2.5, 12.0 Hz, 2H), 2.61 (d, J=1.5 Hz, 2H), 2.10 (dt, J=4.6, 13.0 Hz, 2H), 1.89 (s, 1H), 1.76 (m, 2H) MS (CI, CH4) m/z 384 (M+1, 100), 412 (M+29,20), 366 (13) hydrochloride salt:

Analysis for $C_{25}H_{25}N_3O\cdot HCl\cdot 0.4H_2O$: Calculated: C, 70.30; H, 6.32; N, 9.84 Found: C, 70.33; H, 6.21; N, 9.77

EXAMPLE 13

1-(9,10-Dihydro-9,10-methanoanthracen-9-ylmethyl)-4-(6-methoxy-2-pyridyl)piperidin-4-ol Using a procedure similar to that described in example 1 except starting with 1-(9,10-dihydro-9,10-methanoanthracen-9-ylmethyl)-4-piperidinone (described in example 5d) and employing 2-bromo-6-methoxypyridine, the title compound was formed in 98% yield [ ] as a white solid, mp 193°–195° C. (dec). free base: 1H NMR (CDCl$_3$, 300 MHz) 7.57 (dd, J=7.6, 7.6 Hz, 1H), 7.23 (m, 4H), 6.94 (m, 5H), 6.63 (d, J=8.0 Hz, 1H), 4.75 (s, 1H), 4.28 (s, 1H), 3.95 (s, 3H), 3.49 (s, 2H), 2.94 (m, 2H), 2.77 (m, 2H), 2.64 (d, J=1.2 Hz, 2H), 2.04 (m, 2H), 1.63 (m, 2H) MS (CI, CH4) m/z 413 (M+1,100), 441 (M+29,12), 395 (18) hydrochloride salt:

Analysis for $C_{27}H_{28}N_2O_2\cdot HCl\cdot 0.6H_2O$: Calculated: C, 70.53; H, 6.62; N, 6.09 Found: C, 70.22; H, 6.46; N, 6.04

EXAMPLE 14

1-(9,10-Dihydro-9,10-methanoanthracen-9-ylmethyl)-4-(2-thiazyl)piperidin-4-ol

Using a procedure similar to that described in example 1 except starting with 1-(9,10-dihydro-9,10-methanoanthracen-9-ylmethyl)-4-piperidinone (described in example 5d) and employing 2-bromothiazole, the title compound was formed in 77% yield as an off-white solid, mp 200°–202° C. (dec). free base: 1H NMR (CDCl$_3$, 300 MHz) 7.70 (d, J=3.2 Hz, 1H), 7.23 (m 5H), 6.94 (m, 4H), 4.26 (br s, 1H), 3.48 (s, 2H), 2.92 (m, 2H), 2.75 (m, 2H), 2.61 (d, J=1.3 Hz, 2H), 2.23 (m, 2H), 1.85 (m, 2H) MS (CI, CH4) m/z 389 (M+1,100), 371 (8) hydrochloride salt:

Analysis for $C_{24}H_{24}N2OS\cdot 2HCl$: Calculated: C, 62.47; H, 5.68; N, 6.07 Found: C, 62.58; H, 5.87; N, 5.76

EXAMPLE 15

1-(9,10-Dihydro-9,10-methanoanthracen-9-ylmethyl)-4-(3-thienyl)piperidin-4-ol

Using a procedure similar to that described in example 1 except starting with 1-(9,10-dihydro-9,10-methanoanthracen-9-ylmethyl)-4-piperidinone (described in example 5d) and employing 3-bromothiophene, the title compound was formed in 81% yield as an off-white solid, mp 273°–277° C. (dec). free base: 1H NMR (CDCl$_3$, 250 MHz) 7.17 (m, 7H), 6.94 (m, 4H), 4.26 (s, 1H), 3.46 (s, 1H), 2.84 (m, 2H), 2.71 (m, 2H), 2.60 (d, J=1.4 Hz, 2H), 2.12 (m, 2H), 1.83 (m, 2H) MS (CI, CH4) m/z 388 (M+1,100), 416 (M+29,20), 370 (51), 304 (10), 196 (12) hydrochloride salt:

Analysis for $C_{25}H_{25}NOS\cdot 1.6HCl\cdot H_2O$: Calculated: C, 64.73; H, 6.21; N, 3.02 Found: C, 64.72; H, 5.86; N, 2.93

EXAMPLE 16

1-(9,10-Dihydro-9,10-methanoanthracen-9-ylmethyl)-4-(2-Pyridyl)piperidin-4-ol

Using a procedure similar to that described in example 1 except starting with 1-(9,10-dihydro-9,10-methanoanthracen-9-ylmethyl)-4-piperidinone (described in example 5d) and 2-bromopyridine, the title compound was formed in 66% yield as a white solid, mp 194°–196° C. free base: 1H NMR (CDCl$_3$, 250 HHz) 8.53 (d, J=5.0 Hz, 1H), 7.70 (ddd, J=1.5, 7.7, 7.7 Hz, 1H), 7.39 (d, J=7.8 Hz, 1H), 7.22 (m, 5H), 6.94 (m, 4H), 5.23 (s, 1H), 4.30 (s, 1H), 3.52 (s, 2H), 2.99 (m, 2H), 2.81 (dt, J=2.0, 12.0 Hz, 2H), 2.65 (d, J=2.0 Hz, 2H), 2.07 (dt, J=5.0, 13.0 Hz, 2H), 1.60 (m, 2H) MS (CI, CH4) m/z 383 (M+1,100), 411 (M+29,20), 365 (18), 364 (17) hydrochloride salt: Analysis for $C_{26}H_{26}N_2O\cdot 2HCl\cdot 0.1H_2O$: Calculated: C, 68.30; H, 6.22; N, 6.13 Found: C, 68.17; H, 6.21; N, 6.09

EXAMPLE 17

1-(9,10-Dihydro-9,10-methanoanthracen-9-ylmethyl)-4-(3-methoxyphenyl)piperidin-4-ol Using a procedure similar to that described in example 1 except starting with 1-(9,10-dihydro-9,10- methanoanthracen-9-ylmethyl)-4-piperidinone (described in example 5d) and employing 3-bromoanisole, the hydrochloride salt of the title compound was formed in 59% yield as a white solid, mp 260–261 C. elemental Analysis for $C_{28}H_{29}NO_2 \cdot HCl \cdot 0.4H_2O$: Calculated: C, 73.88; H, 6.82; N, 3.08 Found: C, 73.87; H, 6.70; N, 3.14

1H NMR ($D_6$-DMSO, D-TFA): 7.39 (m, 5H), 7.03 (m, 6H), 6.66 (m, 1H), 4.50 (s, 3H), 3.77 (s, 3H), 3.64 (m, 4H), 2.76 (s, 2H), 2.39 (m, 2H), 1.81 (d, J=13.9 Hz, 2H) MS (CI, CH4) m/z 413 (31), 412 (M+1,100), 411 (11), 394 (26)

EXAMPLE 18

1-(9,10-Dihydro-9,10-methanoanthracen-9-ylmethyl)-4-(4-methoxyphenyl)piperidin-4-ol Using a procedure similar to that described in example except starting with 1-(9,10-dihydro-9,10-methanoanthracen-9-ylmethyl)-4-piperidinone (described in example 5d) and employing 4-bromoanisole, the hydrochloride salt of the title compound was formed in 72% yield as a white solid, mp 228°–231° C. elemental Analysis for $C_{28}H_{29}NO_2 \cdot HCl$: Calculated: C, 75.07; H, 6.75; N, 3.13 Found: C, 74.93; H, 6.74; N, 3.14

1H NMR ($D_6$-DMSO, D-TFA): 7.39 (m, 6H), 7.02 (m, 4H), 6.94 (d, J=8.8 Hz, 2H), 4.48 (s, 3H), 3.74 (s, 3H), 3.68–3.52 (m, 4H), 2.76 (s, 2H), 2.35 (m, 2H), 1.81 (d, J=13.9 Hz, 2H) MS (CI, CH4) m/z 413 (33), 412 (M+1,100), 411 (15), 394 (51)

EXAMPLE 19

1-(9,10-Dihydro-9,10-methanoanthracen-9-ylmethyl)-4-(2-methoxyphenyl)piperidin-4-ol Using a procedure similar to that described in example 1 except starting with 1-(9,10-dihydro-9,10-methanoanthracen-9-ylmethyl)-4-piperidinone (described in example 5d) and employing 2-bromoanisole, the hydrochloride salt of the title compound was formed in 43% yield as a white solid, mp 290–293 C. elemental Analysis for $C_{28}H_{29}NO_2 \cdot HCl \cdot 0.3H_2O$: Calculated: C, 74.17; H, 6.80; N, 3.08 Found: C, 74.01; H, 6.83; N, 3.04

1H NMR ($D_6$-DMSO, D-TFA): 7.56 (d, J=6.5 Hz, 1H), 7.43–7.24 (m, 5H), 7.02 (m, 6H), 4.48 (s, 3H), 3.82 (s, 3H), 3.65 (m, 2H), 3.46 (m, 2H), 2.72 (s, 2H), 2.72 (m, 2H), 1.73 (d, J=13.6 Hz, 2H).

EXAMPLE 20

1-(9,10-Dihydro-9,10-methanoanthracen-9-ylmethyl)-4-(2-dimethylamino-methylphenyl)piperidin-4-ol Using a procedure similar to that described in example 1 except starting with 1-(9,10-dihydro-9,10-methanoanthracen-9-ylmethyl)-4-piperidinone (described in example 5d) and employing 2-bromo-N,N-dimethylbenzylamine, the hydrochloride salt of the title compound was formed in 36% yield as a white solid, mp 230°–235° C. elemental Analysis for $C_{30}H_{34}N_2O \cdot 2.0HCl \cdot 1.1H_2O$: Calculated: C, 67.81; H, 7.25; N, 5.27 Found: C, 67.83; H, 7.85; N, 5.04

1H NMR ($D_6$-DMSO, D-TFA): 7.41 (m, 8H), 7.02 (m, 4H), 4.61 (s, 2H), 4.52 (s, 2H), 4.50 (s, 1H), 3.73 (m, 2H), 3.58 (m, 2H), 2.82 (s, 6H), 2.76 (s, 2H), 2.52 (m, 2H), 2.12 (d, J=14.1Hz, 2H) MS (CI,CH4) m/z 440 (36), 439 (M+1, 100), 438 (15)

EXAMPLE 21

1-(9,10-Dihydro-9,10-methanoanthracen-9-ylmethyl)-4-phenylpiperidine

To a methanol solution (80 mL) of 9-formyl-9,10-dihydro-9,10-methanoanthracene (described in example 5a) (5.00 g, 22.7 mmol) was added a large excess of freshly activated 3 A molecular sieves (approx. 10 g) under an atmosphere of nitrogen. 4-Phenylpiperidine (4.57 g, 28 mmol, 1.25 eq) was added followed by four portions of sodium cyanoborohydride (1.43 g, 22.7 mmol) over 1.3 h. The resulting suspension of sieves and reagents was stirred for 3 days at room temperature. The reaction was treated with 2.5N NaOH (100 mL) and the aqueous phase was extracted with ethyl acetate (1×400 mL). The organic phase was washed with water (3×100 mL), dried over anhydrous sodium sulfate, filtered and reduced to an oil. The reaction product was purified by flash chromatography over silica gel (300 mL, eluent: 50% methylene chloride in hexane) to recover 1.20 g (15%) of the title compound. TLC analysis ($R_f$ 0.19, 50% methylene chloride in hexane). 1H NMR (CDCl$_3$, 300 MHz) 7.22 (m, 9H), 6.93 (m, 4H), 4.27 (s, 1H), 3.43 (s, 2H), 3.13 (m, 2H), 2.62 (d, J=1.4 Hz, 2H), 2.51 (m, 1H), 2.34 (m, 2H), 1.76 (m, 4H) MS (CI, CH4) m/z 366 (M+1,100), 394 (M+29,16) The free base was dissolved in the minimum of methanol and chloroform, acidified with ethereal HCl and the resulting hydrochloride salt precipitated with ether dilution. The solid was filtered, rinsed with fresh ether, and dried in vacuo (50° C., 10 pascal, 18 h) to yield a solid, mp>300° C.

Analysis for $C_{27}H_{27}N \cdot HCl \cdot 0.5H_2O$: Calculated: C, 78.91; H, 7.11; N, 3.41 Found: C, 78.91; H, 6.92; N, 3.38

EXAMPLE 22

1-(9,10-Dihydro-9,10-methanoanthracen-9-ylmethyl)-4-(4-chlorophenyl)piperidin-4-ol Using a procedure similar to that described in example 21 except employing 4-(4-chlorophenyl)-4-hydroxypiperidine, the title compound hydrochloride salt was obtained in 19% yield as a white powder, mp 281°–285° C. elemental Analysis for $C_{27}H_{26}ClNO \cdot HCl \cdot 0.25H_2O$: Calculated: C, 70.97; H, 6.06; N, 3.06 Found: C, 71.28; H, 6.03; N, 3.02

1H NMR ($D_6$-DMSO, D-TFA): 7.51–7.35 (m, 8H), 7.01 (m, 4H), 4.50 (s, 3H), 3.72–3.59 (m, 4H), 2.76 (s, 2H), 2.38 (m, 2H), 1.83 (d, J=14.3 Hz, 2H) MS (CI, CH4) m/z 418 (37), 417 (35), 416 (M+1,100), 400 (16), (13), 398 (42).

EXAMPLE 23

1-(9,10-Dihydro-9,10-methanoanthracen-9-ylmethyl)-4-phenylpiperidin-4-ol

Using a procedure similar to that described in example 21 except employing 4-hydroxy-4-phenylpiperidine, the title compound hydrochloride salt was obtained in 181 yield as a white powder, mp 273°–275° C. elemental Analysis for $C_{27}H_{27}NO \cdot HCl$: Calculated: C, 77.58; H, 6.75; N, 3.35 Found: C, 77.51; H, 6.79; N, 3.32

1H NMR ($D_6$-DMSO, D-TFA): 7.72–7.23 (m, 9H), 7.01 (m, 4H), 4.49 (s, 3H), 3.64 (m, 4H), 2.76 (s, 2H), 2.50 (m, 2H), 1.82 (d, J=13.9 Hz, 2H) MS (CI, CH4) m/z 383 (30), 382 (M+1, 100), 381 (14), 380 (14), 364 (25).

EXAMPLE 24

1-(9,10-Dihydro-9,10-methanoanthracen-9-ylmethyl)-4-(3-trifluoromethylphenyl)piperidin-4-ol Using a procedure similar to that described in example 21 except employing 4-hydroxy-4-(3-trifluoromethylpbenyl)

piperidine, the title compound hydrochloride salt was obtained in 44% yield as a white powder, mp 268°–270° C. elemental Analysis for $C_{28}H_{26}F_3NO \cdot HCl \cdot 0.25H_2O$ Calculated: C, 68.56; H, 5.65; N, 2.86 Found: C, 68.74; H, 5.63; N, 2.81

1H NMR ($D_6$-DMSO, D-TFA): 7.80 (m, 2H), 7.63 (m, 2H), 7.40 (m, 4H), 7.01 (m, 4H), 4.53 (s, 2H), 4.50 (s, 1H), 3.70–3.61 (m, 4H), 2.78 (s, 2H), 2.47 (m, 2H), 1.85 (d, J=13.7 Hz, 2H) MS (CI, CH4) m/z 451 (31), 450 (M+1,100), 449 (17), 448 (16), 433 (19), 432 (66), 431 (25), 430 (78).

EXAMPLE 25

1-(9,10-Dihydro-9,10-methanoanthracen-9-ylmethyl)-4-(4-fluorophenyl)piperidin-4-ol Using a procedure similar to that described in example 21 except employing 4-(4-fluorophenyl)-4-hydroxypiperidine, the title compound hydrochloride salt was obtained in 26% yield as a white powder, mp 262°–266° C. elemental Analysis for $C_{27}H_{26}FNO \cdot HCl$: Calculated: C, 74.38; H, 6.24; N, 3.21 found: C, 74.41; H, 6.24; N, 3.17

1H NMR ($D_6$-DMSO, D-TFA): 7.51 (m, 2H), 7.37 (m, 4H), 7.21 (m, 2H), 7.02 (m, 4H), 4.49 (s, 3H), 3.62 (m, 4H), 2.76 (s, 2H), 2.41 (m, 2H), 1.82 (d, J=14.2 Hz, 2H) MS (CI, CH4) m/z 401 (26), 400 (M+1,100), 398 (15), 382 (33), 380 (17)

EXAMPLE 26

1-(2-Chloro-9,10-dihydro-9,10-methanoanthracen-9-ylmethyl)-4-(4-chlorophenyl)piperidin-4-ol Using a procedure similar to that described in example 21 except starting with 2-chloro-9-formyl-9,10-dihydro-9,10-methanoanthracene (described in example 1i) and 4-(4-chlorophenyl)-4-hydroxypiperidine, the title compound hydrochloride salt was obtained in 29% yield as a white powder, mp 261°–263° C. elemental Analysis for $C_{27}H_{25}Cl_2NO \cdot HCl$: Calculated: C, 66.61; H, 5.38; N, 2.87 Found: C, 66.41; H, 5.44; N, 2.80

1H NMR ($D_6$-DMSO, D-TFA): 7.58 (d, J=1.8 Hz), 7.54–7.34 (m, 7H), 7.02 (m, 3H), 4.52 (s, 1H), 4.50 (qAB, JAB=13.7 Hz, 2H), 3.70–3.51 (m, 4H), 2.78 (qAB, JAB=9.0 Hz, 2H), 2.39 (m, 2H), 1.83 (d, J=14.3 Hz, 2H) MS (CI, CH4) m/z 454 (10), 453 (16), 452 (54), 451 (30), 450 (M+1,100), 435 (13), 434 (47), 433 (24), 432 (86), 289 (24), 97 (46), 79 (99)

EXAMPLE 27

1-(2-Chloro-9,10-dihydro-9,10-methanoanthracen-9-ylmethyl)-4-(4-fluorophenyl)piperidin-4-ol Using a procedure similar to that described in example 21 except starting with 2-chloro-9-formyl-9,10-dihydro-9,10-methanoanthracene (described in example 1i) and 4-(4-fluorophenyl)-4-hydroxypiperidine, the title compound hydrochloride salt was obtained in 27% yield as a white powder, mp 280°–281° C. elemental Analysis for $C_{27}H_{25}ClFNO \cdot HCl \cdot 0.5H_2O$: Calculated: C, 67.64; H, 5.68; N, 2.92 Found: C, 67.70; H, 5.40; N, 2.84

1H NMR ($D_6$-DMSO, D-TFA): 7.57 (d, J=1.8 Hz, 1H), 7.54–7.35 (m, 5H), 7.19 (t, J=8.9 Hz, 2H), 7.03 (m, 3H), 4.52 (s, 1H), 4.52 (qAB, JAB=14.1 Hz, 2H), 3.70–3.53 (m, 4H), 2.77 (qAB, JAB=6.8 Hz, 2H), 2.34 (m, 2H), 1.84 (d, J=14.0 Hz, 2H) MS (CI, CH4) m/z 437 (10), 436 (37), 435 (33), 434 (M+1,100), 418 (18), 417 (15), 416 (50)

EXAMPLE 28

1-(2-Chloro-9,10-dihydro-9,10-methanoanthracen-9-ylmethyl)-4-phenylpiperidin-4-ol Using a procedure similar to that described in example 21 except starting with 2-chloro-9-formyl-9,10-dihydro-9,10-methanoanthracene (described in example 1i) and 4-hydroxy-4-phenylpiperidine, the title compound hydrochloride salt was obtained in 32% yield as a white powder, mp 260°–261° C. elemental Analysis for $C_{27}H_{26}ClNO \cdot HCl \cdot 0.1H_2O$: Calculated: C, 71.40; H, 6.04; N, 3.09 Found: C, 71.20; H, 6.02; N, 3.00

1H NMR ($D_6$-DMSO, D-TFA): 7.58 (s, 1H), 7.52–7.25 (m, 6H), 7.05 (m, 3H), 4.53 (qAB, JAB=14.2 Hz, 2H), 4.52 (s, 1H), 3.75–3.56 (m, 4H), 2.77 (m, 2H), 2.39 (m, 2H), 1.86 (d, J=14.4 Hz, 2H) MS (CI, CH4) m/z 419 (10), 418 (38), 417 (34), 416 (M+1,100), 400 (12), 398 (33)

EXAMPLE 29

4-(2-Biphenyl)-1-(9,10-dihydro-9,10-methanoanthracen-9-ylmethyl)piperidin-4-ol To a cooled (−72° C.) solution of t-butyllithium (1.7M in pentane, 3.00 mL, 5.12 mmol) in tetrahydrofuran (4.0 mL) was added dropwise 2-bromobiphenyl (0.49 g, 2.12 mmol, 1.6 eq) in tetrahydrofuran (2 mL). The resulting solution was stirred for 2 h under a nitrogen atmosphere. A solution of 1-(9,10-dihydro-9,10-methanoanthracen-9-ylmethyl)-4-piperidinone (described in example 5d) (0.40 g, 1.3 mmol) in tetrahydrofuran (4 mL) was added dropwise to the lithiobiphenyl and the reaction was then allowed to warm to room temperature over 45 min. Stirring was continued at room temperature for 3 h. Excess reagent was quenched with water (10 mL) and the aqueous phase extracted with ethyl acetate (2×100 mL). The combined organic extracts were washed with water (2×100 mL), dried over anhydrous sodium sulfate, filtered, and reduced to a solid. The reaction product was purified by flash chromatography over silica gel (65 mL, eluent: 20% diethyl ether in hexane) to yield 0.43 g (72%) of the title compound as a white solid. TLC analysis ($R_f$ 0.23, 20% diethyl ether in hexane). 1H NMR (CDCl$_3$, 250 MHz) 7.50 (m, 1H), 7.32 (m, 6H), 7.25 (m, 3H), 7.14 (m, 2H), 7.06 (dd, J=1.1, 7.5 Hz, 1H), 6.91 (m, 4H), 4.24 (s, 1H), 3.56 (s, 2H), 2.75 (m, 2H), 2.55 (d, J=1.4 Hz, 2H), 2.56 (m, 2H), 2.13 (dt, J=4.5, 13.2, 12.3 Hz, 2H), 1.72 (m, 2H), 1.52 (s, 1H) MS (CI, CH4) m/z 458 (M+1,100), 486 (M+29,35), 440 (14), 304 (6) The hydrochloride salt was formed by treating an ether solution of the free base with excess ethereal HCl. The resulting solid was filtered, rinsed with fresh ether, and dried in vacuo (50° C., 10 pascal, 18 h).to yield a white solid, mp 269°–270° C.

Analysis for $C_{33}H_{31}NO \cdot HCl \cdot 0.75H_2O$: Calculated: C, 78.09; H, 6.65; N, 2.76 Found: C, 77.98; H, 6.49; N, 2.70

EXAMPLE 30

4-(4-Biphenyl)-1-(9,10-dihydro-9,10-methanoanthracen-9-ylmethyl)piperidin

Using a procedure similar to that described in example 29 except employing 4-bromobiphenyl, the title compound was obtained in 70% yield as a white solid, mp 262°–263° C. (dec). free base: 1H NMR (CDCl$_3$, 250 MHz) 7.60 (m, 1H), 7.57 (s, 5H), 7.42 (m,2H), 7.34 (m, 1H), 7.23 (m, 4H), 6.94 (m, 4H), 4.28 (s, 1H), 3.49 (s, 2H), 3.00 (m, 2H), 2.74 (m, 2H), 2.64 (d, J=1.3 Hz, 2H), 2.16 (m, 2H), 1.75 (m, 2H), 1.63 (s, 1H) MS (CI, CH4) m/z 458 (M+1,100), 486 (M+29,18), 440 (39), 441 (14), 304 (13) hydrochloride salt: elemental Analysis for $C_{33}H_{31}NO \cdot HCl \cdot 0.1H_2O$: Calculated: C, 79.43; H, 6.71; N, 2.89 Found: C, 79.42; H, 6.63; N, 2.79

EXAMPLE 31

4-(3-Biphenyl)-1-(9,10-dihydro-9,10-methanoanthracen-9-ylmethyl)piperidin-4-ol Using a procedure similar to that described in example 29 except employing 3-bromobiphenyl, the title compound was obtained in 64% yield as a white solid, mp 259°–260 C. free base: 1H NMR (CDCl$_3$, 250 MHz) 7.72 (m, 1H), 7.58 (m, 2H), 7.43 (m, 5H), 7.22 (m, 5H), 6.94 (m, 4H), 4.27 (s, 1H), 3.49 (s, 2H), 2.93 (m, 2H), 2.74 (dt, J=2.4, 11.9 Hz, 2H), 2.63 (d, J=1.4 Hz, 2H), 2.18 (dt, J=4.8, 12.3 Hz, 2H), 1.76 (m, 2H), 1.64 (s, 1H) MS (CI, CH4) m/z 458 (M+1,100), 486 (M+29,15), 440 (19) hydrochloride salt:

Analysis for $C_{33}H_{31}NO \cdot HCl \cdot 0.25H_2O$: Calculated: C, 79.50; H, 6.57; N, 2.81 Found: C, 79.35; H, 6.45; N, 2.77

EXAMPLE 32

1-(9,10-Dihydro-9,10-methanoanthracen-9-ylmethyl)-4-(2-methoxy-3-pyridyl)piperidin-4-ol To a cooled solution (−72° C.) of t-butyllithium (1.7M in pentane, 5.38 mL, 9.15 mmol, 2.8 eq) in tetrahydrofuran (24 mL) under nitrogen was added dropwise bromomesitylene (0.64 mL, 4.18 mmol, 1.3 eq). The metal-halogen exchange reaction was stirred for an additional hour during which time a white precipitate forms. 2-Methoxypyridine (0.50 g, 4.38 mmol, 1.4 eq) was added to this suspension and the resulting reaction was warmed to room temperature and stirred at that temperature for 4 h. The metallated pyridine solution was recooled to −72° C. and a solution of 1-(9,10-dihydro-9,10-methanoanthracen-9-ylmethyl)-4-piperidinone (described in example 5d) (1.00 g, 3.3 mmol) in tetrahydrofuran (3 mL) was added. The reaction was warmed to room temperature over 1.5 h. After stirring for 18 h, the reaction was quenched with the addition of water (10 mL). The aqueous phase was extracted with ethyl acetate (200 mL). The organic extract was washed with water (2×100 mL), dried with anhydrous sodium sulfate, filtered, and reduced to an oil. The product was purified by flash chromatography over silica gel (100 mL, eluent: 30% ethyl acetate in hexane) to yield 0.99 g (73%) of the title compound as a white solid. TLC analysis (R$_f$ 0.23, 30% ethyl acetate in hexane). 1H NMR (CDCl$_3$, 300 MHz) 8.05 (dd, J=4.9, 1.7 Hz, 1H), 7.49 (dd, J=7.5, 5.7 Hz, 1H), 7.22 (m, 4H), 6.92 (m, 5H), 4.27 (s, 1H), 4.02 (s, 3H), 3.78 (s, 1H), 3.48 (s, 2H), 2.83 (m, 4H), 2.61 (d, J=1.4 Hz, 2H), 2.00 (m, 4H) MS (CI, CH4) m/z 413 (M+1,100), 441 (M+29,13), 395 (24). The free base was dissolved in methylene chloride, diluted with ether and acidified with ethereal HCl. The resulting hydrochloride salt was filtered, rinsed with fresh ether, and dried in vacuo (50° C., 10 pascal, 18 h) to yield a white solid, mp 225°–228° C. (dec).

Analysis for $C_{27}H_{28}N_2O_2 \cdot HCl \cdot 0.2H_2O$: Calculated: C, 71.65; H, 6.55; N, 6.19 Found: C, 71.43; H, 6.46; N, 5.84

EXAMPLE 33

1-(9,10-Dihydro-9,10-methanoanthracen-9-ylmethyl)-4-(4-methoxy-3-pyridyl)piperidin-4-ol Using a procedure similar to that described in example 32 except starting with 4-methoxypyridine, the title compound was obtained in 72% yield as a white solid, mp 207°–210° C. (dec). free base: 1H NMR (CDCl$_3$, 300 MHz) 8.43 (s, 1H), 8.42 (d, J=5.1 Hz, 1H), 7.23 (m, 4H), 6.93 (m, 4H), 6.82 (d, J=5.7 Hz, 1H), 4.27 (s, 1H), 3.92 (s, 3H), 3.48 (s, 2H), 3.43 (s, 1H), 2.84 (m, 4H), 2.62 (d, J=1.4 Hz, 2H), 2.13 (dt, J=4.9, 12.4 Hz, 2H), 1.98 (m, 2H) MS (CI, CH4) m/z 413 (M+1,100), 441 (M+29,12), 395 (14) hydrochloride salt:

Analysis for $C_{27}H_{28}N_2O_2 \cdot 2HCl \cdot 1.5H_2O$: Calculated: C, 63.88; H, 6.49; N, 5.47 Found: C, 62.92; H, 6.20; N, 5.43

EXAMPLE 34

1-(2-Chloro-9,10-dihydro-9,10-methanoanthracen-9-ylmethyl)-4-(2-methoxy-3-pyridyl)piperidin-4-ol Using a procedure similar to that described in example 32 except starting with 1-(2-chloro-9,10-dihydro-9,10-methanoanthracen-9-ylmethyl)-4-piperidinone (described in example 1m), the title compound was obtained in 85% yield as a white solid, mp 195°–200° C. free base: 1H NMR (CDCl$_3$, 250 MHz) 8.05 (dd, J=1.6, 4.9 Hz, 1H), 7.51 (dd, J=7.4, 1.7 Hz, 1H), 7.20 (m, 4H), 6.96 (m, 2H), 6.88 (m, 2H), 4.25 (s, 1H), 4.03 (s, 3H), 3.77 (s, 1H), 3.43 (s, 2H), 2.82 (m, 4H), 2.61 (d, J=1.1 Hz, 2H), 1.99 (m, 4H) MS (CI, CH4) m/z 447 (M+1,100), 475 (M+29,15), 429 (27), 449 (37) hydrochloride salt:

Analysis for $C_{27}H_{27}N_2O_2Cl$: Calculated: C, 64.64; M, 5.73; N, 5.58 Found: C, 64.66; H, 5.66; N, 5.34

EXAMPLE 35

1-(2,7-Dichloro-9,10-dihydro-9,10-methanoanthracen-9-ylmethyl)-4-(2-methoxy-3-pyridyl)piperidin-4-ol Using a procedure similar to that described in example 32 except starting with 1-(2,7-dichloro-9,10-dihydro-9,10-methanoanthracen-9-ylmethyl)-4-piperidinone, the title compound was obtained in 36% yield as a white solid, mp 187°–189° C. (dec). TLC analysis on the free base (R$_f$ 0.31, 40% ethyl acetate in hexane) free base: 1H NMR (CDCl$_3$, 300 MHz) 8.06 (dd, J=1.8, 4.9 Hz, 1H), 7.52 (dd, J=1.8, 7.4 Hz, 1H), 7.18 (m, 4H), 6.90 (m, 3H), 4.23 (s, 1H), 4.03 (s, 3H), 3.77 (s, 1H), 3.39 (s, 2H), 2.82 (m, 4H), 2.61 (d, J=1.4 Hz, 2H), 2.01 (m, 4H) MS (CI, CH4) m/z 481 (M+1,100), 483 (63), 485 (12), 509 (M+29,9), 463 (26) hydrochloride salt:

Analysis for $C_{27}M_{26}Cl2N_2O_2 \cdot 2HCl$: Calculated: C, 58.50; H, 5.09; N, 5.05 Found: C, 58.24; H, 4.94; N, 4.89

The starting piperidinone was prepared as follows:

a. Methyl 2-chloro-9,10-dihydro-9,10-methano-9-anthracenecarboxylate

To a solution of 2-chloro-9,10-dihydro-9,10-methano-9-anthracenecarboxylic acid (described in example 1j) (10.03 g, 37.1 mmol) in toluene (100 mL) was added thionyl chloride (4.05 mL, 55.7 mmol, 1.5 eq). The reaction was heated to reflux monitoring gas evolution with a bubbler of mineral oil. Gas evolution ceased after 30 min at which time the reaction was cooled slightly under nitrogen and a large excess of methanol (10 mL) was added. The solution was again heated to reflux for 1 h, cooled to room temperature under nitrogen, and stirred for 18 h. Aqueous NaOH (2.5N, 60 mL) was added and the aqueous phase was extracted with ethyl acetate (2×70 mL). Combined organic extracts were dried over anhydrous magnesium sulfate, filtered, and reduced to a solid. The reaction product was purified by flash chromatography over silica gel (250 mL, eluent: 15% ethyl acetate in hexane) to yield 10.2 g (97%) of the title compound as a highly crystalline white solid. TLC (R$_f$ 0.45, 10% ethyl acetate in hexane). MS (CI, CH4) m/z 285 (M+1,100), 287 (31), 313 (M+29,11), 253 (14), 225 (14), 205 (8)

b. Methyl 2-chloro-7-nitro-9,10-dihydro-9,10-methano-9-anthracenecarboxylate and methyl 2-chloro-6-nitro-9,10-dihydro-9,10-methano-9-anthracenecarboxylate To the methyl 2-chloro-9,10-dihydro-9,10-methano-9-anthracenecarboxylate (described in example 35a) (20.33 g, 71.4 mmol) was added solid ammonium nitrate (6.09 g, 67.8 mmol, 0.95 eq) and trifluoroacetic anhydride (35.3 mL, 250 mmol, 3.5 eq) under nitrogen. Cooled acetonitrile (0° C., 300 mL) was added and the suspension became homogeneous within 5 min Although an ice bath was present, the reaction exotherm warmed the solution to room temperature. Once the reaction temperature began to fall, the bath was removed and the reaction was stirred for an additional 30 min The reaction was quenched with saturated aqueous sodium bicarbonate (200 mL) carefully. The aqueous phase was extracted with ethyl acetate (3×200 mL). Combined organic extracts were dried over anhydrous magnesium sulfate, filtered, and reduced to a partly crystalline product oil. A portion of the 7-nitro title compound (6.86 g) was purified from the crude reaction mixture by crystallization from hexane/ethyl acetate (2 recrystallizations, 200 mL hexane:50 mL ethyl acetate). The rest of the material, including mother liquors from the crystallization, was purified by flash chromatography over silica gel (500 mL. eluent: 10% ethyl acetate in hexane increased to 12% over time). The two purification schemes resulted in 10.83 g (46%) of 7-nitro title compound and 6.59 g (28%) of the 6-nitro isomer. TLC analysis ($R_f$ 0.26 (2,7), 0.22 (2,6), 10% ethyl acetate in hexane). MS (CI, CH4) m/z 2,7: 330 (M+1,100), 332 (36), 358 (M+29,11); 2,6: 330 (M+1,100), 332 (38), 358 (M+29,12)

c. Methyl 2-amino-7-chloro-9,10-dihydro-9,10-methano-9-anthracenecarboxylate

To a suspension of methyl 2-chloro-7-nitro-9,10-dihydro-9,10-methano-9-anthracenecarboxylate (described in example 35b) (7.36 g, 22.32 mmol) in ethanol (150 mL) was added stannous chloride dihydrate (25.2 g, 112 mmol, 5 eq). The reaction was heated to reflux at which time it became homogeneous. After heating for 2.5 h, the solution was cooled to 0° C. and quenched with ice followed by 10% NaOH (200 mL). The aqueous phase was extracted with ethyl acetate (3×150 mL). Combined organic extracts were dried over anhydrous magnesium sulfate, filtered, and reduced to a solid. The reaction product was purified by flash chromatography over silica gel (400 mL, eluent: 25% ethyl acetate in hexane) to yield 5.06 g (76%) of the title compound. TLC analysis ($R_f$ 0.16, 30% ethyl acetate in hexane). MS (CI, CH4) m/z 300 (M+1,100), 302 (33), 328 (M+29,9), 264 (12), 182 (11), 121 (11), 89 (44)

d. Methyl 2,7-dichloro-9,10-dihydro-9,10-methano-9-anthracenecarboxylate

To a vigorously stirred solution of cupric chloride (161 mg, 1.2 mmol, 1.2 eq) in dry acetonitrile (5 mL) under nitrogen was added t-butyl nitrite (90%, 0.178 mL, 1.50 mmol, 1.5 eq). This was followed by methyl 2-amino-7-chloro-9,10-dihydro-9,10-methano-9-anthracenecarboxylate (described in example 35c) (300 mg, 1.0 mmol) added in portions. Gas was evolving during this time and the color changed form yellow/green to a dark yellow/brown. Stirring of the reaction continued an additional 1.5 h after all the substrate had been added. The reaction was quenched by the addition of 3N HCl (10 mL). The aqueous phase was extracted with ethyl acetate (3×10 mL). Combined organic extracts were dried over anhydrous magnesium sulfate, filtered and reduced to an oil. The reaction product was purified by flash chromatography over silica gel (30 mL, eluent: 40% methylene chloride in hexane) to yield 230 mg (72%) of the title compound as a white solid. TLC analysis ($R_f$ 0.28, 40% methylene chloride in hexane). MS (CI, CH4) m/z 319 (M+1,35), 321 (24), 323 (3), 285 (20), 84 (100)

e. 2,7-Dichloro-9,10-dihydro-9,10-methano-9-anthracenecarboxylic acid

To a solution of methyl 2,7-dichloro-9,10-dihydro-9,10-methano-9-anthracenecarboxylate (described in example 35d) (3.25 g, 10.2 mmol) in tetrahydrofuran/methanol (1:1, 70 mL) was added an aqueous solution (35 mL) of lithium hydroxide monohydrate (4.28 g, 102 mmol, 10 eq). A slight exotherm occurred on addition. The reaction was stirred vigorously for 18 h at room temperature over which time a cloudiness develops. The solvents are removed and replaced with 3N HCl (50 mL) saturated with sodium chloride. The aqueous phase was extracted with ethyl acetate (3×50 mL). Combined organic extracts were dried over anhydrous magnesium sulfate, filtered and reduced to an oil. The procedure yielded 3.11 g (quantitative) of the title compound and did not require addition purification.

f. 1-(2,7-Dichloro-9,10-dihydro-9,10-methanoanthracen-9-ylcarbonyl)piperidin-4-ol Using a procedure similar to that described in example 1k except starting with 2,7-dichloro-9,10-dihydro-9,10-methano-9-anthracenecarboxylic acid (described in example 35e), the title compound was formed in quantitative yield as a viscous oil. On the basis of crude NMR, no additional purification or characterization was pursued.

g. 1-(2,7-Dichloro-9,10-dihydro-9,10-methanoanthracen-9-ylmethyl)piperidin-4-ol

Using a procedure similar to that described in example 1l except starting with 1-(2,7-dichloro-9,10-dihydro-9,10-methanoanthracen-9-ylcarbonyl)piperidin-4-ol (described in example 35f), the title compound was formed in 86% yield as a white solid. TLC analysis ($R_f$ 0.15, 50% ethyl acetate in hexane). MS (CI, CH4) m/z 373 (M+1,100), 375 (62), 377 (9), 401 (M+29,10), 355 (18)

h. 1-(2,7-Dichloro-9,10-dihydro-9,10-methanoanthracen-9-ylmethyl)-4-piperidinone Using a procedure similar to that described in example 1m except starting with 1-(2,7-dichloro-9,10-dihydro-9,10-methanoanthracen-9-ylmethyl)piperidin-4-ol (described in example 35g), the title compound was formed in 39% yield as a white solid. TLC analysis ($R_f$ 0.18, 20% ethyl acetate in hexane). 1H NMR (CDCl$_3$, 250 MHz) 7.17 (d, J=7.7 Hz, 2H), 7.13 (d, J=1.8 Hz, 2H), 6.93 (dd, J=7.8, 1.8 Hz, 2H), 4.29 (s, 1H), 3.46 (s, 2H), 2.96 (t, J=6.1Hz, 4H), 2.63 (d, J=1.3 Hz, 2H), 2.45 (d, J=6.1Hz, 4H) MS (CI, CH4) m/z 372 (M+1,100), 374 (64), 376 (12), 400 (M+29,9), 338 (31), 289 (7)

EXAMPLE 36

4-(2-Hydroxy-3-pyridyl)-1-(9,10-dihydro-9,10-methanoanthracen-9-ylmethyl)piperidin-4-ol To a dimethylformamide solution (3.5 mL) of sodium hydride (60% in mineral oil, 58 mg, 1.46 mmol, 2.5 eq) under nitrogen was added ethanethiol (0.108 mL, 1.46 mmol, 2.5 eq) via gas tight syringe. Once gas evolution had ceased, a solution of 1-(9,10-dihydro-9,10-methanoanthracen-9-ylmethyl)-4-(2-methoxy-3-pyridyl)piperidin-4-ol (described in example 32) (240 mg, 0.58 mmol) in dimethylformamide (2.0 mL) was added in a single portion. After the reaction had refluxed for 2 h, it was cooled to room temperature and diluted with water (25 mL). The resulting precipitate was filtered and purified by flash chromatography over silica gel (140 mL, eluent: 15% methanol in methylene chloride) to yield 190 mg (83%) of the title compound as a white solid. TLC analysis ($R_f$ 0.10, 15% methanol in methylene chloride). 1H NMR (CDCl$_3$, 300 HHz) 7.36 (dd, J=2.0, 7.2 Hz, 1H), 7.23 (m, 5H), 6.94 (m,4H), 6.31 (dd, J=6.7, 6.8 Hz, 1H), 5.82 (s, 1H), 4.27 (s, 1H), 3.48 (s, 2H), 2.84 (m, 2H), 2.61 (d, J=1.4 Hz, 1H), 2.00 (m, 2H), 1.89 (m, 2H) MS (CI, CH4) m/z 399 (M+1,100), 427 (M+29,7), 381 (18) The free base was dissolved in methanol/methylene chloride, acidified with ethereal HCl and the hydrochloride salt was precipitated by ether dilution. The salt was filtered, rinsed with fresh diethyl ether, and dried in vacuo (50° C., 75 pascal, 18 h) to yield a white solid, mp 195°–199° C.

Analysis for $C_{26}H_{26}N_2O_2 \cdot 1.9HCl$: Calculated: C, 66.76; H, 6.01; N, 5.99 Found: C, 66.98; H, 5.90; N, 5.93

EXAMPLE 37

4-(4-Hydroxy-3-pyridyl)-1-(9,10-dihydro-9,10-methanoanthracen-9-ylmethyl)piperidin-4-ol Using a procedure similar to that described in example 36 except starting with 1-(9,10-dihydro-9,10-methanoanthracen-9-ylmethyl)-4-(4-methoxy-3-pyridyl)piperidin-4-ol (described in example 33), the title compound was obtained in 94% yield as a white solid, mp 233°–235° C. free base: 1H NMR (D6 DMSO, 250 MHz) 7.64 (s, 1H), 7.62 (d, J=7.1 Hz, 1H), 7.26 (dd, J=2.1, 6.2 Hz, 2H), 7.20 (dd, J=1.7, 7.7 Hz, 2H), 6.91 (m, 4H), 6.55 (s, 1H), 6.12 (d, J=6.9 Hz, 1H), 4.31 (s, 1H), 3.38 (s, 2H), 2.69 (m, 4H), 2.48 (s, 2H), 1.96 (m, 2H), 1.59 (m, 2H) MS (CI, CH4) m/z 399 (M+1,100), 427 (M+29,15), 381 (88) hydrochloride salt:

Analysis for $C_{26}H_{26}N_2O_2 \cdot 2HCl \cdot 1.1H_2O$: Calculated: C, 63.57; H, 6.21; N, 5.70 Found: C, 63.61; H, 6.10; N, 5.60

EXAMPLE 38

4-(6-Hydroxy-2-pyridyl)-1-(9,10-dihydro-9,10-methanoanthracen-9-ylmethyl)piperidin-4-ol Using a procedure similar to that described in example 36 except starting with 1-(9,10-dihydro-9,10-methanoanthracen-9-ylmethyl)-4-(6-methoxy-2-pyridyl)piperidin-4-ol (described in example 13), the title compound was obtained in 65% yield as a white solid, mp 218°–222° C. (dec). free base: 1H NMR (CDCl$_3$, 250 MHz) 7.39 (dd, J=7.1, 7.7 Hz, 1H), 7.20 (m, 4H), 6.94 (m, 4H), 6.42 (d, J=8.9 Hz, 1H), 6.15 (d, J=6.4 Hz, 1H), 4.50 (br s, 1H), 4.27 (s, 1H), 3.47 (s, 2H), 2.94 (m, 2H), 2.73 (m, 2H), 2.59 (d, J=1.0 Hz, 2H), 1.98 (dt, J=4.5, 12.7 Hz, 2H), 1.79 (m, 2H) MS (CI, CH4) m/z 399 (M+1,3), 427 (M+29,0.3), 443 (41), 381 (0.4), 19 (100) hydrochloride salt:

Analysis for $C_{26}H_{26}N_2O_2 \cdot 2HCl \cdot 0.75H_2O$: Calculated.: C, 64.40; H, 6.13; N, 5.78 Found: C, 64.40; H, 6.28; N, 5.72

EXAMPLE 39

1-(9,10-Dihydro-9,10-methanoanthracen-9-ylmethyl)-4-(2-N-methylamino-3-pyridyl)piperidin-4-ol A solution of n-butyllithium (2.0M in hexane, 7.0 mL, 14 mmol, 6.3 eq) was added to tetrahydrofuran (25 mL) precooled to −72° C. under a nitrogen atmosphere. A large excess of methyl amine (40 mL) was condensed by a dry ice jacketed addition funnel and added dropwise to the butyllithium solution. After stirring for 15 min, 1-(9,10-dihydro-9,10-methanoanthracen-9-ylmethyl)-4-(2-methoxy-3-pyridyl)piperidin-4-ol hydrochloride(described in example 32) (1.00 g, 2.22 mmol) was added in a single portion. The reaction was allowed to warm to room temperature and excess methyl amine was vented. After refluxing the solution for 18 h, the flask was cooled to room temperature and treated with water (25 mL). The aqueous phase was extracted with ethyl acetate (3×25 mL). Combined organic extracts were dried over anhydrous sodium sulfate, filtered and concentrated to an oil. The reaction was purified by flash chromatography over silica gel (60 mL, eluent: 40% ethyl acetate in hexane) to yield 520 mg (57%) of the title compound as a white solid. TLC analysis ($R_f$ 0.16, 30% ethyl acetate in hexane). 1H NMR (CDCl$_3$, 300 MHz) 8.05 (dd, J=1.4, 4.9 Hz, 1H), 7.22 (m, 5H), 6.93 (m, 4H), 6.47 (dd, J=5.0, 7.3 Hz, 1H), 6.42 (m, 1H), 4.27 (s, 1H), 3.47 (s, 2H), 2.97 (d, J=4.2 Hz, 3H), 2.90 (m, 2H), 2.73 (ddd, J=3.3, 11.1, 11.1 Hz, 2H), 2.60 (d, J=1.0 Hz, 2H), 2.03 (m, 2H), 1.65 (m, 2H) MS (CI, CH4) m/z 412 (M+1,100), 440 (M+29,15), 394 (25) The free base was dissolved in methylene chloride, treated with excess ethereal HCl, and the hydrochloride salt precipitated upon dilution with diethyl ether. The hydrochloride salt was filtered, rinsed with fresh ether, and dried in vacuo (50° C., 10 pascal, 18 h) to yield an off-white solid, mp 220°–221° C. (dec).

Analysis for $C_{27}H_{29}N_3O \cdot 2HCl \cdot H_2O$: Calculated: C, 64.54; H, 6.62; N, 8.36 Found: C, 64.62; H, 6.64; N, 8.12

EXAMPLE 40

1-(9,10-Dihydro-9,10-methanoanthracen-9-ylmethyl)-4-(2-N-propylamino-3-pyridyl)piperidin-4-ol Using a procedure similar to that described in example 39 except employing propyl amine, the title compound was obtained in 79% yield as a white solid, mp 215°–220° C. (dec). free base: 1H NMR (CDCl$_3$, 300 MHz) 8.01 (dd, J=1.7, 4.9 Hz, 1H), 7.21 (m, 5H), 6.93 (m, 4H), 6.45 (dd, J=4.9, 4.9 Hz, 1H), 4.27 (s, 1H), 3.47 (s, 2H), 3.39 (dt, J=7.1, 5.2 Hz, 2H), 2.90 (m, 2H), 2.73 (dt, J=2.9, 11.0, 11.2 Hz, 2H), 2.60 (d, J=1.4 Hz, 2H), 2.02 (m, 4H), 1.65 (m, 2H), 0.99 (t, J=7.4 Hz, 3H) MS (CI,CH4) m/z 440 (M+1,100), 468 (M+29,15), 422 (11) hydrochloride salt:

Analysis for $C_{29}H_{33}N_3O \cdot 2HCl \cdot 0.6H_2O$: Calculated: C, 66.56; H, 6.97; N, 8.03 Found: C, 66.39; H, 6.96; N, 7.66

EXAMPLE 41

1-(9,10-Dihydro-9,10-methanoanthracen-9-ylmethyl)-4-(2-N-propylamino-5-pyridyl)piperidin-4-ol Using a procedure similar to that described in example 39 except starting with 1-(9,10-dihydro-9,10-methanoanthracen-9-ylmethyl)-4-(2-methoxy-5-pyridyl)piperidin-4-ol (described in example 11) and employing propyl amine, the title compound was obtained in 88% yield as a white crystalline solid, mp 235°–237° C. (dec). TLC analysis of the free base ($R_f$ 0.25 in ethyl acetate). free base: 1H NMR (CDCl$_3$, 250 MHz) 8.18 (d, J=2.5 Hz, 1H), 7.54 (dd, J=2.5, 8.7 Hz, 1H), 7.21 (m, 4H), 6.93 (m, 4H), 6.35 (d, J=8.7 Hz, 1H), 4.50 (br t, J=5.6 Hz, 1H), 4.27 (s, 1H), 3.46 (s, 2H), 3.20 (dt, J=7.0, 5.9 Hz, 2H), 2.88 (m, 2H), 2.71 (dt, J=11.7, 2.4, 11.7 Hz, 2H), 2.61 (d, J=1.3 Hz, 2H), 2.05 (dt, J=4.4, 13.2, 12.1Hz, 2H), 1.72 (m, 2H), 1.62 (m, 2H), 0.99 (t, J=7.3 Hz, 3H) MS (CI,CH4) m/z 440 (M+1,100), 468 (M+29,18), 422 (56) hydrochloride salt:

Analysis for $C_{29}H_{33}N_3O \cdot 2HCl \cdot 0.25H_2O$: Calculated: C, 67.37; H, 6.92; N, 8.13 Found: C, 67.35; H, 6.93; N, 8.12

EXAMPLE 42

1-(9,10-Dihydro-9,10-methanoanthracen-9-ylmethyl)-4-(2-methoxy-3-quinolinyl)piperidin-4-ol To a cooled solution (−72° C.) or t-butyllithium (1.7M in pentane, limiting reagent, 1.90 mL, 3.19 mmol) in tetrahydrofuran (24 mL) under nitrogen was added several drops of diisopropylamine (catalytic amount). This was followed by 2-methoxyquinoline (0.69 mL, 4.39 mmol, 1.38 eq). The reaction was stirred at −72° C. for 1 h, warmed to 0° C. and stirred at this temperature for 3 h. After recooling to −72° C., a solution of 1-(9,10-dihydro-9,10-methanoanthracen-9-ylmethyl)-4-piperidinone (described in example 5d) (1.00 g, 3.30 mmol, 1.03 eq) in tetrahydrofuran (3.0 mL) was added dropwise to the lithioquinoline solution. The reaction was stirred at room temperature for 18 h and quenched with water (10 mL). The aqueous phase was extracted with ethyl acetate (200 mL). The organic extract was washed with water (2×200 mL), dried with anhydrous sodium sulfate and reduced to an oil. The reaction mixture was purified by flash chromatography over silica gel (100 mL; eluent: 25% ethyl acetate in hexane) to obtain 1.00 g (66%) of the title compound as a white solid. TLC analysis ($R_f$ 0.19, 25% ethyl acetate in hexane). 1H NMR (CDCl$_3$, 250 MHz) 7.89 (s, 1H), 7.81 (d, J=8.4 Hz, 1H), 7.88 (d, J=7.7 Hz, 1H), 7.59 (dd, J=6.8, 7.3 Hz, 1H), 7.38 (dd, J=7.4, 7.5 Hz, 1H), 7.23 (m, 4H), 6.93 (m, 4H), 4.27 (s, 1H), 4.16 (s, 3H), 3.80 (s, 1H), 3.49 (s, 2H), 2.87 (m, 4H), 2.63 (s, 2H), 2.09 (m, 4H) MS (CI, CH4) m/z 463 (M+1,100), 491 (M+29,19), 445 (23) The free base was dissolved in methylene chloride, treated with ethereal HCl, and the hydrochloride salt was precipitated with ether dilution. The solid was filtered, rinsed with fresh diethyl ether and dried in vacuo (50° C., 10 pascal, 18 h) to yield a white solid, mp 213°–217° C. (dec).

Analysis on $C_{31}H_{30}N_2O_2 \cdot 1.5HCl$: Calculated: C, 71.98; H, 6.14; N, 5.42 Found: C, 71.78; H, 6.07; N, 5.40

EXAMPLE 43

4-(2-Benzothiazyl)-1-(9,10-dihydro-9,10-methanoanthracen-9-ylmethyl)piperidin-4-ol Using a procedure similar to that described in example 42 except employing benzothiazole, the title compound was formed in 65% yield as a white solid, mp 307°–310° C. (dec). free base: 1H NMR (CDCl$_3$, 300 MHz) 7.97 (d, J=8.0 Hz, 1H), 7.87 (d, J=8.0 Hz, 1H), 7.47 (dd, J=8.0, 8.0 Hz, 1H), 7.37 (dd, J=8.0, 8.0 Hz, 1H), 7.23 (m, 4H), 6.94 (m, 4H), 4.30 (s, 1H), 3.50 (s, 2H), 3.10 (s, 1H), 2.97 (m, 2H), 2.76 (m, 2H), 2.63 (s, 2H), 2.32 (m, 2H), 1.89 (m, 2H) MS (CI, CH4) m/z 439 (M+1,100), 467 (M+29,18), 421 (15), 89 (50) hydrochloride salt:

Analysis for $C_{28}H_{26}N_2OS \cdot 2HCl \cdot H_2O$: Calculated: C, 63.51; H, 5.71; N, 5.29 Found: C, 63.26; H, 5.38; N, 4.76

EXAMPLE 44

1-(9,10-Dihydro-9,10-methanoanthracen-9-ylmethyl)-4-(2-pyridylmethyl)piperidin-4-ol Using a procedure similar to that described in example 42 except employing 2-picoline, the title compound was formed in quantitative yield as a white solid, mp 205°–207° C. (dec). free base: 1H NMR (CDCl$_3$, 300 MHz) 8.40 (s, 1H), 7.53 (d, J=7.7 Hz, 1H), 7.17 (m, 6H), 6.91 (m, 4H), 4.25 (s, 1H), 3.42 (s, 2H), 2.78 (m, 2H), 2.71 (s, 2H), 2.58 (s, 2H), 2.54 (m, 2H), 1.68 (m, 2H), 1.46 (m, 2H) MS (CI, CH4) m/z 397 (M+1,100), 425 (M+29,19), 379 (17) hydrochloride salt:

Analysis for $C_{27}H_{28}N_2O \cdot 2HCl \cdot 1.5H_2O$: Calculated: C, 65.32; H, 6.69; N, 5.64 Found: C, 65.34; H, 6.46; N, 5.50

EXAMPLE 45

1-(2-Chloro-9,10-dihydro-9,10-methanoanthracen-9-ylmethyl)-4-(2-methoxy-3-quinolinyl)piperidin-4-ol Using a procedure similar to that described in example 42 except starting with 1-(2-chloro-9,10-dihydro-9,10-methanoanthracen-9-ylmethyl)-4-piperidinone (described in example 1m), the title compound was formed in 46% yield as a white solid, mp 225°–230° C. (dec). free base: 1H NMR (CDCl$_3$, 250 MHz) 7.90 (s, 1H), 7.82 (d, J=8.2 Hz, 1H), 7.69 (dd, j=1.1, 8.1 Hz, 1H), 7.60 (ddd, J=1.5, 7.1, 8.2 Hz, 1H), 7.38 (m, 1H), 7.20 (m, 4H), 6.94 (m, 4H), 4.25 (s, 1H), 4.17 (s, 3H), 3.79 (s, 1H), 3.46 (s, 2H), 2.85 (m, 4H), 2.62 (d, J=0.9 Hz, 2H), 2,08 (m, 4H) MS (CI, CH4) m/z 497 (M+1,100), 499 (39), 525 (M+29,20), 479 (29) hydrochloride salt:

Analysis for $C_{31}H_{29}N_2O_2Cl \cdot HCl \cdot H_2O$ Calculated: C, 67.51; H, 5.84; N, 5.08 Found: C, 67.63; H, 5.51; N, 5.02

EXAMPLE 46

1-(9,10-Dihydro-9,10-methanoanthracen-9-ylmethyl)-4-(4-methoxybenzyl)piperidin-4-ol Magnesium turnings (0.32 g, 1.32 mmol, 1.3 eq) were stirred in the absence of solvent for 15 min under nitrogen. Diethyl ether (20 mL) and catalytic lithium iodide were added, and the suspension was stirred vigorously for an additional 15 min at which time 4-methoxybenzyl chloride (1.08 mL, 7.0 mmol, 8 eq) was syringed into the reaction flask in portions. The reaction was refluxed for 3 h to assure Grignard formation and recooled to room temperature. 1-(9,10-Dihydro-9,10-methanoanthracen-9-ylmethyl)-4-piperidinone (described in example 5d) (0.30 g, 1.00 mmol) was added dropwise as a tetrahydrofuran solution (25 mL). After stirring for 18 h, the reaction was quenched with water (10 mL). The aqueous phase was extracted with ethyl acetate (200 mL). The organic extract was washed with water (2×100 mL), dried with anhydrous sodium sulfate, filtered, and reduced to an oil. The reaction mixture was purified by flash chromatography over silica gel (25 mL, eluent: 20% ethyl acetate in hexane) to yield 0.29 g (69%) of the title compound as a white solid. 1H NMR (CDCl$_3$, 300 MHz) 7.23 (m, 2H), 7.13 (m 4H), 6.88 (m, 6H), 4.25 (s, 1H), 3.78 (s, 3H), 3.41 (s, 2H), 2.76 (m, 2H), 2.66 (s, 2H), 2.57 (d, J=1.2 Hz, 2H), 2.52 (m, 2H), 1.67 (m, 2H), 1.47 (m, 2H), 1.57 (s, 1H) MS (CI, CH4) m/z 426 (M+1,100), 454 (M+29,13), 408 (20) The free base was dissolved in methanol and methylene chloride, acidified with ethereal HCl and the salt precipitated with ether dilution. The hydrochloride salt was filtered, rinsed with fresh ether, and dried in vacuo (50° C., 10 pascal, 18 h) to yield a white solid, mp 267°–268° C. (dec).

Analysis for $C_{29}H_{31}NO_2 \cdot HCl \cdot 0.7H_2O$: Calculated: C, 73.39; H, 7.09; N, 2.95 Found: C, 73.48; H, 6.85; N, 2.85

EXAMPLE 47

4-(4-Chlorobenzyl)-1-(9,10-dihydro-9,10-methanoanthracen-9-ylmethyl)piperidin-4-ol Using a procedure similar to that described in example 46 except employing 4-chlorobenzyl chloride, the title compound was formed in 86% yield as a white solid, mp 264–265 C. free base: 1H NMR (CDCl$_3$, 250 MHz) 7.22 (m, 8H), 6.93 (m, 4H), 4.66 (s, 1H), 4.25 (s, 1H), 3.40 (s, 2H), 2.77 (m, 2H), 2.69 (s, 2H), 2.56 (d, J=1.5 Hz, 2H), 2.49 (m, 2H), 1.66 (m, 2H), 1.45 (m, 2H) MS (CI, CH4) m/z 430 (M+1,100), 458 (M+29,25), 412 (39), 431 (35), 432 (36), 125 (30), 113 (22) hydrochloride salt:

Analysis for $C_{28}H_{28}NOCl.HCl.0.1H_2O$: Calculated: C, 71.82; H, 6.29; N, 2.99 Found: C, 71.66; H, 6.31; N, 2.94

EXAMPLE 48

4-Benzyl-1-(9,10-dihydro-9,10-methanoanthracen-9-ylmethyl)piperidin-4-ol

Using a procedure similar to that described in example 46 except employing benzyl chloride, the title compound was formed in 54% yield as a white solid, mp 193°–195° C. (dec). free base: 1H NMR (CDCl$_3$, 250 MHz) 7.21 (m, 9H), 6.93 (m, 4H), 4.25 (s, 1H), 3.41 (s, 2H), 2.78 (m, 2H), 2.73 (s, 2H), 2.57 (s, 2H), 1.69 (dt, J=4.4, 13.4 Hz, 2H), 1.56 (s, 1H), 1.47 (m, 2H) MS (CI, CH4) m/z 396 (M+1,100), 424 (M+29,17), 378 (10) hydrochloride salt:

Analysis for $C_{28}H_{29}NO.HCl.0.3H_2O$: Calculated: C, 76.89; H, 7.05; N, 3.20 Found: C, 76.68; H, 7.12; N, 3.21

EXAMPLE 49

1-(2-Chloro-9,10-dihydro-9,10-methanoanthracen-9-ylmethyl)-4-(1,1-dimethylethyl)piperidin-4-ol To a cooled solution (–78° C.) of lithium bromide (770 mg, 8.87 mmol, 1.5 eq) in tetrahydrofuran (60 mL) under nitrogen was added recently titrated t-butyllithium (1.7M in pentane, 4.20 mL, 7.10 mmol, 1.2 eq). The resulting strong yellow color was quenched on the addition of a 1-(2-chloro-9,10-dihydro-9,10-methanoanthracen-9-ylmethyl)-4-piperidinone (described in example 1m) (2.00 g, 5.92 mmol) solution in tetrahydrofuran (15 mL). The reaction was warmed to room temperature over 10 min and quenched with water (50 mL). The aqueous phase was extracted with ethyl acetate (3×60 mL). Combined organic extracts were dried over anhydrous magnesium sulfate, filtered and concentrated to an oil. The reaction mixture was purified by flash chromatography over silica gel (150 mL, eluent: 15% ethyl acetate in hexane) to obtain 1.22 g (52%) of the title compound as a white solid. TLC analysis ($R_f$ 0.23, 20% ethyl acetate in hexane). 1H NMR (CDCl$_3$, 300 MHz) 7.24 (m, 1H), 7.14 (m, 2H), 6.95 (m, 3H), 6.87 (m, 1H), 4.24 (br s, 1H), 3.56 (s, 2H), 2.82 (m, 2H), 2.59 (d, J=1.4 Hz, 2H), 2.50 (m, 2H), 1.74 (m, 2H), 1.50 (m, 2H), 0.91 (br s, 9H) MS (CI, CH4) m/z 396 (M+1,100), 398 (35), 424 (M+29,17), 378 (45), 360 (6) The free base was dissolved in diethyl ether containing a small amount of methylene chloride and acidified with ethereal HCl. The hydrochloride salt was filtered, washed with fresh ether and dried in vacuo (60° C., 13 pascal, 18 h) to yield a white solid, mp 294°–296° C.

Analysis for $C_{25}H_{30}ClNO.HCl.0.5H_2O$: Calculated: C, 68.02; H, 7.31; N, 3.17 Found: C, 67.96; H, 6.98; N, 3.03

EXAMPLE 50

1-(2,7-Dichloro-9,10-dihydro-9,10-methanoanthracen-9-ylmethyl)-4-(1,1-dimethylethyl)piperidin-4-ol Using a procedure similar to that described in example 49 except starting with 1-(2,7-dichloro-9,10-dihydro-9,10-methanoanthracen-9-ylmethyl)-4-piperidinone (described in example 35h), the title compound was formed in 51% yield as a white solid, mp 194°–196° C. TLC analysis on the free base ($R_f$ 0.27, 20% ethyl acetate in hexane). free base: 1H NMR (CDCl$_3$, 300 MHz) 7.15 (d, J=1.8 Hz, 2H), 7.13 (d, J=7.8 Hz, 2H), 6.90 (dd, J=1.8, 7.7 Hz, 2H), 4.22 (s, 1H), 3.33 (s, 2H), 2.80 (br d, J=10.8 Hz, 2H), 2.59 (s, 2H), 2.52 (br t, J=11.2 Hz, 2H), 1.74 (br dt, 2H), 1.50 (br dd, 2H), 0.92 (s, 9H) MS (CI, CH4) m/z 430 (M+1,100), 432 (60), 434 (11), 458 (M+29,14), 412 (61), 414 (44), 394 (11), 170 (11) hydrochloride salt:

Analysis for $C_{25}H_{29}Cl_2NO.HCl$: Calculated: C, 64.32; H, 6.48; N, 3.00 Found: C, 64.03; H, 6.33; N, 2.89

EXAMPLE 51

4-Butyl-1-(9,10-dihydro-9,10-methanoanthracen-9-ylmethyl)piperidin-4-ol

Using a procedure similar to that described in example 49 except starting with 1-(9,10-dihydro-9,10-methanoanthracen-9-ylmethyl)-4-piperidinone (described in example 5d) and employing n-butyllithium, the title compound was formed as a white solid, mp 194°–196° C. TLC analysis on the free base ($R_f$ 0.22, 30% ethyl acetate in hexane). free base: 1H NMR (CDCl$_3$, 250 MHz) 7.20 (m, 4H), 6.94 (m, 4H), 4.26 (s, 1H), 3.41 (s, 2H), 2.73 (m, 2H), 2.60 (d, J=2.0 Hz, 2H), 1.53 (m, 10H), 0.9 (t, 3H) MS (CI, CH4) m/z 362 (M+1,100), 390 (M+29,13), 344 (47), 304 (44) hydrochloride salt:

Analysis for $C_{25}H_{31}NO.HCl.0.6H_2O$: Calculated: C, 73.45; H, 8.18; N, 3.43 Found: C, 73.09; H, 7.80; N, 4.09

EXAMPLE 52

1-(9,10-Dihydro-9,10-methanoanthracen-9-ylmethyl)-4-(6-methoxy-2-benzothiazyl)piperidin-4-ol To a cooled solution (–72° C.) of n-butyllithium (2.5M in hexane, 0.84 mL, 2.1 mmol, 1.05 eq) in tetrahydrofuran (20 mL) under nitrogen was added 6-methoxybenzthiazole (literature preparation: M. D. Friedman, P. L. Stotter, T. H. Porter, K. Folkers J. Med. Chem. 1973, 16, 1314) (0.36 g, 2.2 mmol, 1.1 eq) as a tetrahydrofuran solution (2 mL). After 40 min a tetrahydrofuran solution (3 mL) of 1-(9,10-dihydro-9,10-methanoanthracen-9-ylmethyl)-4-piperidinone (described in example 5d) was added dropwise and warmed to room temperature over 30 min The reaction was stirred for 3 h and quenched with water (20 mL). The aqueous phase was extracted with ethyl acetate (200 mL). The organic phase was washed with water (2×100 mL), dried over anhydrous sodium sulfate, filtered, and reduced to an oil. The reaction mixture was purified by flash chromatography over silica gel (100 mL, eluent: 30% ethyl acetate in hexane) to obtain 0.74 g (72%) of the title compound as an off-white solid. TLC analysis ($R_f$ 0.21, 30% ethyl acetate in hexane). 1H NMR (CDCl$_3$, 250 MHz) 7.82 (d, J=8.9 Hz, 1H), 7.30 (d, J=2.5 Hz, 1H), 7.25 (dd, J=3.1, 5.8 Hz, 2H), 7.17 (dd, J=2.2, 5.2 Hz, 2H), 7.04 (dd, J=2.5, 9.0 Hz, 1H), 6.93 (m, 4H), 4.27 (s, 1H), 3.85 (s, 3H), 3.48 (s, 2H), 3.10 (br s, 1H), 2.95 (m, 2H), 2.74 (dt, J=2.2, 11.6 Hz, 2H), 2.61 (d, J=1.2 Hz, 2H), 2.28 (dt, J=4.5, 12.5 Hz, 2H), 1.87 (m, 2H) MS (CI, CH4) m/z 469 (M+1,100), 497 (M+29,19), 451 (17) The free base was dissolved in diethyl ether containing a small amount of methylene chloride, acidified with ethereal HCl, and the hydrochloride salt suspension was diluted with additional ether. The salt was filtered, washed with fresh ether, and dried in vacuo (50° C., 10 pascal, 18 h) to yield an off white solid, mp 249°–251° C. (dec).

Analysis for $C_{29}H_{28}N_2O_2S.2HCl.0.25H_2O$: Calculated: C, 63.79; H, 5.63; N, 5.13 Found: C, 63.71; H, 5.49; N, 5.06

EXAMPLE 53

4-(2-Benzthienyl)-1-(9,10-dihydro-9,10-methanoanthracen-9-ylmethyl)piperidin-4-ol Using a procedure similar to that described in example 52 except employing benzthiophene, the title compound was formed in 90% yield as a white solid, mp 278°–285° C. free base: 1H NMR ($D_6$-DMSO, 300 MHz) 7.87 (d, J=7.5 Hz, 1H), 7.72 (d, J=6.0 Hz, 1H), 7.26 (m, 7H), 6.92 (m, 4H), 4.32 (s, 1H), 3.41 (s, 2H), 2.79 (m, 2H), 2.69 (m, 2H), 2.50 (s, 2H), 1.97 (m, 2H), 1.82 (m, 2H) MS (CI, CH4) m/z 438 (M+1,100), 466 (M+29,20), 420 (35) hydrochloride salt:

Analysis for $C_{29}H_{27}NOS \cdot HCl \cdot 0.2H_2O$: Calculated: C, 72.92; H, 5.99; N, 2.93 Found: C, 72.72; H, 5.80; N, 2.87

EXAMPLE 54

1-(9,10-Dihydro-9,10-methanoanthracen-9-ylmethyl)-4-(2-furanyl)piperidin-4-ol

Using a procedure similar to that described in example 52 except employing furan, the title compound was formed in 33% yield as an off-white solid, mp 265°–272° C. (dec). free base: 1H NMR (CDCl$_3$, 300 MHz) 7.24 (m, 5H), 6.93 (m, 4H), 6.30 (m, 1H), 6.20 (m, 1H), 4.26 (br s, 1H), 3.43 (s, 2H), 2.70 (m, 4H), 2.59 (d, 2H), 2.05 (m, 2H), 1.92 (m, 2H) MS (CI, CH4) m/z 372 (M+1,100), 400 (M+29,17), 354 (60), 332 (22) hydrochloride salt:

Analysis for $C_{25}H_{25}NO_2 \cdot 1.3HCl \cdot 0.2H_2O$: Calculated: C, 71.07; H, 6.37; N, 3.12 Found: C, 70.94; H, 6.13; N, 3.17

EXAMPLE 55

1-(9,10-Dihydro-9,10-methanoanthracen-9-ylmethyl)-4-(2-thienyl)piperidin-4-ol

Using a procedure similar to that described in example 52 except employing thiophene, the title compound was formed in 72% yield as a white solid, mp 134°–138° C. (dec). free base: 1H NMR (CDCl$_3$, 300 MHz) 7.20 (m, 4H), 6.94 (m, 7H), 4.27 (br s, 1H), 3.48 (s, 2H), 2.86 (m, 2H), 2.73 (m, 2H), 2.61 (s, 2H), 2.13 (m, 2H), 1.93 (m, 2H) MS (CI, CH4) m/z 388 (M+1,100), 416 (M+29,24), 370 (76), 304 (19), 196 (12), 91 (17) hydrochloride salt:

Analysis for $C_{25}H_{25}NOS \cdot 1.4HCl \cdot 0.1H_2O$: Calculated: C, 68.18; H, 6.09; N, 3.18 Found: C, 67.78; H, 5.72; N, 3.14

EXAMPLE 51

1-(9,10-Dihydro-9,10-methanoanthracen-9-ylmethyl)-4-(5-thiazyl)piperidin-4-ol

Using a procedure similar to that described in example 52 except employing thiazole, the title compound was formed in 28% yield as a white solid, mp 196°–198° C. (dec). TLC analysis of the free base (R$_f$ 0.14, ethyl acetate). free base: 1H NMR (CDCl$_3$, 300 MHz) 8.71 (s, 1H), 7.76 (s, 1H), 7.24 (m, 2H), 7.16 (m, 2H), 6.95 (m, 4H), 4.27 (br s, 1H), 3.46 (s, 2H), 2.87 (m, 2H), 2.74 (m, 2H), 2.60 (d, J=1.4 Hz, 1H), 2.14 (m, 2H), 1.93 (m, 2H) MS (CI, CH4) m/z 389 (M+1, 100), 417 (M+29,23), 371 (23) hydrochloride salt:

Analysis for $C_{24}H_{25}N_2OS \cdot 2HCl \cdot 1.1H_2O$: Calculated: C, 59.90; H, 5.90; N, 5.82 Found: C, 59.52; H, 5.64; N, 5.64

EXAMPLE 57

1-(2-Chloro-9,10-dihydro-9,10-methanoanthracen-9-ylmethyl)-4-(5-thiazyl)piperidin-4-ol Using a procedure similar to that described in example 52 except employing 2-(trimethylsilyl)thiazole and 1-(2-chloro-9,10-dihydro-9,10-methanoanthracen-9-ylmethyl)-4-piperidinone (described in example 1m), the title compound was formed in 40% yield as a white solid, mp 206°–210° C. (dec). free base: 1H NMR (CDCl$_3$, 300 MHz) 8.71 (s, 1H), 7.76 (s, 1H), 7.20 (m, 1H), 7.14 (m, 2H), 6.97 (m, 2H), 6.89 (dd, J=1.8, 7.7 Hz, 1H), 4.26 (br s, 1H), 3.42 (br s, 2H), 2.84 (m, 2H), 2.73 (m, 2H), 2.61 (br s, 2H), 2.13 (m, 2H), 1.98 (m, 2H) MS (CI, CH4) m/z 423 (M+1,100), 425 (40), 451 (M+29,19), 405 (24) hydrochloride salt:

Analysis for $C_{24}H_{23}ClN_2OS \cdot 2HCl \cdot 0.5H_2O$: Calculated: C, 57.09; H, 5.19; N, 5.55 Found: C, 56.80; H, 5.12; N, 5.37

The starting 2-(trimethylsilyl)thiazole was prepared as follows:

a. 2-(Trimethylsilyl)thiazole

To a cooled solution (−98° C.) of n-butyllithium (2.5M in hexane, 5.39 mL, 13.4 mmol, 1.1 eq) in tetrahydrofuran (100 mL) under nitrogen was added a solution of 2-bromothiazole (2.00 g, 12.2 mmol) in tetrahydrofuran (30 mL). A suspension formed as the substrate was added. After stirring at −90° C. for 30 min, freshly distilled trimethylsilyl chloride (1.55 mL, 12.2 mmol, 1.0 eq) was added. The reaction was warmed to −30° C. over 1 h and quenched with saturated aqueous sodium bicarbonate (50 mL). The aqueous phase was extracted with diethyl ether (2×40 mL). Combined organic extracts were washed with aqueous bicarbonate (2×40 mL), saturated brine (1×40 mL) and dried with anhydrous sodium sulfate. The solvents were removed and the product purified by Kugelrohr distillation at reduced pressure (2400 pascal, 110° C.). By NMR the title compound was contaminated with small amounts of starting material but no further purification was considered necessary. No accurate yield was established. MS (CI, CH4) m/z 158 (M+1,100), 186 (M+29,17)

EXAMPLE 58

1-(9,10-Dihydro-9,10-methanoanthracen-9-ylmethyl)-4-(2-fluoro-3-pyridyl)-piperidin-4-ol To a cooled solution (−72° C.) of distilled diisopropylamine (7.86 mL, 56.1 mmol, 1.3 eq) in tetrahydrofuran/hexane (57 mL/37 mL) under nitrogen was added n-butyllithium (2.5M in hexane, 23.8 mL, 59.4 mmol, 1.4 eq). The resulting solution was warmed to −20° C. to assure deprotenation and then recooled to −72° C. A tetrahydrofuran (13 mL) solution of 2-fluoropyridine (4.50 mL, 53.5 mmol, 1.25 eq) was then added dropwise resulting in a yellow precipitate. The deprotenation reaction was warmed to −50° C. for 45 min and briefly allowed to reach −30° C. before being recooled to −72° C. To this solution was added a mixture of 1-(9,10-dihydro-9,10-methanoanthracen-9-ylmethyl)-4- piperidinone (described in example 5d) (13.0 g, 42.9 mmol) and lithium bromide (7.45 g, 85.8 mmol, 2 eq) in tetrahydrofuran (48 mL) in a dropwise fashion. In the course of the addition, the yellow precipitate dissolved. The reaction was warmed to −20° C. over 1.5 h and quenched with acetic acid (10 mL). The solution was diluted with water (400 mL), basified with 2.5N NaOH and extracted with ethyl acetate (3×300 mL). The combined organic extracts were dried over anhydrous sodium sulfate, filtered and reduced to a solid. The product was purified by recrystallization from ethyl acetate (3 crops) to yield 13.3 g (77%) of the title compound as a white solid. TLC analysis (R$_f$ 0.22, 30% ethyl acetate in hexane). 1H NMR (CDCl$_3$, 300 MHz) 8.09 (d, J=8.2 Hz, 1H), 7.91 (dd, J=8.2, 9.4 Hz, 1H), 7.21 (m, 5H), 6.94 (m, 4H), 4.27 (s, 1H), 3.48 (s, 2H), 2.91 (m, 2H), 2.74 (m, 2H), 2.62 (s, 2H), 2.26 (m, 2H), 1.78 (m, 2H) MS (CI, CH4) m/z 401 (M+1,100), 429 (M+29,15), 383

(21) The free base was dissolved in ether and acidified with ethereal HCl. The hydrochloride salt was filtered, washed with fresh ether and dried in vacuo (room temperature, 10 pascal, 18 h) to yield a white solid, mp 188°–191° C. (dec).

Analysis for $C_{26}H_{25}FN_2O\cdot HCl\cdot 0.4H_2O$: Calculated: C, 70.31; H, 6.08; N, 6.31 Found: C, 70.65; H, 6.12; N, 5.83

EXAMPLE 59

1-(9,10-Dihydro-9,10-methanoanthracen-9-ylmethyl)-4-(3-pyridylmethyl)piperidin-4-ol Using a procedure similar to that described in example 58 except employing 3-picoline, the title compound was formed in 46% yield as a white solid, mp 140°–142° C. (dec). free base: 1H NMR (CDCl$_3$, 300 MHz) 8.48 (d, J=3.0 Hz, 1H), 7.61 (ddd, J=1.8, 7.7, 7.7 Hz, 1H), 7.20 (m, 6H), 6.92 (m, 4H), 4.24 (s, 1H), 3.42 (s, 2H), 2.88 (s, 2H), 2.70 (m 4H), 2.57 (s, 2H), 1.54 (m, 4H) MS (CI, CH4) m/z 397 (M+1,100), 425 (M+29,14), 379 (16), 304 (16), 89 (32) hydrochloride salt:

Analysis for $C_{27}H_{28}N_2O\cdot 2HCl\cdot 1.5H_2O$: Calculated: C, 65.32; H, 6.70; N, 5.64 Found: C, 65.31; H, 6.59; N, 5.31

EXAMPLE 60

1-(9,10-Dihydro-9,10-methanoanthracen-9-ylmethyl)-4-(2-ethylthio-3-pyridyl)piperidin-4-ol To a solution of the 1-(9,10-dihydro-9,10-methanoanthracen-9-ylmethyl)-4-(2-fluoro-3-pyridyl)piperidin-4-ol (described in example 58) (2.00 g, 5.00 mmol, 1 eq) in tetrahydrofuran (50 mL) under nitrogen was added the sodium salt of ethanethiol (0.90 g, 10.7 mmol, 2.2 eq). The thiolate salt was prepared from ethanethiol and sodium hydride under standard conditions. The reaction was heated to reflux for 18 h and quenched by pouring into water (100 mL). The aqueous phase was extracted with diethyl ether (2×100 mL). Combined organic extracts were washed with water (2×100 mL), dried over anhydrous sodium sulfate, filtered, and reduced to an oil. The reaction product was purified by flash chromatography over silica gel (200 mL, eluent: 50% ether in hexane) to yield 2.00 g (90%) of the title compound. TLC analysis (R$_f$ 0.29, 50% ether in hexane). 1H NMR (CDCl$_3$, 250 HHz) 8.35 (dd, J=1.6, 4.7 Hz, 1H), 7.58 (dd, J=1.7, 7.7 Hz, 1H), 7.22 (m, 4H), 6.95 (m, 5H), 4.27 (s, 1H), 3.58 (s, 1H), 3.48 (s, 2H), 3.28 (q, J=7.3 Hz, 2H), 2.89 (m, 2H), 2.80 (ddd, J=9.3, 14.9, 10.7 Hz, 2H), 2.62 (d, J=1.5 Hz, 2H), 2.12 (m, 4H), 1.35 (t, J=7.2 Hz, 3H) MS (CI, CH4) m/z 443 (M+1,100), 471 (M+29,16), 425 (25) The free base was dissolved in ether and acidified with ethereal HCl. The hydrochloride salt was filtered, rinsed with fresh ether and dried in vacuo (room temperature, 10 pascal, 18 h) to yield a white solid, mp 176°–179° C. (dec).

Analysis for $C_{28}H_{30}N_2OS\cdot 2HCl\cdot 0.5H_2O$: Calculated: C, 64.11; H, 6.34; N, 5.34 Found: C, 64.05; H, 6.32; N, 5.26

EXAMPLE 61

1-(9,10-Dihydro-9,10-methanoanthracen-9-ylmethyl)-4-(2-propyloxy-3-pyridyl)piperidin-4-ol Using a procedure similar to that described in example 60 except employing n-propanol, the title compound was formed in 86% yield as a white solid, mp 172°–175° C. (dec). free base: 1H NMR (CDCl$_3$, 250 HHz) 8.03 (dd, J=1.7, 5.0 Hz, 1H), 7.53 (dd, J=1.8, 7.5 Hz, 1H), 7.22 (m, 4H), 6.92 (m, 5H), 4.37 (t, J=6.5 Hz, 2H), 4.29 (s, 1H), 3.88 (s, 1H), 3.48 (s, 2H), 2.80 (m, 4H), 2.62 (s, 2H), 2.02 (m, 4H), 1.83 (m, J=6.7, 7.3 Hz, 2H), 1.04 (t, J=7.4 Hz, 3H) MS (CI, CH4) m/z 441 (M+1,100), 469 (M+29,14), 423 (31), 206 (4), 138 (8) hydrochloride salt:

Analysis for $C_{29}H_{32}N_2O_2\cdot 2HCl\cdot 0.5H_2O$: Calculated: C, 66.66; H, 6.75; N, 5.36 Found: C, 67.76; H, 6.59; N, 5.16

EXAMPLE 62

1-(9,10-Dihydro-9,10-methanoanthracen-9-ylmethyl)-4-(2-(2,2,2-trifluoroethoxy)-3-pyridyl)piperidin-4-ol Using a procedure similar to that described in example 60 except employing 2,2,2-trifluoroethanol, the title compound was formed in 94% yield as a white solid, mp 165–170 C. (dec). free base: 1H NMR (CDCl$_3$, 300 MHz) 8.03 (dd, J=1.2, 4.9 Hz, 1H), 7.65 (dd, J=1.8, 7.5 Hz, 1H), 7.23 (m, 4H), 6.95 (m, 5H), 4.84 (q, J(H,F)=8.5 Hz, 2H), 4.27 (s, 1H), 3.48 (s, 2H), 2.88 (m, 2H), 2.80 (ddd, J=2.3, 11.6, 11.7 Hz, 2H), 2.61 (d, J=1.4 Hz, 2H), 2.12 (ddd, J=4.5, 12.0, 11.9 Hz, 2H), 1.92 (m, 2H) MS (CI, CH4) m/z 481 (M+1,100), 509 (M+29,1), 463 (27) hydrochloride salt:

Analysis for $C_{28}H_{27}N_2O_2F_3\cdot 1.5HCl$: Calculated: C, 62.84; H, 5.37; N, 5.23 Found: C, 62.98; H, 5.40; N, 5.20

EXAMPLE 63

4-(2-Benzyloxy-3-pyridyl)-1-(9,10-dihydro-9,10-methanoanthracen-9-ylmethyl)piperidin-4-ol Using a procedure similar to that described in example 60 except employing benzyl alcohol, the title compound was formed in 94% yield as a white solid, mp 170°–180° C. (dec). free base: 1H NMR (CDCl$_3$, 300 MHz) 8.07 (dd, J=1.8, 5.0 Hz, 1H), 7.57 (dd, J=1.8; 7.5 Hz, 1H), 7.42 (m, 2H), 7.34 (m, 3H), 7.25 (m 2H), 7.18 (m, 2H), 6.93 (m, 6H), 5.48 (s, 2H), 4.26 (s, 1H), 3.72 (s, 1H), 3.45 (s, 2H), 2.86 (m, 2H), 2.75 (ddd, J=2.5, 11.6, 11.4 Hz, 2H), 2.60 (d, J=1.4 Hz, 2H), 2.09 (m, 2H), 1.96 (m, 2H) MS (CI, CH4) m/z 489 (M+1,100), 517 (M+29,13), 471 (27) hydrochloride salt:

Analysis for $C_{33}H_{32}N_2O_2\cdot 2HCl\cdot H_2O$: Calculated: C, 68.39; H, 6.26; N, 4.83 Found: C, 68.30; H, 6.00; N, 4.97

EXAMPLE 64

1-(9,10-Dihydro-9,10-methanoanthracen-9-ylmethyl)-4-(2-methoxy-3-pyridyl)piperidin-4-ol Using a procedure similar to that described in example 60 except employing methanol, the title compound was formed in 94% yield as a white solid, mp 225°–228° C. (dec). free base: 1H NMR (CDCl$_3$, 300 MHz) 8.05 (dd, J=4.9, 1.7 Hz, 1H), 7.49 (dd, J=7.5, 5.7 Hz, 1H), 7.22 (m, 4H), 6.92 (m, 5H), 4.27 (s, 1H), 4.02 (s, 3H), 3.78 (s, 1H), 3.48 (s, 2H), 2.83 (m, 4H), 2.61 (d, J=1.4 Hz, 2H), 2.00 (m, 4H) MS (CI, CH4) m/z 413 (M+1,100), 441 (M+29,13), 395 (24) hydrochloride salt:

Analysis for $C_{27}H_{28}N_2O_2\cdot HCl\cdot 0.2H_2O$: Calculated: C, 71.65; H, 6.55; N, 6.19 Found: C, 71.43; H, 6.46; N, 5.84

EXAMPLE 65

1-(9,10-Dihydro-9,10-methanoanthracen-9-ylmethyl)-4-(2-(1-methylethoxy)-3-pyridyl)piperidin-4-ol Using a procedure similar to that described in example 60 except employing 2-propanol, the title compound was formed in quantitative yield as a white solid, mp 156°–160°

C. (dec). free base: 1H NMR (CDCl$_3$, 300 MHz) 8.02 (dd, J=1.8, 5.0 Hz, 1H), 7.48 (dd, J=1.8, 7.5 Hz, 1H), 7.2 (m, 4H), 6.95 (m, 4H), 6.84 (dd, J=4.9, 7.5 Hz, 1H), 5.48 (m, 1H), 4.27 (br s, 1H), 4.09 (br s, 1H), 2.82 (m, 4H), 2.61 (d, J=1.4 Hz, 2H), 1.99 (m, 4H), 1.39 (d, J=6.2 Hz, 6H) MS (CI, CH4) m/z 441 (M+1,100), 469 (M+29,8), 423 (27), 399 (22), 304 (2), 249 (9), 235 (5), 192 (9), 164 (69) hydrochloride salt:

Analysis for C$_{29}$H$_{32}$N$_2$O$_2$.2.3HCl.H$_2$O: Calculated: C, 64.20; H, 6.74; N, 5.16 Found: C, 64.55; H, 6.27; N, 4.71

EXAMPLE 66

1-(9,10-Dihydro-9,10-methanoanthracen-9-ylmethyl)-4-(2-(N-pyrrolidinyl)-3-pyridyl)piperidin-4-ol To a cooled solution (0° C.) of pyrrolidine (0.417 mL, 5.00 mmol, 5 eq) in tetrahydrofuran (10 mL) under nitrogen was added n-butyllithium (2.5M in hexane, 1.92 mL, 4.80 mmol, 4.8 eq). This was followed by 1-(9,10-dihydro-9,10-methanoanthracen-9-ylmethyl)-4-(2-fluoro-3-pyridyl)-piperidin-4-ol (described in example 58) (0.400 g, 1.00 mmol) in tetrahydrofuran (10 mL). The bath was removed and the solution warmed to room temperature over 1.5 h. No reaction was evident after stirring for 18 h. To accelerate the reaction, 18-crown-6 (0.528 g, 2.00 mmol, 2.0 eq) was added and the solution was heated to 60° C. for 5 h. The reaction was quenched with water (30 mL) and extracted with ethyl acetate (3×20 mL). The combined organic extracts were dried over anhydrous magnesium sulfate, filtered, and reduced to an oil. The reaction product was purified by flash chromatography over silica gel (35 mL, eluent: 50% ethyl acetate in hexane) to yield 0.450 g (quantitative) of the title compound. TLC analysis (R$_f$ 0.23, 50% ethyl acetate in hexane). 1H NMR (CDCl$_3$, 300 MHz) 8.35 (dd, J=1.7, 4.6 Hz, 1H), 7.63 (dd, J=1.8, 7.9 Hz, 1H), 7.22 (m, 4H), 7.12 (dd, J=7.9, 4.6 Hz, 1H), 6.93 (m, 4H), 4.27 (br s, 1H), 3.48 (s, 2H), 3.21 (m, 4H), 2.85 (m, 2H), 2.76 (m, 2H), 2.63 (d, J=1.3 Hz, 2H), 2.01 (m, 6H), 1.70 (m, 2H) MS (CI, CH4) m/z 452 (M+1,100), 480 (M+29,12), 434 (16) The free base was dissolved in ether and acidified with ethereal HCl. The hydrochloride salt was filtered, rinsed with fresh ether and dried in vacuo (60° C., 16 pascal, 18 h) to yield a white solid, mp 249°–253° C.

Analysis for C$_{30}$H$_{33}$N$_3$O.2HCl.H$_2$O: Calculated: C, 66.60; H, 6.86; N, 7.77 Found: C, 66.78; H, 6.66; N, 7.64

EXAMPLE 67

1-(9,10-Dihydro-9,10-methanoanthracen-9-ylmethyl)-4-(2-(N-methylethylamino)-3-pyridyl)piperidin-4-ol Using a procedure similar to that described in example 66 except employing N-methyl-ethylamine, the title compound was formed in 59% yield as a white solid, mp 179°–182° C. (dec). free base: 1H NMR (CDCl$_3$, 250 MHz) 8.36 (dd, J=1.8, 4.6 Hz, 1H), 7.67 (dd, J=1.7, 7.9 Hz, 1H), 7.23 (m, 4H), 7.13 (dd, J=5.1, 8.5 Hz, 1H), 6.93 (m, 4H), 4.27 (s, 1H), 3.48 (s, 2H), 3.05 (q, J=7.1Hz, 2H), 2.80 (m, 4H), 2.68 (s, 3H), 2.63 (d, J=1.3 Hz, 2H), 2.03 (ddd, J=4.8, 11.9, 12.0 Hz, 2H), 1.70 (m, 2H), 1.58 (br s, 1H), 1.07 (t, J=7.3 Hz, 3H) MS (CI, CH4) m/z 440 (M+1,100), 468 (M+29,15), 422 (21), 420 (13), 248 (8), 137 (9) hydrochloride salt:

Analysis for C$_{29}$H$_{33}$N$_3$O.2.5HCl.0.5H$_2$O: Calculated: C, 64.53; H, 6.82; N, 7.78 Found: C, 64.71; H, 6.95; N, 7.44

EXAMPLE 68

1-(9,10-Dihydro-9,10-methanoanthracen-9-ylmethyl)-4-(2-(N-methylamino)-3-pyridyl)piperidin-4-ol Using a procedure similar to that described in example 66 except employing methylamine, the title compound was formed in 89% yield as a white solid, mp 220°–221° C. (dec). free base: 1H NMR (CDCl$_3$, 300 MHz) 8.05 (dd, J=1.4, 4.9 Hz, 1H), 7.22 (m, 5H), 6.93 (m, 4H), 6.47 (dd, J=5.0, 7.3 Hz, 1H), 6.42 (m, 1H), 4.27 (s, 1H), 3.47 (s, 2H), 2.97 (d, J=4.2 Hz, 3H), 2.90 (m, 2H), 2.73 (ddd, J=3.3, 11.1, 11.1 Hz, 2H), 2.60 (d, J=1.0 Hz, 2H), 2.03 (m, 2H), 1.65 (m, 2H) MS (CI, CH4) m/z 412 (M+1,100), 440 (M+29,15), 394 (25) hydrochloride salt:

Analysis for C$_{27}$H$_{29}$N$_3$O.2HCl.H$_2$O: Calculated: C, 64.54; H, 6.62; N, 8.36 Found: C, 64.62; H, 6.64; N, 8.12

EXAMPLE 69

1-(2-Chloro-9,10-dihydro-9,10-methanoanthracen-9-ylmethyl)-4-(5-(hydroxymethyl)-3-pyridyl)piperidin-4-ol A tetrahydrofuran solution (15 mL) of 4-(5-(tert-butyldimethylsilyl)oxymethyl-3-pyridyl)-1-(2-chloro-9,10-dihydro-9,10-methanoanthracen-9-ylmethyl)piperidin-4-ol (1.70 g, 3.04 mmol) was cooled to 0° C. under nitrogen and treated with tetrabutylammonium fluoride (1.0N in tetrahydrofuran, 3.20 mL, 3.20 mmol, 1.05 eq). The reaction was warmed to room temperature and stirred at that temperature for 3 h. Water (15 mL) was added and the resulting aqueous phase was extracted with ethyl acetate (3×15 mL). Combined organic extracts were dried over anhydrous sodium sulfate, filtered, and reduced to an oil. This procedure resulted in 1.20 g (89%) of the title compound. TLC analysis (R$_f$ 0.11, 5% methanol in diethyl ether). No additional purification was required. 1H NMR (CDCl$_3$, 250 MHz) 8.62 (s, 1H), 8.42 (s, 1H), 7.84 (s, 1H), 7.21 (m, 4H), 6.94 (m, 3H), 4.69 (s, 2H), 4.27 (s, 1H), 3.44 (s, 2H), 2.90 (m, 2H), 2.74 (m, 2H), 2.62 (d, J=1.3 Hz, 2H), 2.11 (m, 2H), 1.76 (m, 2H) MS (CI, CH4) m/z 447 (M+1,100), 449 (32), 475 (M+29,19), 429 (71), 431 (25) The free base was dissolved in ether and acidified with ethereal HCl. The hydrochloride salt was filtered, rinsed with fresh ether and dried in vacuo (room temperature, 10 pascal, 18 h) to yield a white solid, mp 235°–240° C. (dec).

Analysis for C$_{27}$H$_{27}$N$_2$O$_2$Cl.2HCl.0.7H$_2$O: Calculated: C, 60.55; H, 6.23; N, 5.23 Found: C, 60.26; H, 5.71; N, 5.13

The starting silyl ether was prepared as follows:

a. 3-Bromo-5-(hydroxymethyl)pyridine

To a toluene suspension (100 mL) of 5-bromonicotinic acid (15.00 g, 74.3 mmol) was added thionyl chloride (6.00 mL, 81.7 mmol, 1.1 eq). The suspension was heated to reflux monitoring gas evolution with a mineral oil bubbler. After 60 min the system became homogeneous and achieved a steady state condition with respect to gas evolution. The reaction was cooled to room temperature. Excess thionyl chloride and the solvent were removed in vacuo to yield solid acid chloride hydrochloride salt. In a separate flask sodium borohydride (9.10 g, 241 mmol, 13 eq) was added to absolute ethanol (200 mL) and cooled to −10° C. under nitrogen. The acid chloride was added in portions over 20 min maintaining the reaction temperature under 0° C. at all times. After the addition was complete, the reaction was warmed to room temperature and stirred for 1 h. Water (200 mL) was added and the aqueous phase extracted with diethyl ether (2×200 mL). The combined organic extracts were washed with water (100 mL), dried over anhydrous potassium carbonate, and filtered. The product was precipitated as its hydrochloride salt by treating the solution with ethereal HCl. The solid was dried in vacuo (room temperature, 16 pascal, 7 h). No additional purification was required. The procedure yielded 10.04 g (60%) of the title compound hydrochloride salt. MS (CI, CH4) m/z 188 (M+1,100), 190 (99), 216 (M+29, 8), 218 (8), 170 (25), 172 (24)

b. 3-Bromo-5-(tert-butyldimethylsilyl)oxymethylpyridine

To a methylene chloride solution (20 mL) of 3-bromo-5-(hydroxymethyl)pyridine hydrochloride (described in example 69a) (1.00 g, 4.48 mmol) under nitrogen was added triethylamine (2.50 mL, 17.9 mmol, 4 eq) and tert-butyldimethylsilyl chloride (0.75 g, 5.0 mmol, 1.1 eq). The resulting solution was heated to reflux for 18 h, cooled to room temperature and diluted with diethyl ether (200 mL). The organic phase was washed with 2.5N NaOH (1×100 mL), water (3×100 mL) and saturated brine (1×100 mL). The ether solution was dried over anhydrous magnesium sulfate, filtered, and reduced to an colorless oil. The procedure resulted in 1.10 g (81%) of the title compound. The product required no additional purification. TLC analysis ($R_f$ 0.19, ethyl acetate) MS (CI, CH4) m/z 302 (M+1,100), 304 (96), 330 (M+29,4), 332 (4)

c. 4-(5-(tert-Butyldimethylsilyl)oxymethyl-3-pyridyl)-1-(2-chloro-9,10-dihydro-9,10-methanoanthracen-9-ylmethyl)piperidin-4-ol Using a procedure similar to that described in example 1 except employing 3-bromo-5-(tert-butyldimethylsilyl)oxymethylpyridine (described in example 69b) and 1-(2-chloro-9,10-dihydro-9,10-methanoanthracen-9-ylmethyl)-4-piperidinone (described in example 1m), the title compound was formed in 51% yield as an oil. TLC analysis ($R_f$ 0.20, 25% ethyl acetate in hexane). MS (CI, CH4) m/z 561 (M+1,100), 563 (40), 589 (M+29,20), 545 (26), 429 (26)

EXAMPLE 70

1-(9,10-Dihydro-9,10-methanoanthracen-9-ylmethyl)-4-(5-(hydroxymethyl)-3-pyridyl)piperidin-4-ol Using a procedure similar to that described in example 69 except starting with 4-(5-(tert-butyldimethylsilyl)oxymethyl-3-pyridyl)-1-(9,10-dihydro-9,10-methanoanthracen-9-ylmethyl)piperidin-4-ol, the title compound was formed in 85% yield as a white solid, mp 210–215 C. free base: 1H NMR (CDCl$_3$, 250 MHz) 8.65 (d, J=2.0 Hz, 1H), 8.42 (d, J=1.4 Hz, 1H), 7.84 (dd, J=2.5, 1.3 Hz, 1H), 7.22 (m, 4H), 6.93 (m, 4H), 4.89 (br t, 1H), 4.63 (d, J=2.8 Hz, 2H), 4.46 (br s, 1H), 4.29 (s, 1H), 3.49 (s, 2H), 2.87 (m, 4H), 2.63 (s, 2H), 2.06 (m, 2H), 1.73 (m, 2H) MS (CI, CH4) m/z 413 (M+1,100), 441 (M+29,17), 395 (61) hydrochloride salt:

Analysis for $C_{27}H_{28}N_2O_2.2HCl.0.9H_2O$: Calculated: C, 64.64; H, 6.391 N, 5.58 Found: C, 64.50; H, 6.34; N, 5.48

The starting silyl ether was prepared as follows:

a. 4-(5-(tert-Butyldimethylsilyl)oxymethyl-3-pyridyl)-1-(9,10-dihydro-9,10-methanoanthracen-9-ylmethyl)piperidin-4-ol Using a procedure similar to that described in example 1 except starting with 1-(9,10-dihydro-9,10-methanoanthracen-9-ylmethyl)-4-piperidinone (described in example 5d) and employing 3-bromo-5-(tert-butyldimethylsilyl)oxymethylpyridine (described in example 69b), the title compound was formed in 62% yield as an oil. TLC analysis ($R_f$ 0.25, 30% ethyl acetate in hexane). MS (CI, CH4) m/z 527 (M+1,100), 555 (M+29,14), 509 (20),395 (20)

EXAMPLE 71

1-(9,10-Dihydro-9,10-methanoanthracen-9-ylmethyl)-4-(2-(hydroxymethyl)-5-thiazyl)piperidin-4-ol Using a procedure similar to that described in example 69 except starting with 1-(9,10-dihydro-9,10-methanoanthracen-9-ylmethyl)-4-(5-(2-(tert-butyldimethylsiloxymethyl)thiazyl))piperidin-4-ol, the title compound was formed in 48% yield as a white solid, mp 145–150 C. TLC analysis of the free base ($R_f$ 0.18, ethyl acetate). free base: 1H NMR (CDCl$_3$, 300 MHz) 7.56 (s, 1H), 7.25 (m, 2H), 7.16 (m, 2H), 6.94 (m, 4H), 4.89 (s, 2H), 4.28 (br s, 1H), 3.46 (s, 2H), 2.85 (m, 2H), 2.73 (m, 2H), 2.11 (m, 2H), 1.93 (m, 2H) MS (CI, CH4) m/z 419 (M+1, 100), 447 (M+29,16), 401 (42), 304 (50) hydrochloride salt:

Analysis for $C_{25}H_{26}N_2O_2S.C6H_8O_7$: Calculated: C, 60.97; H, 5.61; N, 4.59 Found: C, 60.86; H, 5.80; N, 4.35

The starting silyl ether was prepared as follows:

a. 2-Formylthiazole

To a cooled solution (−95° C.) of t-butyllithium (1.7M in pentane, 17.9 mL, 30.5 mmol, 2.0 eq) in tetrahydrofuran (150 mL) under nitrogen was added 2-bromothiazole (2.50 g, 15.3 mmol). The resulting suspension was stirred below −80° C. for 45 min The lithiated thiazole solution was transfeted via cannula to a solution of dimethylformamide (1.42 mL) in tetrahydrofuran (100 mL) at −90° C. The reaction was allowed to warm to room temperature over 2 h and quenched by the addition of water (100 mL). The aqueous phase was extracted with ethyl acetate (3×75 mL). Combined organic extracts were dried over anhydrous magnesium sulfate, filtered and reduced to a crude oil in 87% yield. TLC analysis ($R_f$ 0.50, 40% ethyl acetate in hexane). No further characterization was undertaken; the crude title compound was taken on to the sodium borohydride reduction.

b. 2-(Hydroxymethyl)thiazole

To a cooled solution (0° C.) of 2-formylthiazole (described in example 71a) (1.50 g, 13.27 mmol) in methanol (25 mL) under nitrogen was added sodium borohydride (0.300 g, 7.94 mmol). After the addition was complete, the reaction was warmed to room temperature over 1 h and stirred at room temperature for 3 h. Excess reagent was quenched with acetone (10 mL) and stirred 18 h. The reaction was acidified with 3N HCl (25 mL), cooled to 0° C. and rebasified with 2.5N NaOH (40 mL). The aqueous phase was extracted with ethyl acetate (3×25 mL). Combined organic extracts were dried over anhydrous magnesium sulfate, filtered and reduced to a relatively pure oil in 62% yield. TLC analysis ($R_f$ 0.15, 40% ethyl acetate in hexane). No further purification was required. MS (CI, CH4) m/z 116 (M+1,82), 144 (M+29,17), 98 (100)

c. 2-(tert-Butyldimethylsilyl)oxymethylthiazole

Using a procedure similar to that described in example 69b except starting with 2-(hydroxymethyl)thiazole (described in example 71b), the title compound was formed in 92% yield. TLC analysis ($R_f$ 0.21, 10% ether in hexane). MS (CI, CH4) m/z 230 (M+1,26), 258 (M+29,11), 214 (24), 172 (100)

d. 4-(2-(tert-Butyldimethylsilyl)oxymethyl-5-thiazyl)-1-(9,10-dihydro-9,10-methanoanthracen-9-ylmethyl)piperidin-4-ol Using a procedure similar to that described in example 1 except starting with 1-(9,10-dihydro-9,10-methanoanthracen-9-ylmethyl)-4-piperidinone (described in example 5d) and employing 2-(tert-butyldimethylsilyl)oxymethylthiazole (described in example 71c), the title compound was formed in 58% yield as a yellow oil. TLC analysis ($R_f$ 0.19, 25% ethyl acetate in hexane). MS (CI, CH4) m/z 533 (M+1,100), 561 (M+29,16), 515 (21), 475 (12)

EXAMPLE 72

1-(9,10-Dihydro-9,10-methanoanthracen-9-ylmethyl)-4-(5-N-methylcarbamoylmethyl-3-pyridyl)piperidin-4-ol To a solution of 1-(9,10-dihydro-9,10-methanoanthracen-9-ylmethyl)-4-(5-(hydroxymethyl)-3-pyridyl)piperidin-4-ol (described in example 70) (0.50 g, 1.12 mmol) in methylene chloride (5 mL) was added methyl isocyanate (0.070 mL, 1.18 mmol, 1.05 eq) and N-methyl piperidine (0.10 mL, 0.82 mmol, 0.75 mmol). The resulting solution was heated to reflux for 9 h, cooled to room temperature and diluted with ethyl acetate (100 mL). The organic phase was washed with water (2×100 mL), dried over anhydrous sodium sulfate, filtered and reduced. The reaction product was purified by flash chromatography over silica gel (60 mL, eluent: 75% ethyl acetate in hexane) to yield 0.380 g (67%) of the title compound as a white solid. TLC analysis ($R_f$ 0.22, 75% ethyl acetate in hexane). 1H NMR (CDCl$_3$, 250 MHz) 8.70 (d, J=2.1 Hz, 1H), 8.49 (s, 1H), 7.80 (s, 1H), 7.20 (m, 4H), 6.95 (m, 3H), 5.12 (s, 2H), 4.73 (br m, 1H), 4.27 (s, 1H), 3.44 (s, 2H), 2.90 (m, 2H), 2.81 (d, J=4.8 Hz, 3H), 2.73 (m, 2H), 2.62 (s, 2H), 2.10 (m, 2H), 1.77 (m, 2H) MS (CI, CH4) m/z 504 (M+1,100), 506 (38), 532 (M+29,11), 486 (25), 447 (45), 429 (32) The free base was dissolved in ether containing methylene chloride and acidified with ethereal HCl. The hydrochloride salt was precipitated with ether dilution, filtered, and dried in vacuo (room temperature, 10 pascal, 18 h) to yield a white solid, mp 200°–204° C. (dec).

Analysis for $C_{29}H_{30}ClN_3O_3 \cdot 2HCl \cdot H_2O$: Calculated: C, 58.54; H, 5.76; N, 7.06 Found: C, 58.56; H, 5.67; N, 7.10

EXAMPLE 73

1-(9,10-Dihydro-9,10-methanoanthracen-9-ylmethyl)-4-(5-(1-hydroxyethyl)-3-pyridyl)piperidin-4-ol A suspension of 1-(9,10-dihydro-9,10-methanoanthracen-9-ylmethyl)-4-(5-formyl-3-pyridyl)piperidin-4-ol (0.350 g, 0.852 mmol) in tetrahydrofuran (20 mL) under nitrogen was cooled to 0° C. Methyl lithium (1.0M in diethyl ether, 1.72 mL, 2 eq) was added dropwise with dissolution of the suspension as addition proceeded. The solution became a golden brown color. The reaction was warmed to 10° C. and stirred at this temperature for 2.5 h. At the end of this time period, the reaction was quenched with water (25 mL) and the aqueous phase extracted with ethyl acetate (3×20 mL). Combined organic extracts were dried over anhydrous magnesium sulfate, filtered, and reduced to an oil. The reaction product was purified by flash chromatography over silica gel (30 mL, eluent: 10% methanol in diethyl ether) to yield 0.280 g (77%) of the title compound as a white solid. TLC analysis ($R_f$ 0.17, 10% methanol in diethyl ether). 1H NMR (CDCl$_3$, 300 MHz) 8.65 (d, J=2.2 Hz, 1H), 8.48 (d, J=2.0 Hz, 1H), 7.83 (t, J=2.1Hz, 1H), 7.24 (m, 2H), 7.18 (m, 2H), 6.95 (m, 4H), 4.95 (q, J=6.5 Hz, 1H), 4.28 (br s, 1H), 3.49 (br s, 2H), 2.94 (m, 2H), 2.74 (m, 2H), 2.63 (br s, 2H), 2.13 (m, 2H), 1.76 (m, 2H), 1.59 (m, 3H) MS (CI, CH4) m/z 427 (M+1,100), 455 (M+29,17), 409 (62), 235 (11), 221 (22), 206 (17), 169 (28) The free base was dissolved in methylene chloride containing small amounts of methanol and acidified with ethereal HCl. The hydrochloride salt was precipitated by ether dilution, filtered, rinsed with fresh ether, and dried in vacuo (60° C., 10 pascal, 18 h) to yield a white solid, mp 177°–183° C. The analysis for dihydrochloride was not in agreement with calculated; 1H NMR and MS of salt were completely consistent with the proposed structure.

The starting pyridine aldehyde derivative was prepared as follows:

a. 1-(9,10-Dihydro-9,10-methanoanthracen-9-ylmethyl)-4-(5-formyl-3-pyridyl)piperidin-4-ol To a cooled solution (−78° C.) of oxalyl chloride (0.597 mL, 6.84 mmol, 2 eq) in methylene chloride (15 mL) under nitrogen was added freshly distilled dimethylsulfoxide (0.971 mL, 13.68 mmol, 4 eq). After 10 min 1-(9,10-dihydro-9,10-methanoanthracen-9-ylmethyl)-4-(5-(hydroxymethyl)-3-pyridyl)piperidin-4-ol (described in example 70) (1.41 g, 3.42 mmol) was added as a dimethylsulfoxide solution (15 mL). The reaction was stirred at −78° C. for 1 h prior to the addition of triethylamine (3.81 mL, 27.4 mmol, 8 eq). The cooling bath was removed and the reaction warmed to room temperature over 2 h. Water (35 mL) was added to quench the reaction and the product extracted into methylene chloride (3×20 mL). Combined organic extracts were dried over anhydrous magnesium sulfate, filtered, and reduced to a white solid. The reaction product was purified by flash chromatography over silica gel (65 mL, eluent 10% hexane in ethyl acetate ramped to straight ethyl acetate) to yield 1.04 g (74%) of the title compound. TLC analysis ($R_f$ 0.25, 10% hexane in ethyl acetate). MS (CI, CH4) m/z 411 (M+1,100), 439 (M+29,14), 393 (18), 260 (7), 219 (10), 206 (25), 169 (12)

EXAMPLE 74

1-(9,10-Dihydro-9,10-methanoanthracen-9-ylmethyl)-4-(5-(methoxycarbonyl)-3-pyridyl)piperidin-4-ol To a heterogeneous solution of 1-(9,10-dihydro-9,10-methanoanthracen-9-ylmethyl)-4-(5-(4-methyl-2,6,7-trioxabicyclo[2.2.2]oct-1-yl)-3-pyridyl)piperidin-4-ol (0.970 g, 1.90 mmol) in methanol (5 mL) under nitrogen was added sulfuric acid (0.21 mL, 2 eq). The suspension dissolved as the acid was added. The reaction was stirred for 24 h and basified with 2.5N NaOH (25 mL). The aqueous phase was extracted with ethyl acetate (3×20 mL). Combined organic extracts were dried over anhydrous magnesium sulfate, filtered, and reduced to an oil. The reaction product was purified by flash chromatography over silica gel (65 mL, eluent: 20% hexane in ethyl acetate) to yield 0.560 g (67%) of the title compound as a white solid. TLC analysis ($R_f$ 0.21, 20% hexane in ethyl acetate). 1H NMR (CDCl$_3$, 300 MHz) 9.10 (d, J=1.8 Hz, 1H), 8.93 (d, J=2.3 Hz, 1H), 8.38 (t, J=2.1Hz, 1H), 7.27 (m, 2H), 7.18 (m, 2H), 6.95 (m, 4H), 4.29 (br s, 1H), 3.95 (s, 3H), 3.49 (s, 2H), 2.95 (m, 2H), 2.73 (m, 2H), 2.63 (s, 2H), 2.15 (m, 2H), 1.76 (m, 2H) MS (CI, CH4) m/z 441 (M+1,100), 469 (M+29,15), 423 (11), 145 (9), 103 (11), 85 (20) The free base was dissolved in ether containing methylene chloride and acidified with ethereal HCl. The hydrochloride salt was precipitated with ether dilution, filtered, rinsed with fresh ether and dried in vacuo (60° C., 10 pascal, 18 h) to yield a white solid, mp 243°–247° C. (dec).

Analysis for $C_{28}H_{28}N_2O_3 \cdot 2HCl \cdot H_2O$: Calculated: C, 63.28; H, 6.07; N, 5.27 Found: C, 63.24; H, 5.90; N, 5.03

The starting orthoester was prepared as follows:

a. 3-Methyl-3-oxetanemethyl-5-bromonicotinate

To a toluene suspension (50 mL) of 5-bromonicotinic acid (5.02 g, 24.9 mmol) was added thionyl chloride (2.0 mL, 27.4 mmol, 1.1 eq). The suspension was heated to reflux monitoring gas evolution with a mineral oil bubbler. After 45 min the system became homogeneous and achieved a steady state condition with respect to gas evolution. The reaction was cooled to room temperature. Excess thionyl chloride and the solvent were removed in vacuo and replaced with methylene chloride (50 mL). The oxetane methanol (2.73 mL, 27.4 mmol, 1.1 eq) was added followed by triethylamine (8.70 mL, 62.3 mmol, 2.5 eq). A significant amount of precipitate forms as the reaction was stirred a room temperature under nitrogen. After 24 h excess reagent was quenched with water (40 mL) and the aqueous phase extracted with methylene chloride (2×50 mL). Combined organic extracts were dried over anhydrous magnesium sulfate, filtered, and reduced to an oil. The reaction product was purified by flash chromatography over silica gel (250 mL, eluent: 20% ethyl acetate in hexane) to yield 5.10 g (72%) of the title compound as a highly crystalline white solid. TLC analysis ($R_f$ 0.15, 20% ethyl acetate in hexane). MS (CI, CH4) m/z 286 (M+1,100), 288 (99), 314 (M+29, 15), 316 (15)

b. 3-Bromo-5-(4-methyl-2,6,7-trioxabicyclo[2.2.2]octyl)pyridine

A methylene chloride solution (30 mL) of 3-methyl-3-oxetanemethyl 5-bromonicotinate (described in example 74a) (2.50 g, 8.73 mmol) was cooled to 0° C. under nitrogen. Boron trifluoride etherate (1.34 mL, 10.9 mmol, 1.25 eq) was added and the resulting solution stirred at 0° C. for 25 h. The reaction was quenched with excess triethylamine and diluted with diethyl ether to precipitate amine salts. The solution was filtered over silica gel (20 g, pretreated with 1% triethylamine in ether) to remove baseline impurities. The reaction product was purified by flash chromatography over silica gel (150 mL, eluent: 15% ethyl acetate in hexane) to yield 2.02 g (81%) of the title compound as a colorless oil. TLC analysis ($R_f$ 0.29, 20% ethyl acetate in hexane containing 1% triethylamine). MS (CI, CH4) m/z 286 (M+1, 100), 288 (99), 222 (19), 314 (M+29,19), 316 (19)

c. 1-(9,10-Dihydro-9,10-methanoanthracen-9-ylmethyl)-4-(5-(4-methyl-2,6,7-trioxabicyclo[2.2.2]-1-octyl)-3-pyridyl)piperidin-4-ol Using a procedure similar to that described in example 1 except starting with 1-(9,10-dihydro-9,10-methanoanthracen-9-ylmethyl)-4-piperidinone (described in example 5d) and employing 3-bromo-5-(4-methyl-2,6,7-trioxabicyclo[2.2.2]octyl)pyridine (described in example 74b), the title compound was formed in 75% yield as a white solid. TLC analysis ($R_f$ 0.25, 20% hexane in ethyl acetate) MS (CI, CH4) m/z 511 (M+1,100), 539 (M+29,16), 493 (16)

EXAMPLE 75

1-(9,10-Dihydro-9,10-methanoanthracen-9-ylmethyl)-4-(5-(N-propylcarboxamido)-3-pyridyl)piperidin-4-ol A solution of 1-(9,10-dihydro-9,10-methanoanthracen-9-ylmethyl)-4-(5-(methoxycarbonyl)-3-pyridyl)piperidin-4-ol (described in example 74) (0.560 g, 1.27 mmol) in propyl amine (5 mL) was heated to reflux for 68 h under nitrogen. The solvent was removed in vacuo to yield an oil. The crude reaction product was purified by flash chromatography over silica gel (35 mL, eluent: ethyl acetate) to yield 0.450 g (76%) of the title compound. TLC analysis ($R_f$ 0.19, ethyl acetate). 1H NMR (CDCl$_3$, 250 MHz) 8.84 (d, J=2.2 Hz, 1H), 8.81 (d, J=2.0 Hz, 1H), 7.26 (m, 2H), 7.19 (m, 2H), 6.94 (m, 4H), 4.29 (br s, 1H), 3.49 (s, 2H), 3.42 (m, 2H), 2.95 (m, 2H), 2.72 (m, 2H), 2.62 (d, J=1.4 Hz, 2H), 2.14 (m, 2H), 1.75 (m, 2H), 1.64 (m, 2H), 0.99 (t, J=7.5 Hz, 3H) MS (CI, CH4) m/z 468 (M+1,100), 496 (M+29,16), 450 (14) The free base was dissolved in methanol, acidified with ethereal HCl and diluted with ether to precipitate the salt. The hydrochloride salt was filtered, rinsed with fresh ether and dried in vacuo (60° C., 10 pascal, 18 h) to yield a white solid, mp 205°–208° C.

Analysis for $C_{30}H_{33}N_3O_2 \cdot 2HCl \cdot 0.4H_2O$: Calculated: C, 65.79; H, 6.59; N, 7.67 Found: C, 65.70; H6.64; N, 7.47

EXAMPLE 76

1-(9,10-Dihydro-9,10-methanoanthracen-9-ylmethyl)-4-(2-N,N-dimethylsulfamoylphenyl)piperidin-4-ol A solution of n-butyllithium (1.21 mL of a 2.29M solution in hexanes, 2.77 mmol) in tetrahydrofuran (10 mL) was cooled to −30° C. and treated with a solution of N,N-dimethylbenzenesulfonamide (510 mg, 2.77 mmol) in tetrahydrofuran (5 mL). The mixture was warmed to 0° C. and stirred for 20 min, then was cooled to −30° C. and treated with a solution of 1-(9,10-dihydro-9,10-methanoanthracen-9-ylmethyl)-4-piperidinone (described in example 5d) (700 mg, 2.31 mmol) in tetrahydrofuran (5 mL). The mixture was warmed to room temperature, stirred for 0.5 h, then was poured into 1N aqueous sodium hydroxide (25 mL). The mixture was extracted with chloroform (3×50 mL). The organic extracts were washed with brine (50 mL), combined, dried over anhydrous potassium carbonate, filtered, and evaporated to leave an amber foam (1.3 g). Purification by flash chromatography (eluent: 6:1-3:1 hexane/acetone) afforded a white powder (502 mg). This solid was dissolved in diethyl ether and treated with ethereal hydrogen chloride to afford the hydrochloride salt of the title compound (486 mg, 0.92 mmol, 40%) as a white powder, mp 220°–223° C. elemental.

Analysis for $C_{29}H_{32}N_2O_3S \cdot HCl \cdot 0.2H_2O$: Calculated: C, 65.77; H, 6.38; N, 5.29 Found: C, 65.92; H, 6.35; N, 5.12

1H NMR (D$_6$-DMSO, D-TFA): 7.70–7.35 (m, 8H), 7.03 (m, 4H), 4.49 (s, 3H), 3.75 (m, 2H), 3.57 (m, 2H), 2.96 (s, 6H), 2.76 (s, 2H), 2.46 (m, 2H), 2.32 (m, 2H) MS (CI, CH4) m/z 490 (36), 489 (M+1,100), 471 (11)

EXAMPLE 77

1-(9,10-Dihydro-9,10-methanoanthracen-9-ylmethyl)-4-(2-N-methylsulfamoylphenyl)piperidin-4-ol By a procedure similar to that described in example 76 except using N-methylbenzenesulfonamide in the directed lithiation reaction, the title compound was obtained as a white powder (42%), mp 179°–182° C. elemental Analysis for $C_{28}H_{30}N_2O_3S$: Calculated: C, 70.86; H, 6.37; N, 5.90 Found: C, 60.73; H, 6.42; N, 5.89

1H NMR (D$_6$-DMSO): 7.98 (d, J=6.9 Hz, 1H), 7.65 (d, J=8.3 Hz, 1H), 7.55 (t, J=7.2 Hz, 1H), 7.43 (t, J=7.2 Hz, 1H), 7.26 (m, 4H), 6.89 (m, 5H), 5.44 (s, 1H), 4.31 (s, 1H), 3.42 (s, 2H), 2.78 (m, 4H), 2.50 (s, 3H), 2.45 (s, 2H), 2.02 (br s, 4H) MS (CI, CH4) m/z 476 (31), 475 (M+1,100), 457 (18)

EXAMPLE 78

1-(9,10-Dihydro-9,10-methanoanthracen-9-ylmethyl)-4-(2-N,N-dimethylsulfamoyl-5-methoxyphenyl)piperidin-4-ol By a procedure similar to that described in example 76 except using N,N-dimethyl-4-methoxybenzenesulfonamide in the directed lithiation reaction, the title compound was obtained as a white powder (26%), mp 101°–103° C. elemental Analysis for $C_{30}H_{34}N_2O_4S$: Calculated: C, 69.42; H, 6.61; N, 5.40 Found: C, 69.25; H, 6.48; N, 5.30

1H NMR (D$_6$-DMSO): 7.69 (d, J=8.9 Hz, 1H), 7.23 (m, 5H), 6.91 (m, 5H), 5.05 (s, 1H), 4.31 (s, 1H), 3.83 (s, 3H), 3.41 (s, 2H), 2.79 (s, 6H), 2.72 (m, 4H), 2.49 (s, 2H), 2.12 (m, 2H), 1.90 (d, J=12.4 Hz, 2H) MS (CI, CH4) m/z 520 (34), 519 (M+1,100), 518 (15), 501 (11)

EXAMPLE 79

1-(9,10-Dihydro-9,10-methanoanthracen-9-ylmethyl)-4-(2-N-methylsulfamoyl-5-methoxyphenyl)piperidin-4-ol By a procedure similar to that described in example 76 except using N-methyl-4-methoxybenzenesulfonamide in the directed lithiation reaction, the title compound was obtained as a white powder (23%), mp 209°–211° C. elemental Analysis for $C_{29}H_{32}N_2O_4S$: Calculated: C, 69.02; H, 6.39; N, 5.55 Found: C, 69.08; H, 6.43; N, 5.46

1H NMR (D$_6$-DMSO): 7.93 (d, J=8.9 Hz, 1H), 7.26 (m, 4H), 7.05 (d, J=2.0 Hz, 1H), 6.90 (m, 6H), 5.44 (s, 1H), 4.31 (s, 1H), 3.81 (s, 3H), 3.41 (s, 2H), 2.72 (m, 4H), 2.50 (s, 2H), 2.41 (d, J=4.5 Hz, 3H), 2.03 (m, 4H) MS (CI, CH4) m/z 506 (35), 505 (M+1,100)

EXAMPLE 80

1-(9,10-Dihydro-9,10-methanoanthracen-9-ylmethyl)-4-(2-N-propylsulfamoyl-5-methoxyphenyl)piperidin-4-ol By a procedure similar to that described in example 76 except using N-propyl-4-methoxybenzenesulfonamide in the directed lithiation reaction, the title compound was obtained as a white powder (34%), mp 169°–170° C. elemental Analysis for $C_{31}H_{36}N_2O_4S$: Calculated: C, 69.90; H, 6.81; N, 5.26 Found: C, 69.79; H, 6.92; N, 5.29

1H NMR (D$_6$-DMSO): 7.96 (d, J=8.8 Hz, 1H), 7.28 (m, 4H), 7.05 (m, 1H), 6.98 (m, 4H), 5.51 (s, 1H), 4.32 (s, 1H), 3.82 (s, 3H), 3.42 (s, 2H), 2.68 (m, 6H), 2.51 (s, 2H), 2.03 (m, 4H), 1.41 (m, 2H), 0.82 (t, J=7.4 Hz, 3H) MS (CI, CH4) m/z 506 (35), 505 (M+1,100)

EXAMPLE 81

1-(9,10-Dihydro-9,10-methanoanthracen-9-ylmethyl)-4-(2-N-propylsulfamoylphenyl)piperidin-4-ol By a procedure similar to that described in example 76 except using N-propylbenzenesulfonamide in the directed lithiation reaction, the title compound was obtained as a white powder (54%), mp 131°–133° C. elemental Analysis for $C_{30}H_{34}N_2O_3S.0.25H_2O$: Calculated: C, 71.04; H, 6.85; N, 5.52 Found: C, 71.03; H, 6.82; N, 5.69

1H NMR (D$_6$-DMSO): 8.01 (m, 1H), 7.63 (d, J=7.8 Hz, 1H), 7.54 (t, J=6.5 Hz, 1H), 7.42 (t, J=7.1Hz, 1H), 7.26 (m, 4H), 6.92 (m, 4H), 4.31 (s, 1H), 3.41 (s, 2H), 3.31 (m, 2H), 2.73 (m, 6H), 2.03 (br s, 4H), 1.41 (m, 2H), 0.81 (t, J=7.3 Hz) MS (CI, CH4) m/z 504 (35), 503 (M+1,100)

EXAMPLE 82

1-(9,10-Dihydro-9,10-methanoanthracen-9-ylmethyl)-4-(2-pyrrolidinylsulfamoylphenyl)piperidin-4-ol By a procedure similar to that described in example 76 except using pyrrolidinylbenzenesulfonamide in the directed lithiation reaction, the title compound was obtained as a white powder (15%), mp 203°–204° C. elemental Analysis for $C_{31}H_{34}N_2O_3$: Calculated: C, 72.34; H, 6.66; N, 5.44 Found: C, 72.22; H, 6.72; N, 5.41

1H NMR (D$_6$-DMSO): 7.76 (m, 2H), 7.56 (t, J=7.7 Hz, 1H), 7.45 (t, J=7.6 Hz, 1H), 7.23 (m, 4H), 6.92 (m, 4H), 5.01 (s, 1H), 4.31 (s, 1H), 3.40 (s, 2H), 3.30 (m, 4H), 2.73 (m, 4H), 2.49 (s, 2H), 2.09 (m, 2H), 1.88 (m, 6H) MS (CI, CH4) m/z 516 (33), 515 (M+1,100).

EXAMPLE 83

1-(9,10-Dihydro-9,10-methanoanthracen-9-ylmethyl)-4-(2-N-ethylsulfamoylphenyl)piperidin-4-ol By a procedure similar to that described in example 76 except using N-ethylbenzenesulfonamide in the directed lithiation reaction, the title compound was obtained as a white powder (52%), mp 84°–185° C. elemental Analysis for $C_{29}H_{32}N_2O_3S.0.2H_2O$: Calculated: C, 71.28; H, 6.60; N, 5.73 Found: C, 70.90; H, 6.66; N, 5.79

1H NMR (D$_6$-DMSO): 9.02 (d, J=7.9 Hz, 1H), 7.64 (d, J=7.9 Hz, 1H), 7.55 (t, J=7.2 Hz), 7.44 (t, J=7.2 Hz), 7.26 (m, 4H), 7.08 (m, 1H), 6.93 (m, 4H), 5.50 (s, 1H), 4.32 (s, 1H), 3.42 (s, 2H), 2.82 (m, 6H), 2.51 (s, 2H), 2.04 (s, 4H), 1.02 (t, J=7.0 Hz, 3H) MS (CI, CH4) m/z 490 (31), 489 (M+1,100), 471 (11).

EXAMPLE 84

1-(2-Chloro-9,10-dihydro-9,10-methanoanthracen-9-ylmethyl)-4-(2-N- methylsulfamoyl-5-methoxyphenyl)piperidin-4-ol By a procedure similar to that described in example 76 except using N-methyl-4-methoxybenzenesulfonamide in the directed lithiation reaction, and 1-(2-chloro-9,10-methanoanthracen-9-ylmethyl)-4-piperidone (described in example 1m), the title compound was obtained as a white powder (29%), mp 179°–182° C. elemental Analysis for $C_{29}H_{31}ClN_2O_4S$: Calculated: C, 64.61; H, 5.79; N, 5.19 Found: C, 64.30; H, 5.90; N, 5.18

1H NMR (D$_6$-DMSO): 7.94 (d, J=8.8 Hz, 1H), 7.26 (m, 4H), 7.05 (s, 1H), 6.97 (m, 4H), 6.81 (q, J=5.2 Hz, 1H), 5.45 (s, 1H), 4.30 (s, 1H), 3.82 (s, 3H), 3.41 (s, 2H), 2.78 (m, 4H), 2.50 (s, 2H), 2.42 (d, J=5.2 Hz, 3H), 2.04 (s, 4H) MS (CI, CH4) m/z 542 (13), 541 (43), 540 (38), 539 (M+1,100)

EXAMPLE 85

1-(2-Chloro-9,10-dihydro-9,10-methanoanthracen-9-ylmethyl)-4-(2-N,N-dimethylsulfamoyl-5-methoxyphenyl)piperidin-4-ol By a procedure similar to that described in example 76 except using N,N-dimethyl-4-methoxybenzenesulfonamide in the directed lithiation reaction, and 1-(2-chloro-9,10-methanoanthracen-9-ylmethyl)-4-piperidone (described in example 1m), the title compound was obtained as a white powder (27%), mp 190°–191° C. elemental Analysis for $C_{30}H_{33}ClN_2O_4S$: Calculated: C, 65.15; H, 6.01; N, 5.06 Found: C, 64.86; H, 5.98; N, 4.80

1H NMR (D$_6$-DMSO): 7.69 (d, J=8.9 Hz, 1H), 7.23 (m, 5H), 6.97 (m, 4H), 5.05 (s, 1H), 4.34 (s, 1H), 3.82 (s, 3H), 3.39 (br s, 2H), 2.79 (br m, 10H), 2.50 (s, 2H), 2.13 (m, 2H), 1.88 (m, 2H) MS (CI, CH4) m/z 556 (10), 555 (34), 554 (31), 553 (M+1,100), 535 (13)

EXAMPLE 86

1-((9S,10S)-2-Chloro-9,10-dihydro-9,10-methanoanthracen-9-ylmethyl)-4-(2-N-methylsulfamoyl-5-methoxyphenyl)piperidin-4-ol By a procedure similar to that described in example 76 except using N-methyl-4-methoxybenzenesulfonamide in the directed lithiation reaction, and 1-((9S,10S)-2-chloro-9,10-dihydro-9,10-methanoanthracen-9-ylmethyl)-4-piperidone, the title compound was obtained as a white powder (44%), mp 140°–142° C. elemental Analysis for $C_{29}H_{31}ClN_2O_4S$: Calculated: C, 64.18; H, 5.83; N, 5.16 Found: C, 64.14; H, 5.94; N, 4.19

1H NMR (D$_6$-DMSO): 7.94 (d, J=8.8 Hz, 1H), 7.25 (m, 4H), 7.05 (d, J=2.5 Hz, 1H), 6.98 (m, 4H), 6.80 (q, J=5.1Hz, 1H), 5.43 (s, 1H), 4.34 (s, 1H), 3.81 (s, 3H), 3.40 (s, 2H), 2.78 (m, 4H), 2.50 (s, 2H), 2.42 (d, J=5.2 Hz, 3H), 2.04 (s, 4H) MS (CI, CH4) m/z 542 (14), 541 (38), 540 (26), 539 (M+1,100)

EXAMPLE 87

1-(2,7-Dichloro-9,10-dihydro-9,10-methanoanthracen-9-ylmethyl)-4-(3-pyridyl) piperidin-4-ol To a tetrahydrofuran solution (10 mL) of 1-(2,7-dichloro-9,10-dihydro-9,10-methanoanthracen-9-ylcarbonyl)-4-(3-pyridyl)piperidin-4-ol (280 mg, 0.602 mmol) under nitrogen was added boron trifluoride etherate (0.306 mL, 2.41 mmol, 4 eq) and borane dimethyl sulfide complex (10M, 0.250 mL, 4 eq). The reaction was then heated to reflux for 24 h. After this period of time, a solution of methanol and 3N HCl (25 mL, 1:1 by volume) was added and reflux was continued an additional 20 min. The reaction was cooled to room temperature and basified with 2.5N NaOH (20 mL). The aqueous phase was extracted with ethyl acetate (3×20 mL). Combined organic extracts were dried over anhydrous magnesium sulfate, filtered, and reduced to an oil. The reaction product was purified by flash chromatography over silica gel (30 mL, eluent: ethyl acetate) to yield 190 mg (70%) of an off-white foam. TLC analysis ($R_f$ 0.19, ethyl acetate). 1H NMR (CDCl$_3$, 300 MHz) 8.76 (d, J=2.1Hz, 1H), 8.50 (dd, J=1.5, 4.7 Hz, 1H), 7.80 (dt, J=2.0, 8.0 Hz, 1H), 7.27 (m, 1H), 7.16 (m, 4H), 6.92 (dd, J=1.8, 7.8 Hz, 2H), 4.25 (br s, 1H), 3.42 (br s, 2H), 2.90 (m, 2H), 2.76 (m, 2H), 2.63 (br s, 2H), 2.13 (m, 2H), 1.80 (m, 2H) MS (CI, CH4) m/z 451 (M+1,100), 453 (60), 479 (M+29,16), 481 (11), 433 (17), 435 (11) The free base was dissolved in methanol/methylene chloride, acidified with ethereal HCl and the hydrochloride salt precipitated with ether dilution. The hydrochloride salt was filtered, rinsed with fresh ether and dried in vacuo (60° C., 10 pascal, 18 h) to yield a white solid, mp 252°–254° C. (dec).

Analysis for C$_{26}$H$_{25}$Cl$_2$N$_2$O.2.1HCl.2H$_2$O: Calculated: C, 55.37; H, 5.38; N, 4.97 Found: C, 55.26; H, 4.96; N, 4.70

The starting amide was prepared as follows:

a. 1-(2,7-Dichloro-9,10-dihydro-9,10-methanoanthracen-9-ylcarbonyl) -4-(3-pyridyl)piperidin-4-ol To a toluene solution (10 mL) of 2,7-dichloro-9,10-dihydro-9,10-methano-9-anthracenecarboxylic acid (described in example 35e) (0.363 g, 1.19 mmol) was added thionyl chloride (0.087 mL, 1.2 mmol, 1 eq). The reaction was heated to reflux for 2 h monitoring gas evolution with a mineral oil bubbler. The toluene was removed, replaced with fresh toluene and stripped to dryness. This procedure was repeated two times. The residue was dissolved in tetrahydrofuran (10 mL). To that solution was added triethylamine (0.17 mL, 1.2 mmol, 1 eq) and 4-hydroxy-4-(3-pyridyl)piperidine (0.212 g, 1.2 mmol, 1 eq). The tetrahydrofuran solution was heated to reflux for 18 h, cooled to room temperature and poured into ethyl acetate (200 mL). The organic phase was washed with saturated sodium bicarbonate (100 mL), dried over anhydrous sodium sulfate, filtered, and reduced to an oil. The reaction product was purified by flash chromatography over silica gel (50 mL, eluent: 10% methanol in methylene chloride increasing to 20% methanol in methylene chloride) to yield 0.29 g (52%) of a white solid. TLC analysis ($R_f$ 0.23, 10% methanol in diethyl ether). MS (CI, CH4) m/z 465 (M+1,100), 447 (16), 97 (28), 79 (64)

The starting pyridylpiperidine was prepared as follows:

b. 1-(Carbobenzyloxy)piperidin-4-ol

A solution of 4-hydroxypiperidine (25.0 g, 0.247 mol) in methylene chloride (2000 mL) was cooled to 0° C. under nitrogen with overhead stirring. Triethylamine (86.1 mL, 0.618 mol, 2.5 eq) was added followed by benzyl chloroformate (35.3 mL, 0.247 mol, 1.0 eq). The reaction was warmed to room temperature over 1 h and maintained at this temperature for 5 h. A significant amount of amine hydrochloride precipitates in the course of the procedure. The organic phase was washed with 3N HCl (3×250 mL), dried over anhydrous sodium sulfate and filtered. The solvent was removed in vacuo to yield 47.0 g (81%) of the title compound as an oil. The product did not require any addition purification prior to the Swern oxidation. TLC analysis ($R_f$ 0.17, 50% ethyl acetate in hexane). MS (CI, CH4) m/z 236 (M+1,42), 218 (4), 192 (10), 181 (9), 174 (15), 91 (100)

c. 1-Carbobenzyloxy-4-piperidone

To a cooled solution (−78° C.) of oxalyl chloride (freshly distilled, 18.2 mL, 0.21 mol, 1.5 eq) in methylene chloride (1400 mL) under nitrogen was added freshly distilled dimethylsulfoxide (29.6 mL, 0.42 mol, 3.0 eq). The solution was stirred for 10 min after which a methylene chloride solution (150 mL) of 1-carbobenzyloxypiperidin-4-ol (described in example 87b) (32.76 g, 0.139 mmol) was added via cannula transfer. The solution was maintained at −78° C. for 30 min Triethylamine (116 mL, 0.83 mol, 6.0 eq) was added and the reaction warmed to room temperature over 1.5 h. Once at room temperature, the reaction was quenched with 3N HCl (400 mL). The organic phase was washed with 3N HCl (2×400 mL), 2.5N NaOH (2×400 mL) and saturated brine (1×400 mL). The methylene chloride phase was dried over anhydrous magnesium sulfate, filtered over 100 g of silica gel, and reduced to an oil. The procedure resulted in 23.8 g (73%) of the title compound which did not require any additional purification. 1H NMR (CDCl$_3$, 300 MHz) 7.34 (m, 5H), 5.18 (s, 2H), 3.80 (t, J=6.2 Hz, 4H), 2.46 (br t, 4H) MS (CI, CH4) m/z 234 (M+1,39), 262 (M+29,10), 91 (100)

d. 1-Carbobenzyloxy-4-(3-pyridyl)piperidin-4-ol

To a cooled solution (−78° C.) of n-butyllithium (2.0M in hexane, 12.9 mL, 28.3 mmol, 1.2 eq) in tetrahydrofuran (200 mL) under nitrogen was added 3-bromopyridine (2.27 mL, 23.6 mmol, 1.1 eq). The solution became a dark green color as the pyridine was added. The reaction was stirred at this temperature for 1 h, at which time 1-carbobenzyloxy-4-piperidone (described in example 87c) (5.00 g, 21.4 mmol) was added as a tetrahydrofuran solution (20 mL). The cooling bath was removed and the reaction warmed to room temperature, stirring at that temperature for 18 h. The reaction was quenched by the addition of water (125 mL) and the aqueous phase extracted with ethyl acetate (3×75 mL). Combined organic extracts were dried over anhydrous magnesium sulfate, filtered, and reduced to an oil. The reaction product was purified by flash chromatography over silica gel (300 mL, eluent: ethyl acetate) to yield 5.00 g (75%) of the title compound as an oil. TLC analysis ($R_f$ 0.10, ethyl acetate). MS (CI, CH4) m/z 313 (M+1,100), 341 (M+29,15), 295 (15)

e. 4-(3-Pyridyl)piperidin-4-ol

To a solution of 1-carbobenzyloxy-4-(3-pyridyl) piperidin-4-ol (described in example 87d) (3.17 g, 10.2 mmol) in ethanol (100 mL) was added 10% palladium on carbon (2.0 g). This was followed by cyclohexene (50 mL) in large excess. The reaction was heated to reflux under nitrogen for 2 h. The suspension was cooled, filtered and the catalyst rinsed with fresh ethanol. The filtrate was reduced in vacuo to yield 1.70 g (94%) of an off-white solid which did not require any additional purification. 1H NMR (D$_6$-DMSO, 300 MHz) 8.68 (d, J=2.0 Hz, 1H), 8.42 (dd, J=1.5, 4.6 Hz, 1H), 7.83 (ddd, J=1.9, 2.1, 4.0 Hz, 1H), 7.35 (dd, J=4.8, 8.0 Hz, 1H), 2.97 (ddd, J=2.3, 12.2 Hz, 2H), 2.78 (m, 2H), 1.86 (ddd, J=4.5, 12.9 Hz, 2H), 1.56 (m, 2H), 2.50 (m, 1H) MS (CI, CH4) m/z 179 (M+1,100), 207 (M+29,16), 161 (39)

Examples 88, 90, and 91 illustrate a specific reaction sequence for making a compound of formula I wherein the values corresponding to X and Y are halo and hydroxy, which is a precursor for making compounds of formula I which are 2-halo-7-alkoxy derivatives.

EXAMPLE 88

1-(2-Chloro-7-nitro-9,10-dihydro-9,10-methanoanthracen-9-ylmethyl)-4-(3-pyridyl)piperidin-4-ol Using a procedure similar to that described in example 87 except starting with the 1-(2-chloro-7-nitro-9,10-dihydro-9,10-methanoanthracen-9-ylcarbonyl)-4-(3-pyridyl)piperidin-4-ol, the title compound was formed in 84% yield as a white solid, mp 207°–210° C. (dec). free base: 1H NMR ($D_6$-DMSO, 300 MHz) 8.68 (d, J=2.1Hz, 1H), 8.41 (d, J=3.5 Hz, 1H), 8.03 (d, J=1.7 Hz, 1H), 7.92 (dd, J=2.00, 8.0 Hz, 1H), 7.84 (dd, J=1.6, 3.8 Hz, 1H), 7.56 (d, J=8.0 Hz, 1H), 7.35 (m, 3H), 7.02 (dd, J=1.7, 7.8 Hz, 1H), 5.07 (br s, 1H), 4.56 (br s, 1H), 3.51 (d, J=3.6 Hz, 2H), 2.80 (m, 4H), 2.64 (br s, 2H), 1.93 (m, 2H), 1.61 (m, 2H) MS (CI, CH4) m/z 462 (M+1, 100), 464 (38), 490 (M+29,24), 444 (14), 432 (13) hydrochloride salt:

Analysis for $C_{26}H_{24}ClN_3O_3.2HCl.0.5H_2O$: Calculated: C, 57.42; H, 5.00; N, 7.72 Found: C, 57.71; H, 5.70; N, 6.50

The starting amide was prepared as follows:

a. 2-Chloro-7-nitro-9,10-dihydro-9,10-methano-9-anthracenecarboxylic acid

Using a procedure similar to that described in example 35e except starting with methyl 2-chloro-7-nitro-9,10-dihydro-9,10-methano-9-anthracenecarboxylate (described in example 35b), the title compound was formed in quantitative yield. No additional characterization was necessary prior to the coupling reaction.

b. 1-(2-Chloro-7-nitro-9,10-dihydro-9,10-methanoanthracen-9-ylcarbonyl)-4-(3-pyridyl)piperidin-4-ol Using a procedure similar to that described in example 87a except starting with 2-chloro-7-nitro-9,10-dihydro-9,10-methano-9-anthracenecarboxylic acid (described in example 89a), the title compound was formed in 59% yield as an off-white foam. TLC analysis ($R_f$ 0.20, ethyl acetate) MS (CI, CH4) m/z 476 (M+1,100), 478 (33), 504 (M+29, 21), 446 (25), 458 (30)

EXAMPLE 89

1-(2-Amino-7-chloro-9,10-dihydro-9,10-methanoanthracen-9-ylmethyl)-4-(3-pyridyl)piperidin-4-ol Using a procedure similar to that described in example 87 except starting with the 1-(2-amino-7-chloro-9,10-dihydro-9,10-methanoanthracen-9-ylcarbonyl)-4-(3-pyridyl)piperidin-4-ol, the title compound was formed in 88% yield as an off-white solid, mp 275°–278° C. (dec). free base: 1H NMR ($CDCl_3$, 300 MHz) 8.76 (d, J=2.1 Hz, 1H), 8.50 (dd, J=1.6, 4.8 Hz, 1H), 7.80 (dt, J=1.9, 8.1 Hz, 1H), 7.27 (m, 1H), 7.11 (m, 2H), 7.00 (d, J=7.7 Hz, 1H), 6.88 (dd, J=1.8, 7.7 Hz, 1H), 6.60 (d, J=2.1Hz, 1H), 6.24 (dd, J=2.0, 7.6 Hz, 1H), 4.16 (br s, 1H), 3.38 (br s, 2H), 2.90 (m, 2H), 2.70 (m, 2H), 2.56 (m, 2H), 2.10 (m, 2H), 1.76 (m, 2H) MS (CI, CH4) m/z 432 (M+1,53), 434 (21), 460 (M+29,1), 414 (7), 97 (31), 79 (100) hydrochloride salt:

Analysis for $C_{26}H_{26}ClN_2O.3HCl.0.5H_2O$: Calculated: C, 56.74; H, 5.49; N, 7.63 Found: C, 57.02; H, 5.95; N, 7.10

The starting amide was prepared as follows:

a. 2-Amino-7-chloro-9,10-dihydro-9,10-methano-9-anthracenecarboxylic acid

Using a procedure similar to that described in example 35e except starting with methyl 2-amino-7-chloro-9,10-dihydro-9,10-methano-9-anthracenecarboxylate (described in example 35c), the title compound was formed in 51% yield as a white solid. TLC analysis ($R_f$ 0.23, 20% ethyl acetate in hexane). MS (CI, CH4) m/z 300 (M+1,100), 302 (37), 328 (M+29,17), 264 (36), 227 (91), 201 (55)

EXAMPLE 90

1-(2-Chloro-7-hydroxy-9,10-dihydro-9,10-methanoanthracen-9-ylmethyl)-4-(3-pyridyl)piperidin-4-ol Using a procedure similar to that described in example 87 except starting with 1-(2-chloro-7-hydroxy-9,10-dihydro-9,10-methanoanthracen-9-ylcarbonyl)-4-(3-pyridyl)piperidin-4-ol, the title compound was formed in 55% yield as a white solid, mp 224°–228° C. (dec). free base: 1H NMR ($D_6$-DMSO, 300 MHz) 9.15 (s, 1H), 8.69 (br s, 1H), 8.41 (d, J=4.4 Hz, 1H), 7.83 (d, J=8.0 Hz, 1H), 7.31 (dd, J=4.6, 7.9 Hz, 1H), 7.25 (m, 2H), 7.02 (d, J=7.8 Hz, 1H), 6.94 (dd, J=1.6, 7.6 Hz, 1H), 6.70 (d, J=1.8 Hz, 1H), 6.27 (dd, J=1.8, 7.7 Hz, 1H), 5.05 (br s, 1H), 4.22 (br s, 1H), 2.75 (m, 2H), 2.59 (m, 1H), 2.48 (m, 3H), 1.92 (m, 2H), 1.61 (m, 2H) MS (CI, CH4) m/z 433 (M+1,100), 435 (36), 461 (M+29,22), 415 (16) hydrochloride: analysis for dihydrochloride was not in agreement with calculated; 1H NMR and MS of salt completely consistent.

The starting amide was prepared as follows:

a. Methyl 2-chloro-7-hydroxy-9,10-dihydro-9,10-methano-9-anthracenecarboxylate

To boron trifluoride etherate (0.413 mL, 3.36 mmol, 1.5 eq) cooled to –15° C. under nitrogen was added a solution of methyl 2-amino-7-chloro-9,10-dihydro-9,10-methano-9-anthracenecarboxylate (described in example 35c) (670 mg, 2.24 mmol) in methylene chloride (5 mL). This was followed by t-butyl nitrite (0.320 mL, 2.69 mmol, 1.2 eq) resulting in a precipitate and a dark blue-green solution color. After 10 min at –15° C., the reaction was warmed to 0° C. and stirred for additional 20 min The diazonium salt was precipitated by pentane dilution (100 mL). The precipitate was filtered and rinsed with cold diethyl ether to recover 650 mg of the crude salt. The diazonium salt was added to a solution of potassium carbonate (155 mg, 0.5 eq) in trifluoroacetic acid (5 mL) at 0° C. The reaction was brought to reflux for 20 h at which time the alkaline beta-naphthol test for diazonium salt was negative. Water (5 mL) was added to quench the reaction and the trifluoroacetic acid was removed in vacuo. The crude reaction mixture was diluted with 3N HCl (30 mL) and extracted with ethyl acetate (3×25 mL). Combined organic extracts were dried over anhydrous magnesium sulfate, filtered, and reduced to an oil. The reaction product was purified by flash chromatography over silica gel (35 mL, eluent; 10% ethyl acetate in hexane) to yield 540 mg (80%) of the title compound as a white solid. TLC analysis ($R_f$ 0.21, 10% ethyl acetate in hexane). MS (CI, CH4) m/z 301 (M+1,100), 303 (42), 329 (M+29,10), 269 (31), 241 (56)

b. 2-Chloro-7-hydroxy-9,10-dihydro-9,10-methano-9-anthracenecarboxylic acid

Using a procedure similar to that described in example 35e except starting with methyl 2-chloro-7-hydroxy-9,10- dihydro-9,10-methano-9-anthracenecarboxylate (described in example 90a), the title compound was formed in 87% yield as a white solid. TLC analysis (R$_f$ 0.15, 20% ethyl acetate in hexane). No additional characterization was necessary prior to the coupling reaction.

c. 1-(2-Chloro-7-hydroxy-9,10-dihydro-9,10-methanoanthracen-9-ylcarbonyl)-4-(3-pyridyl)piperidin-4-ol Using a procedure similar to that described in example 87a except starting with the 2-chloro-7-hydroxy-9,10-dihydro-9,10-methano-9-anthracenecarboxylic acid (described in example 90b), the title compound was formed in 37% yield as an off-white foam. TLC analysis (R$_f$ 0.18, 5% methanol in ether). MS (CI, CH4) m/z 447 (M+1,100), 449 (38), 475 (M+29,25), 429 (35)

EXAMPLE 91

1-(2-Chloro-7-methoxy-9,10-dihydro-9,10-methanoanthracen-9-ylmethyl)-4-(3-pyridyl)piperidin-4-ol Using a procedure similar to that described in example 87 except starting with 1-(2-chloro-7-methoxy-9,10-dihydro-9,10-methanoanthracen-9-ylcarbonyl)-4-(3-pyridyl)piperidin-4-ol, the title compound was formed in 68% yield as a white solid, mp 249°–253° C. (dec). TLC analysis of free base (R$_f$ 0.18, ethyl acetate). free base: 1H NMR (CDCl$_3$, 300 MHz) 8.75 (br s, 1H), 8.48 (d, J=2.4 Hz, 1H), 7.81 (d, J=8.1 Hz, 1H), 7.27 (m, 1H), 7.14 (m, 3H), 6.89 (dd, J=1.8, 7.8 Hz, 1H), 6.81 (d, J=2.3 Hz, 1H), 6.43 (dd, J=2.3, 7.9 Hz, 1H), 4.21 (br s, 1H), 3.74 (s, 3H), 3.41 (s, 2H), 2.89 (m, 2H), 2.74 (m, 2H), 2.60 (br s, 2H), 2.12 (m, 2H), 1.75 (m, 2H) MS (CI, CH4) m/z 447 (M+1,100), 475 (M+29,22), 429 (23), 191 (9) hydrochloride salt:

Analysis for C$_{27}$H$_{27}$ClN$_2$O$_2$.2HCl.0.5H$_2$O: Calculated: C, 61.31; H, 5.72; N, 5.29 Found: C, 60.91; H, 5.90; N, 4.92

The starting amide was prepared as follows:

a. Methyl 2-chloro-7-methoxy-9,10-dihydro-9,10-methano-9-anthracenecarboxylate

To an ethanol solution of methyl 2-chloro-7-hydroxy-9,10-dihydro-9,10-methano-9-anthracenecarboxylate (described in example 90a) was added potassium carbonate and methyl iodide. The suspension was heated to reflux, cooled and diluted with diethyl ether, filtered to remove salts, and concentrated to a solid. The title compound was formed in 90% yield. TLC analysis (R$_f$ 0.40, 20% ethyl acetate in hexane). MS (CI, CH4) m/z 315 (M+1,100), 343 (M+29,13), 301 (38), 287 (9), 279 (14), 265 (6), 255 (42)

b. 2-Chloro-7-methoxy-9,10-dihydro-9,10-methano-9-anthracenecarboxylic acid

Using a procedure similar to that described in example 35e except starting with methyl 2-chloro-7-methoxy-9,10-dihydro-9,10-methano-9-anthracenecarboxylate (described in example 91a), the title compound was formed in quantitative yield. No additional characterization was necessary prior to the coupling reaction.

c. 1-(2-Chloro-7-methoxy-9,10-dihydro-9,10-methanoanthracen-9-ylcarbonyl)-4-(3-pyridyl)piperidin-4-ol and 1-(2,6-Dichloro-7-methoxy-9,10-dihydro-9,10-methanoanthracen-9-ylcarbonyl)-4-(3-pyridyl)piperidin-4-ol To a toluene solution (10 mL) of 2-chloro-7-methoxy-9,10-dihydro-9,10-methano-9-anthracenecarboxylic acid (described in example 91b) (1.15 g, 3.82 mmol) was added thionyl chloride (0.56 mL, 7.6 mmol, 2 eq). The reaction was heated to reflux for 1 h monitoring gas evolution with a mineral oil bubbler. The toluene was removed, replaced with fresh toluene and stripped to dryness. This procedure was repeated two times. The residue was dissolved in tetrahydrofuran (10 mL). To that solution was added triethylamine (0.53 mL, 3.8 mmol, 1 eq) and 4-hydroxy-4-(3-pyridyl)piperidine (described in example 87e) (0.75 g, 4.2 mmol, 1.1 eq). The tetrahydrofuran solution was heated to reflux for 18 h, cooled to room temperature and poured into diethyl ether (100 mL). The organic phase was washed with 2.5N NaOH (3×25 mL) and saturated brine (25 mL), dried over anhydrous magnesium sulfate, filtered, and reduced to an oil. The reaction product was purified by flash chromatography over silica gel (60 mL, eluent: ethyl acetate) to yield 1.00 g of a white solid. TLC analysis (R$_f$ 0.20, ethyl acetate). The solid consisted of an inseparable mixture of the desired amide (23% overall) and the 2,6-dichloro-7-methoxy methanoanthracene amide (36% overall). No additional characterization of the mixture was undertaken as the reduced products were separable by flash chromatography.

EXAMPLE 92

1-(9,10-Dihydro-9,10-methanoanthracen-9-ylmethyl)-4-(2-ethylsulfinyl-3-pyridyl)piperidin-4-ol To a cooled solution (0 C.) of 1-(9,10-dihydro-9,10-methanoanthracen-9-ylmethyl)-4-(2-ethylthio-3-pyridyl)piperidin-4-ol (described in example 60) (0.500 g, 1.13 mmol) in acetic acid/water (22 mL/5 mL) was added an aqueous potassium permanganate (0.179 g, 1.13 mmol, 1.0 eq based on manganese) solution (8 mL of water) in a dropwise manner. The reaction was monitored by TLC or HPLC (reverse phase methanol/water, C18 column) for the appearance of over oxidation of the substrate to the sulfone. Sulfone began to form after 6 mL of the oxidation solution had been added. The oxidation is complete almost immediately. The reaction was quenched with saturated aqueous sodium bisulfite (50 mL) and basified with aqueous sodium hydroxide. The aqueous phase was extracted with ethyl acetate (3×100 mL). Combined organic extracts were dried over anhydrous sodium sulfate, filtered and reduced. The product was purified by flash chromatography over silica gel (60 mL, eluent: 15% methanol/ethyl acetate) to yield 260 mg (50%) of the title compound as a white solid. Nonpolar components of the chromatography were resubmited to fresh silica gel (60 mL, eluent: 80% diethyl ether/hexane) to isolate 170 mg (37%) of the corresponding sulfone (example 98). TLC analysis (sulfoxide: Rf 0.24, sulfone Rf 0.73, eluent: 15% methanol/ethyl acetate). Both free bases were dissolved in methylene chloride, acidified with ethereal HCl and diluted with ether. The resulting hydrochloride salts were filtered, rinsed with fresh ether, and dried in vacuo (55 C., 10 pascal, 18 h) to yield white solids, mp sulfoxide 214–216 C. (dec), sulfone 225–228 C. (dec). hydrochloride salt: 1H NMR (d6-DHSO, 300 MHz) 10.19 (br s, 1H), 8.69 (d, J=4.4 Hz, 1H), 7.63 (br d, J=7.9 Hz, 1H), 7.57 (m, 1H), 7.37 (m, 4H), 7.00 (m, 4H), 4.44 (m, 3H), 3.58 (m, 4H), 3.11 (m, 1H), 2.86 (m, 1H), 2.76 (br s, 2H), 2.30 (br m, 2H), 1.97 (br m, 2H), 1.18 (t, J=7.5 Hz, 3H) MS (CI, CH4) m/z 459 (M+1,100), 487 (M+29,16), 441 (21), 413 (12)

Analysis for C$_{28}$H$_{30}$N$_2$O$_2$S.2HCl.0.75 H2O Calculated: C, 61.70; H, 6.19; N, 5.14 Found: C, 61.48; H, 6.07; N, 5.07

EXAMPLE 93

1-(9,10-Dihydro-9,10-methanoanthracen-9-ylmethyl)-4-(2-ethylsulfonyl-3-pyridyl)piperidin-4-ol Using the procedure described in example 97, the title compound was isolated as a hydrochloride salt, mp 225–228

C. (dec). 1H NMR (d6-DMSO, 250 MHz) 8.62 (br d, J=3.5 Hz, 1H), 8.04 (br d, J=7.2 Hz, 1H), 7.72 (d of d, J=4.5, 8.1 Hz, 1H), 7.35 (m, 4H), 6.99 (m, 4H), 4.43 (m, 3H), 3.61 (q, J=7.2 Hz, 2H), 3.45–3.90 (m, 6H), 2.74 (m, 2H), 2.26 (m, 2H), 1.21 (t, J=7.3 Hz, 3H) MS (CI, CH4) m/z 475 (M+1, 100), 503 (M+29,3), 79 (83)

Analysis for $C_{28}H_{30}N_2O_3S.1.75$ HCl Calculated: C, 62.46; H, 5.94; N, 5.20 Found: C, 62.30; H, 5.75; N, 5.02

EXAMPLE 94

1-(2-Chloro-9,10-dihydro-9,10-methanoanthracen-9-ylmethyl)-4-(2-fluoro-3-pyridyl)piperidin-4-ol Using a procedure similar to that described in example 58 except starting with 1-(2-chloro-9,10-dihydro-9,10-methanoanthracen-9-ylmethyl)-4-piperidinone (described in example 1m), the title compound was obtained in 64% yield as a white solid, mp 199–203 C. (dec). hydrochloride: 1H NNR (CDCl$_3$, 300 MHz) 8.12 (m, 1H), 7.89 (m, 1H), 7.15–7.30 (m, 5H), 6.96 (m, 4H), 4.36 (s, 1H), 4.16 (br s, 2H), 3.50–3.70 (br m, 4H), 3.04 (br s, 3H), 2.17 (br m, 2H) MS (CI, CH4) m/z 435 (M+1,100), 463 (M+29,25), 417 (22), 354 (10)

Analysis for $C_{26}H_{24}ClFN_2O.1.5$ HCl Calculated: C, 63.78; H, 5.25; N, 5.72 Found: C, 63.79; H, 5.38; N, 5.58

EXAMPLE 95

1-(2-Chloro-9,10-dihydro-9,10-methanoanthracen-9-ylmethyl)-4-(2-ethylthio-3-pyridyl)piperidin-4-ol Using a procedure similar to that described in example 60 except starting with 1-(2-chloro-9,10-dihydro-9,10-methanoanthracen-9-ylmethyl)-4-(2-fluoro-3-pyridyl) piperidin-4-ol (described in example 99), the title compound was obtained in 93% yield as a white solid, mp 205–209 C. (dec). hydrochloride: 1H NMR (CDCl$_3$, 300 MHz) 8.40 (br s, 1H), 8.02 (br s, 1H), 6.9–7.35 (m, 8H), 4.38 (s, 1H), 4.14 (br s, 2H), 3.45–3.7 (m, 4H), 3.35 (br s, 2H), 3.05 (br s, 4H), 2.56 (m, 2H), 1.32 (br t, 3H) MS (CI, CH4) m/z 477 (M+1,100), 479 (40), 505 (M+29,20), 459 (17)

Analysis for $C_{28}H_{29}ClN_2OS.2.5$ HCl.H2O Calculated: C, 55.66; H, 5.92; N, 4.64 Found: C, 55.58; H, 5.30; N, 4.60

EXAMPLE 96

1-(9,10-Dihydro-9,10-methanoanthracen-9-ylmethyl)-4-(2-(1,1-dimethylethylthio)-3-pyridyl) piperidin-4-ol Using a procedure similar to that described in example 60 except starting with t-butylthiol, the title compound was obtained in 70% yield as a citrate salt, mp 135–140 C. (dec). citrate: 1H NMR (d6-DMSO, 300 MHz) 8.41 (d of d, J=1.6, 4.7 Hz, 1H), 7.68 (d of d, J=1.6, 8.0 Hz, 1H), 7.37 (m, 4H), 7.14 (d of d, J=4.7, 7.9 Hz, 1H), 7.05 (m, 4H), 4.65 (s, 1H), 4.48 (s, 4H), 3.60 (m, 5H), 2.74 (m, 6H), 2.34 (m, 4H), 1.56 (s, 9H) MS (CI, CH4) 471 (M+1,62), 415 (8), 193 (24), 175 (38), 147 (43), 113 (100)

Analysis for $C_{30}H_{34}N_2OS.C6H8O7.H2O$ Calculated: C, 63.50; H, 6.51; N, 4.11 Found: C, 63.24; H, 6.44; N, 3.86

EXAMPLE 97

1-(9,10-Dihydro-9,10-methanoanthracen-9-ylmethyl)-4-(2-methylthio-3-pyridyl)piperidin-4-ol Using a procedure similar to that described in example 60 except starting with methyl thiol, the title compound was obtained in 63% yield as a white hydrochloride salt, mp 320–324 C. (dec). hydrochloride: 1H NMR (CDCl3, 300 MHz) 8.40 (br s, 1H), 7.92 (br s, 1H), 7.1–7.4 (m, 5H), 6.98 (m, 4H), 4.39 (s, 1H), 4.17 (br s, 2H), 3.5–3.75 (m, 4H), 2.9–3.1 (m, 4H), 2.70 (s, 3H), 2.48 (m, 2H) MS (CI, CH4) m/z 429 (M+1,100), 457 (M+29,29), 411 (48)

Analysis for $C_{27}H_{28}N_2OS.2HCl.0.2$ H2O Calculated: C, 64.20; H, 6.06; N, 5.54 Found: C, 64.20; H, 6.04; N, 5.40

EXAMPLE 98

1-(9,10-Dihydro-9,10-methanoanthracen-9-ylmethyl)-4-(2-(2-N,N-dimethylaminoethylthio)-3-pyridyl)piperidin-4-ol Using a procedure similar to that described in example 60 except starting with 2-dimethylaminoethanthiol, the title compound was obtained in 58% yield as a white hydrochloride salt, mp 215–220 C. (dec). hydrochloride: 1H NMR (d6-DMSO, 300 MHz) 8.43 (d of d, J=1.4, 48 Hz, 1H), 7.65 (br d, J=6.5 Hz, 1H), 7.38 (m, 4H), 7.21 (d of d, J=4.7, 7.8 Hz, 1H), 7.02 (m, 4H), 4.50 (m, 2H), 3.30–3.74 (m, 9H), 2.88 (s, 4H), 2.76 (s, 1H), 2.31 (m, 2H) MS (CI, CH4) m/z 486 (M+1,100), 514 (M+29,11), 468 (10), 413 (7)

Analysis for $C_{30}H_{35}N_3OS.3HCl.1.25$ H2O Calculated: C, 58.34; H, 6.61; N, 6.80 Found: C, 58.19; H, 6.30; N, 6.54

EXAMPLE 99

4-(2-(4-Acetamidophenylthio)-3-pyridyl)-1-(9,10-dihydro-9,10-methanoanthracen-9-ylmethyl) piperidin-4-ol Using a procedure similar to that described in example 60 except starting with 4-acetamidothiophenol, the title compound was obtained in 26% yield as a white hydrochloride salt, mp 190–195 C. (dec). hydrochloride: 1H NMR (d6-DMSO, 300 MHz) 8.25 (d of d, J=1.4, 3.6 Hz, 1H), 7.81 (br d, J=6.8 Hz, 1H), 7.68 (d, J=8.6 Hz, 2H), 7.35–7.5 (m, 6H), 7.26 (d of d, J=4.9, 7.9 Hz, 1H), 7.02 (m, 4H), 4.51 (m 3H), 3.69 (m, 5H), 2.77 (br s, 2H), 2.35–2.6 (m, 4H), 2.09 (s, 3H) MS (CI, CH4) m/z 548 (M+1,100), 576 (M+29,13), 530 (13), 239 (6)

Analysis for $C_{34}H_{33}N_3O_2S.2$ HCl.1.5 H2O Calculated: C, 63.05; H, 5.91; N, 6.49 Found: C, 63.10; H, 5.59; N, 6.37

EXAMPLE 100

1-((9S,10S)-2-Chloro-9,10-dihydro-9,10-methanoanthracen-9-ylmethyl)-4-(1,1-dimethylethyl)piperidin-4-ol Using a procedure similar to that described in example 49 except starting with 1-((9S,10S)-2-chloro-9,10-dihydro-9,10-methanoanthracen-9-ylmethyl)-4-piperidinone (described in example 1m, optically active acid preparation described in example 1n), the title compound was obtained in 29% yield as a white hydrochloride salt, mp 291–293 C. hydrochloride: 1H NMR (CDCl$_3$, 300 MHz) 6.9–7.3 (m, 7H), 4.35 (s, 1H), 4.05 (br s, 2H), 3.39 (m, 4H), 3.07 (br s, 2H), 2.71 (m, 2H), 1.71 (m, 2H), 1.42 (s, 1H), 0.98 (s, 9H) MS (CI, CH4) m/z 396 (M+1,100), 398 (43), 424 (M+29, 24), 380 (26), 378 (54), 360 (10), (11)

Analysis for $C_{25}H_{30}ClNO.HCl.0.3$ H2O Calculated: C, 68.58; H, 7.27; N, 3.20 Found: C, 68.52; H, 7.02; N, 3.14

EXAMPLE 101

1-(9,10-Dihydro-9,10-methano-2-methoxyanthracen-9-ylmethyl)-4-(3-pyridyl)piperidin-4-ol Using a procedure similar to that described in example 87 except starting with 1-(9,10-dihydro-9,10-methano-2- methoxyanthracen-9-ylcarbonyl)-4-(3-pyridyl)piperidin-4-ol (described below), the title compound was formed in 66% yield as a white hydrochloride salt, mp 243–246 C. (dec). hydrochloride: 1H NMR (CDCl3, 300 MHz) 9.37 (m, 1H), 8.95 (m, 1H), 8.60 (m, 1H), 7.97 (m, 1H), 6.85–7.3 (m, 6H), 6.45 (d, J=7.6 Hz, 1H), 4.34 (s, 1H), 3.9–4.3 (m, 4H), 3.58 (m, 2H), 3.33 (m, 2H), 3.01 (m, 2H), rest of the resonances are buried in the baseline, not readily identifiable MS (CI, CH4) m/z 413 (M+1,100), 441 (M+29,16), 395 (28)

Analysis for $C_{27}H_{28}N_2O_2.2.4H_2O.1.8H_2O$ Calculated: C, 60.90; H, 6.43; N, 5.26 Found: C, 60.84; H, 5.95; N, 5.15

The starting amide was prepared as follows:

a. 9,10-Dihydro-9,10-methano-2-methoxyanthracenecarboxylic acid

Using a procedure similar to that described in example 108 except starting with 2-chloro-9,10-dihydro-9,10-methano-7-methoxyanthracene carboxylic acid (described in example 91b), the title compound was formed in 65% yield as a white solid. The product was characterized only by mass spectrometry. MS (CI, CH4) m/z 267 (M+1,100), 284 (M+29,50), 249 (9), 221 (11)

b. 1-(9,10-Dihydro-9,10-methano-2-methoxyanthracen-9-ylcarbonyl)-4-(3-pyridyl)piperidin-4-ol Using a procedure similar to that described in example 87a except starting with 9,10-dihydro-9,10-methano-2-methoxyanthracenecarboxylic acid (described in example 101a), the title compound was formed in 23% yield as an oil. TLC analysis (Rf 0.17, eluent: ethyl acetate) 1H NMR 8.77 (br s, 1H), 8.55 (d, J=4.3 Hz, 1H), 7.81 (m, 1H), 6.95–7.4 (m, 7H), 6.46 (m, 1H), 4.87 (m, 1H), 4.25 (s, 1H), 3.90 (m, 1H), 3.37 (m, 2H), 2.87 (m, 2H), rest of the resonances are buried in the baseline, not readily identifiable MS (CI, CH4) m/z 427 (M+1,100), 455 (M+29,22), 409 (17)

EXAMPLE 102—METHOD A (−)-1-(9,10-Dihydro-9,10-methanoanthracen-9-ylmethyl)-4-(2-ethylsulfinyl-3-pyridyl)piperidin-4-ol (titanium/tartrate/hydroperoxide based oxidation)

To a cooled solution (−20° C.) of (−)-diethyl D-tartrate (18.55 g. 90.5 mmol) in dry toluene (425 mL) under a nitrogen atmosphere was added titanium tetraisopropoxide (14.47 mL, 45.25 mmol) in a dropwise fashion. After stirring for five minutes, solid 1-(9,10-dihydro-9,10-methanoanthracen-9-ylmethyl)-4-(2-ethylthio-3-pyridyl)piperidin-4-ol (20.0 g, 45.25 mmol) was added in one portion. The solution was maintained at −20° C. for 25 minutes and cooled to −78° C. (dry ice/acetone) prior to the addition of freshly dried t-butyl hydroperoxide (90%, 5.28 mL, 47.5 mmol) in a dropwise fashion via syringe. The flask was allowed to warm to −15° C. over three hours, stirring was discontinued and the reaction vessel was placed in a −15° C. freezer for 18 hours. The reaction was quenched by the addition of aqueous sodium hydroxide (1.0N, 400 mL). The suspension was diluted with methylene chloride (500 mL) and the resulting mixture was filtered through diatomaceous earth, rinsing with additional methylene chloride. The organic layer was separated. The aqueous phase was extracted with methylene chloride (2×200 mL). Combined organic extracts were dried over anhydrous sodium sulfate, filtered and reduced.

The product was preabsorbed onto silica gel in preparation for purification by flash chromatography over silica gel (1000 mL, eluent: 20% methanol/ethyl acetate ramped to 30% as the desired compound elutes) to yield 17.63 g (85 %) of the title compound as a yellow/white solid. TLC analysis (sulfoxide: Rf 0.24, sulfone/sulfide Rf 0.73, eluent: 15% methanol/ethyl acetate). The enantiomeric purity of this compound was determined to be 1:3.7 ((+):(−)) by HPLC analysis (Ultron ES-OVM 6.0×15 cm, mobile phase 80% 0.01M pH 7.0 phosphate buffer/20% acetonitrile, flow rate: 1.0 mL/min, maximum 10 uL injection at 2.0 mg/ml; retention time: isomer 1 13.4 min, isomer 2 15.7 min). The solid material was dissolved in hot toluene and cooled to room temperature and seeded with several crystals of racemic sulfoxide. The racemate crystallizes slowly over 72 hours. The solid was removed by filtration, recovering 11.73 g of sulfoxide as an oil at the 5:95 purity level (isomer (+)/(−) ratio as determined by HPLC). This oil was dissolved in hot toluene and allowed to crystallize for an additional 24 hours. The oil (7.7 g) was dissolved in toluene at room temperature, filtered and seeded with crystals of pure isomer (−). After 4 hours at room temperature, the crystallization vessel was placed in the freezer at −15° C. overnight. The resulting solid slurry is diluted with cold toluene (0° C., 15 mL) and filtered. The white solid was dried at high vacuum to remove remaining solvent. This procedure formed pure isomer (−) (6.9 g, 33.3 yield of a high purity state by HPLC analysis, mp 185–186 C. (racemate: 206–208 C.), specific rotation [a] −106 (c=1.0, MeOH) degrees per gram per mL per dm ((+)-isomer specific rotation average +117, c=1.0, MeOH).

The free base was dissolved in methylene chloride, acidified with ethereal HCl and diluted with ether. The resulting hydrochloride salts were filtered, rinsed with fresh ether, and dried in vacuo (55° C., 10 pascal, 18 h) to yield off-white solids, mp sulfoxide 213°–216° C. (dec). hydrochloride salt: 1H NMR (d6-DMSO, 300 MHz) 10.19 (br s, 1H), 8.69 (d, J=4.4 Hz, 1H), 7.63 (br d, J=7.9 Hz, 1H), 7.57 (m, 1H), 7.37 (m, 4H), 7.00 (m, 4H), 4.44 (m, 3H), 3.58 (m, 4H), 3.11 (m, 1H), 2.86 (m, 1H), 2.76 (br s, 2H), 2.30 (br m, 2H), 1.97 (br m, 2H), 1.18 (t, J=7.5 Hz, 3H) MS (CI, CH4) m/z 459 (M+1,100), 487 (M+29,16), 441 (21), 413 (12)

Analysis for $C_{28}H_{30}N_2O_2S.1.8HCl$ Calculated: C, 64.15; H, 6.11; N, 5.34 Found: C, 64.27; H, 6.46; N, 5.23

EXAMPLE 102—METHOD B (OXAZIRIDINE BASED OXIDATION)

To a cooled solution (−78° C.) of 1-(9,10-dihydro-9,10-methanoanthracen-9-ylmethyl)-4-(2-ethylthio-3-pyridyl)piperidin-4-ol (200 mg, 0.452 mmol) in dry chloroform (or toluene) (8 mL) under a nitrogen atmosphere was added (S)-(+)-camphorsulfonyl oxaziridine (104 mg, 0.452 mmol). The cooling bath was removed and the reaction slowly warmed to room temperature. Conversion was monitored by thin layer chromatography (TLC analysis: sulfoxide Rf 0.24, sulfone/sulfide Rf 0.73, eluent: 15% methanol/ethyl acetate). After several hours starting material was still evident and could not be oxidized by the addition of more oxidant. The reaction was quenched by the addition of aqueous sodium hydroxide (1.0N, 10 mL). The aqueous phase was extracted with methylene chloride (2×15 mL. Combined organic extracts were washed with water, dried over anhydrous sodium sulfate, filtered and reduced.

The product was purified by flash chromatography over silica gel (50 mL, eluent: 10% methanol/ethyl acetate) to yield 93 mg (45 %) of the title compound as a yellow/white solid. The enantiomeric purity of this compound was determined to be 1:5.6 ((+):(−)) by HPLC analysis. The (−)-isomer could be further enriched by the procedure described above.

The starting piperidin-4-ol was prepared as follows:

a. 9,10-Dihydro-9,10-methano-9-anthracenecarboxylic acid

To a cooled solution (0° C.) of 9-formyl-9,10-dihydro-9,10-methanoanthracene (literature preparation: M. Sunagawa, et al.; Chem. Pharm. Bull. Vol. 27 (1979) pp 1806–1812; U.S. Pat. No. 4,224,344 Sunagawa et al., Sumitomo, Ltd.; Sep. 23, 1980; U.S. Pat. No. 4,358,620 Sunagawa et al., Sumitomo, Ltd.; Nov. 9, 1982) (78.5 mmol) in acetone (260 mL) was added Jones reagent (24 mL; 27 g chromium trioxide, 23 mL water diluted up to 100 mL of reagent solution) in portions. The reagent was added until an orange color persists. The reaction, containing a significant amount of reduced chromium salts, was warmed to room temperature. The solvents were removed in vacuo and replaced with water (300 mL) and saturated with sodium chloride. The aqueous phase was extracted with ethyl acetate (3×300 mL). Combined organic extracts were extracted with 2.5N NaOH (3×400 mL). The basic aqueous extracts were acidified with 3N HCl, saturated with sodium chloride, and extracted with ethyl acetate (4×300 mL). Combined organic extracts were dried over anhydrous magnesium sulfate, filtered, and reduced to a white solid. The title compound was formed in 80% yield as a white solid. MS (Cl CH4) m/z 237 (M+1,100), 265 (m+29,10), 219 (22), 209 (15), 193 (20)

b. 1-(9,10-Dihydro-9,10-methanoanthracen-9-ylcarbonyl)piperidin-4-ol

To a solution of 9,10-dihydro-9,10-methano-9-anthracenecarboxylic acid (24.1 mmol) in toluene (70 mL) was added thionyl chloride (2.28 mL, 31.3 mmol, 1.3 eq). The reaction was heated to reflux monitoring gas evolution with a mineral oil bubbler. The system reached a steady state within 40 min at which time it was slightly cooled and 4-hydroxypiperidine (6.08 g, 60.3 mmol, 2.5 eq) was added portionwise. A significant amount of heat is evolved and the reaction became dark. The suspension was heated to reflux for 2 h, cooled to room temperature and stirred for 18 h. The reaction was diluted with ethyl acetate (200 mL) and washed with 3N HCl (2×100 mL), 2.5N NaOH (2×100 mL) and saturated brine (200 mL). The organic phase was dried over anhydrous magnesium sulfate, filtered, and reduced to an oil. The procedure yielded the title compound in quantitative yield as a viscous oil. TLC analysis ($R_f$ 0.54, 10% methanol in $CHCl_3$). MS (Cl, CH4) m/z 320 (M+1, 100), 348 (M+29, 22), 302 (16)

c. 1-(9,10-Dihydro-9,10-methanoanthracen-9-ylmethyl)piperidin-4-ol

To a cooled suspension (0° C.) of -(9,10-dihydro-9,10-methanoanthrancen-9-ylcarbonyl)piperidin-4-ol (described above) (19.6 mmol) in diethyl ether (200 mL) under nitrogen was added lithium aluminum hydride (1.49 g, 39.2 mmol, 8 eq of hydride) in portions. The suspension was stirred at 0° C. for 30 min and warmed to room temperature. After 18 h at room temperature, the excess reagent was carefully quenched with the following in sequence: water (1.5 mL), 2.5N NaOH (1.5 mL) and additional water (4.5 mL). The suspension was stirred vigorously until the aluminum salts became a granular white solid. The suspension was diluted with ethyl acetate (100 mL), dried with a small amount of anhydrous magnesium sulfate and filtered. The filter cake was rinsed thoroughly with ethyl acetate. The solvent was removed to yield the title compound as a white solid in 88% yield. TLC analysis ($R_f$ 0.54, 10% methanol in $CHCl_3$) MS (Cl, CH4) m/z 306 (M+1, 100), 334 (M+29,14), 288 (62), 114 (8)

d. 1-(9,10-Dihydro-9,10-methanoanthracen-9-ylmethyl)-4-piperidinone

To a cooled solution (−78° C.) of oxalyl chloride (3.06 mL, 35.1 mmol, 2 eq) in methylene chloride (100 mL) under nitrogen was added distilled dimethylsulfoxide (5.00 mL, 70.2 mmol, 4 eq). After 10 min 1-(9,10-dihydro-9,10-methanoanthrancen-9-ylmethyl) piperidin-4-ol (described above) (17.5 mmol) was added as a methylene chloride solution (10 mL). The reaction was stirred at −78° C. for 30 min prior to the addition of triethylamine (19.6 mL, 140 mmol, 8 eq). The cooling bath was removed and the reaction warmed to room temperature over 1.5 h. The reaction mixture was poured into 2.5N NaOH (100 mL) and the aqueous phase extracted with methylene chloride (3×100 mL). Combined organic extracts were dried over anhydrous magnesium sulfate, filtered, and reduced to an oil. The crude reaction mixture was purified by flash chromatography over silica gel (400 mL, eluent:20% ethyl acetate in hexane) to yield the title compound in 80% yield as a white solid. TLC analysis ($R_f$ 0.31, 2% methanol in methylene chloride). MS (Cl, CH4) m/z 304 (M+1, 100), 332 (M+29,21)

e. 1-(9,10-Dihydro-9,10-methanoanthracen-9-ylmethyl)-4-(2-fluoro-3-pyridyl)piperidin-4-ol To a cooled solution (−72° C.) of distilled diisopropylamine (7.86 mL, 56.1 mmol, 1.3 eq) in THF/hexane (57 mL/37 mL) under nitrogen was added n-butyllithium (2.5M in hexane, 23.8 mL, 59.4 mmol, 1.4 eq). The resulting solution was warmed to −20° C. to assure deprotonation and then recooled to −72° C. A THF solution (13 mL) of 2-fluoropyridine (4.50 mL, 53.5 mmol, 1.25 eq) was then added dropwise resulting in a yellow precipitate. The deprotonation reaction was warmed to −50° C. for 45 min and briefly allowed to reach −30° C. before being recooled to −72° C. To this solution was added a mixture of 1-(9,10-dihydro-9,10-methanoanthracen-9-ylmethyl)-4-piperidone (described in 1d above) (13.0 g, 42.9 mmol) and lithium bromide (7.45 g, 85.8 mmol, 2 eq) in THF (48 mL) in a dropwise fashion. In the course of the addition, the yellow precipitate dissolved. The reaction was warmed to −20° C. over 1.5 h and quenched with acetic acid (10 mL). The solution was diluted with water (400 mL), basified with 2.5N NaOH and extracted with ethyl acetate (3×300 mL). The combined organic extracts were dried over anhydrous sodium sulfate, filtered and reduced to a solid. The product was purified by recrystallization from ethyl acetate (3 crops) to yield 13.3 g (77%) of the title compound as a white solid. TLC analysis ($R_f$ 0.22, 30% ethyl acetate in hexane). 1H NMR ($CDCl_3$, 300 mHz) 8.09 (d, J=8.2 Hz, 1H), 7.91 (dd, J=8.2, 9.4 Hz, 1H), 7.21 (m, 5H), 6.94 (m, 4H), 4.27 (s, 1H), 3.48 (s, 2H), 2.91 (m, 2H), 2.74 (m, 2H), 2.62 (s, 2H), 2.26 (m, 2H), 1.78 (m, 2H) MS (Cl, CH4) m/z 401 (M+1, 100), 429 (M+29,15), 383 (21) The free base was dissolved in ether and acidified with ethereal HCl. The hydrochloride salt was filtered, washed with fresh ether and dried in vacuo (room temperature, 10 pascal, 18 h) to yield a white solid, mp 188°–191° C. (dec).

Analysis for $C_{26}H_{25}FN_2O \cdot HCl \cdot 0.4H_2O$: Calculated: C, 70.31; H, 6.08; N, 6.31 Found: C, 70.65; H, 6.12; N, 5.83 f. 1-(9,10-Dihydro-9,10-methanoanthracen-9-ylmethyl)-4-(2-ethylthio-3-pyridyl)piperidin-4-ol To a solution of the 1-(9,10-dihydro-9,10-methanoanthracen-9-ylmethyl)-4-(2-fluoro-3-pyridyl)piperidin-4-ol (described in e. above) (2.00 g, 5.00 mmol, 1 eq) in THF (50 mL) under nitrogen was added the sodium salt of ethanethiol (0.90 g, 10.7 mmol, 2.2 eq). The thiolate salt was prepared from ethanethiol and sodium hydride under standard conditions. The reaction was heated to reflux for 18 h and quenched by pouring into water (100 mL). The aqueous phase was extracted with diethyl ether (2×100 mL), dried over anhydrous sodium sulfate, filtered, and reduced to an oil. The reaction product was purified by flash chromatography over silica gel (200 mL, eluent: 50% ether in hexane) to yield 2.00 g (90%) of the title compound. TLC analysis ($R_f$ 0.29, 50% ether in hexane).

1HNMR (CDCl$_3$, 250 MHz) 8.35 (dd, J=1.6, 4.7 Hz, 1H), 7.58 (dd, J=1.7, 7.7 Hz, 1H), 7.22 (m, 4H), 6.95 (m, 5H), 4.27 (s, 1H), 3.58 (s, 1H), 3.48 (s, 2H), 3.28 (q, J=7.3 Hz, 2H), 2.89 (m, 2H), 2.80 (ddd, J=9.3, 14.9, 10.7 Hz, 2H) 2.62 (d, J=1.5 Hz, 2H), 2.12 (m, 4H), 1.35 (t, J=7.2 Hz, 3h) MS (CI, CH4) m/z 443 (M+1, 100), 471 (M+29,16), 425 (25) The free base was dissolved in ether and acidified with ethereal HCl. The hydrochloride salt was filtered, rinsed with fresh ether and dried in vacuo (room temperature, 10 pascal, 18 h) to yield a white solid, mp 176–179 (dec).

Analysis for C$_{28}$H$_{30}$N$_2$OS.2HCl.0.5H$_2$O: Calculated: C, 64.11; H, 6.34; N, 5.34 Found: C, 64.05; H, 6.32; N, 5.26

EXAMPLE 103

1-(9,10-Dihydro-9,10-methanoanthracen-9-ylmethyl)-4-(2-ethylthio-3-pyridyl)piperidin-4-ol Reduction Process for Producing Sulfides to Recycle in Example 102

Zinc dust (1.72 g, 26.2 mmol) was transferred under nitrogen to a dry 500 mL round bottom flask equipped with a nitrogen inlet, addition funnel, teflon coated magnetic stirbar and thermocouple. Distilled tetrahydrofuran (200 mL, from sodium/benzophenone ketyl) was added to the reaction vessel via cannula and the resulting suspension cooled to 0° C. with an ice bath. Titanium tetrachloride (1.44 mL, 13.1 mmol, recently distilled) was added to the vortex of the rapidly stirred zinc suspension to reduce splattering. The initially formed titanium tetrachloride-tetrahydrofuran complex (yellow) quickly dissipates as reaction with the zinc takes place. After stirring for 10 minutes, a tetrahydrofuran solution (50 mL) of the substrate, 1-(9,10-dihydro-9, 10-methanoanthracen-9-ylmethyl)-4-(2-ethylsulfinyl-3-pyridyl)piperidin-4-ol (1.50 g, 3.27 mmol) was added dropwise to the gray/blue titanium (II) suspension. Reaction was instantaneous with the formation of a titanium (III) suspension (purple/black). The cooling bath was removed, and the reaction was maintained at room temperature for two hours. The reaction was quenched by the addition of water (100 mL) and aqueous sodium hydroxide (2.5N, 100 mL). The aqueous phase was extracted with ethyl acetate (2×250 mL). Combined organic extracts were dried over anhydrous sodium sulfate, filtered and reduced to an oil. TLC analysis (Rf 0.29, 50% ether in hexane) indicated the presence of product only. The reaction product was purified by dissolving the residue in hot toluene (10 mL) and diluting it with hot hexane (20 mL). After brief heating to reflux, this solution was filtered and cooled to room temperature. After the sulfide crystallization appears to have peaked, the recrystallization system was cooled to 0° C. After several hours the solvent was removed and the solid was dried on high vacuum (room temperature, 10 pascal, 1 h). The procedure yielded 1.25 g (86.4%) of the title compound as a yellow solid which appeared analytically pure by NMR. 1H NMR (CDCl$_3$, 250 MHz) 8.35 (dd, J=1.6, 4.7 Hz, 1H), 7.58 (dd, J=1.7, 7.7 Hz, 1H), 7.22 (m, 4H), 6.95 (m 5H), 4.27 (s, 1H), 3.58 (s, 1H), 3.48 (s, 2H), 3.28 (q, J=7.3 Hz, 2H), 2.89 (m, 2H), 2.80 (ddd, J=9.3, 14.9, 10.7 Hz, 2H), 2.62 (d, J=1.5 Hz, 2H), 2.12 (m, 4H), 1.35 (t, J=7.2 Hz, 3H) MS (CI, CH4) m/z 443 (M+1,100), 471 (M+29,16), 425 (25)

EXAMPLE 104

The following illustrate representative pharmaceutical dosage forms containing a compound of formula I' selected from, for example, a pure form or substantially pure form of (–)-1-(9,10-Dihydro-9,10-methanoanthracen-9-ylmethyl)-4-(2-ethylsulfinyl-3-pyridyl)piperidin-4-ol. A tablet preparation may be composed of the above compound(s) (50.0 mg) for therapeutic or prophylactic use in humans and may also contain pharmaceutically acceptable excipients such as Mannitol, USP (223.75 mg); croscarmellose sodium (6.0 mg); maize starch (15.0 mg); hydroxypropylmethylcellulose (2.25 mg) and magnesium stearate (3.0 mg). A capsule formulation containing the above active ingredient (10 mg) for oral administration may contain pharmaceutically acceptable excipients such as mannitol, USP (488.5 mg); croscarmellose sodium (15.0 mg) and magnesium stearate (1.5 mg). A suitable oil formulation may also be prepared using, for example, the free base of the above compound and a 25% glycerine in water mixture. This can be used, for example, in gel caps or other suitable delivery means. The above formulations may be prepared by conventional means or methods known in the art. The above examples are considered to be non-limiting and other known and/or conventional pharmaceutically acceptable excipients or diluents may be added to the active ingredient(s) to form a pharmaceutical composition which is useful in the treatment of neurological disorders including treatment of psychoses in patients in need of treatment thereof. The present invention therefore relates to a pharmaceutical composition comprising an effective amount of the active compounds as described herein in admixture with known pharmaceutically acceptable carriers. The present invention further relates to a method for antagonizing the effects of dopamine receptor (D1 and D2) agonists or serotonin 5HT2 agonists by antagonizing the respective receptor sites comprising administering to a patient in need of treatment thereof, an antagonist amount of the compounds or compositions as described herein. The invention therefore also relates to a method of treating neurological disorders affected, acerbated or caused by excessive activation of D1, D2 or 5HT2 receptors comprising administering an antagonistic amount of a compound according to formula I'.

EXAMPLE 105

The following illustrate representative pharmaceutical dosage forms containing a compound of formula I or I', for example as illustrated in any of the previous Examples, (hereafter referred to as "compound X"), for therapeutic or prophylactic use in humans:

| (a) Tablet mg/tablet | |
| --- | --- |
| Compound X | 50.0 |
| Mannitol, USP | 223.75 |
| Croscarmellose sodium | 6.0 |
| Maize starch | 15.0 |
| Hydroxypropylmethylcellulose (HPMC), | 2.25 |
| Magnesium stearate | 3.0 |
| (b) Capsule | |
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating o#cellulose acetate phthalate. The (+)-1-(9,10-Dihydro-9,10-methanoanthracen-9ylmethyl)-4-

(2-ethylsulfinyl-3-pyridyl)piperidin-4-ol is useful as an intermediate in the above described recycling process to produce the (−) enantiomer.
FORMULAE
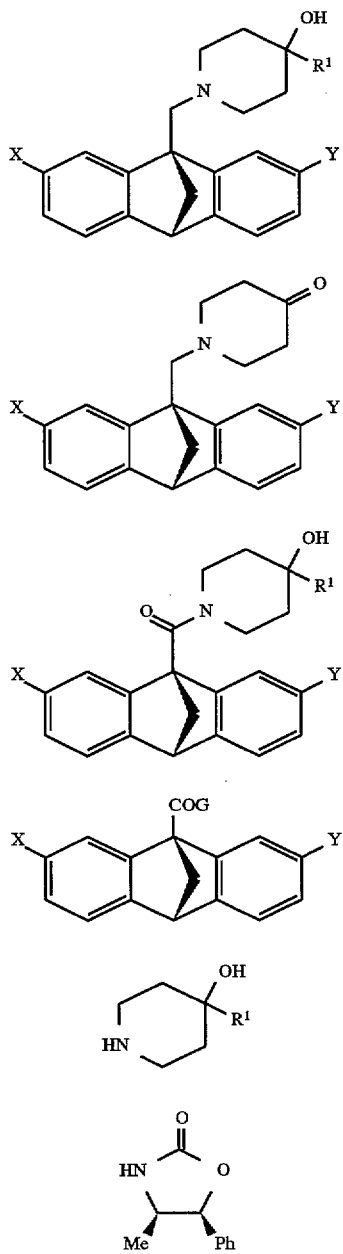
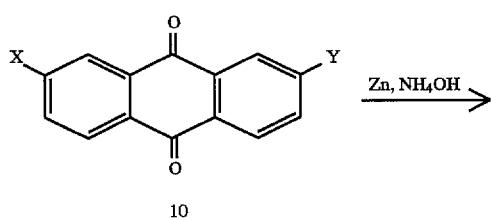
Scheme I
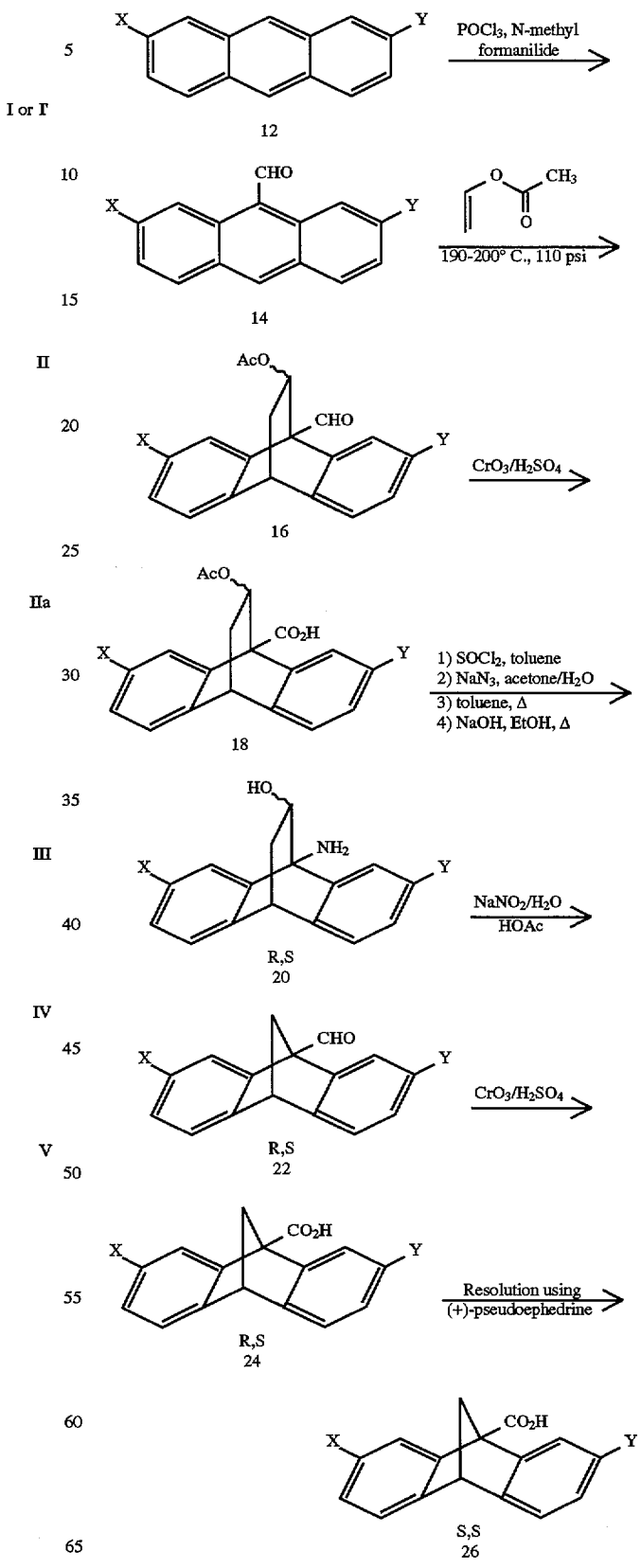

Scheme II
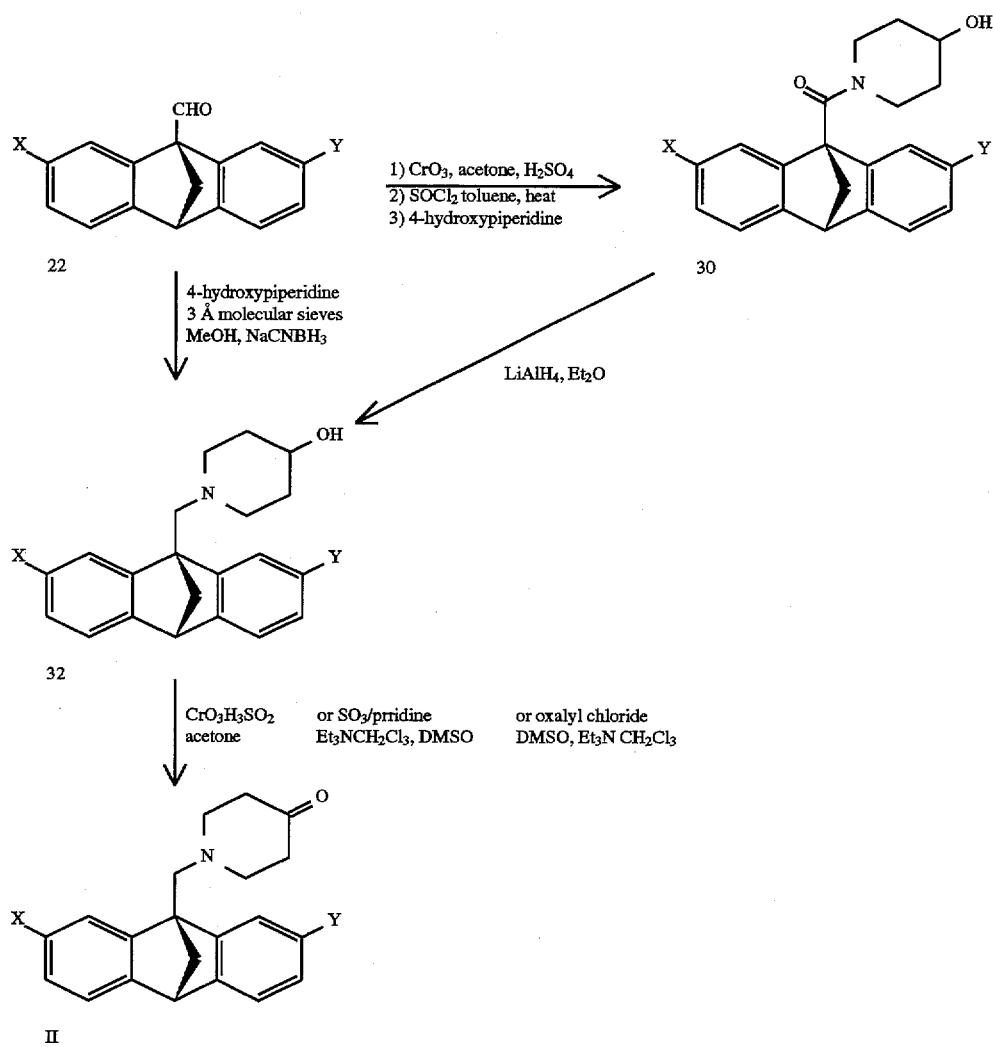
Scheme III
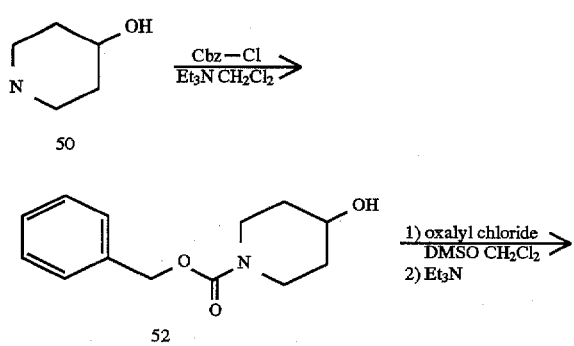

-continued
Scheme III
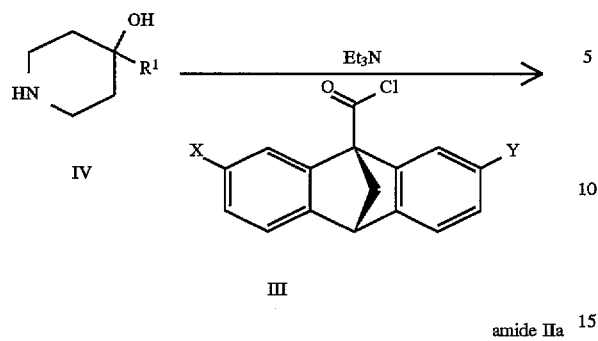
amide IIa
Scheme IV
Ethylsulfinyl: Specific Example
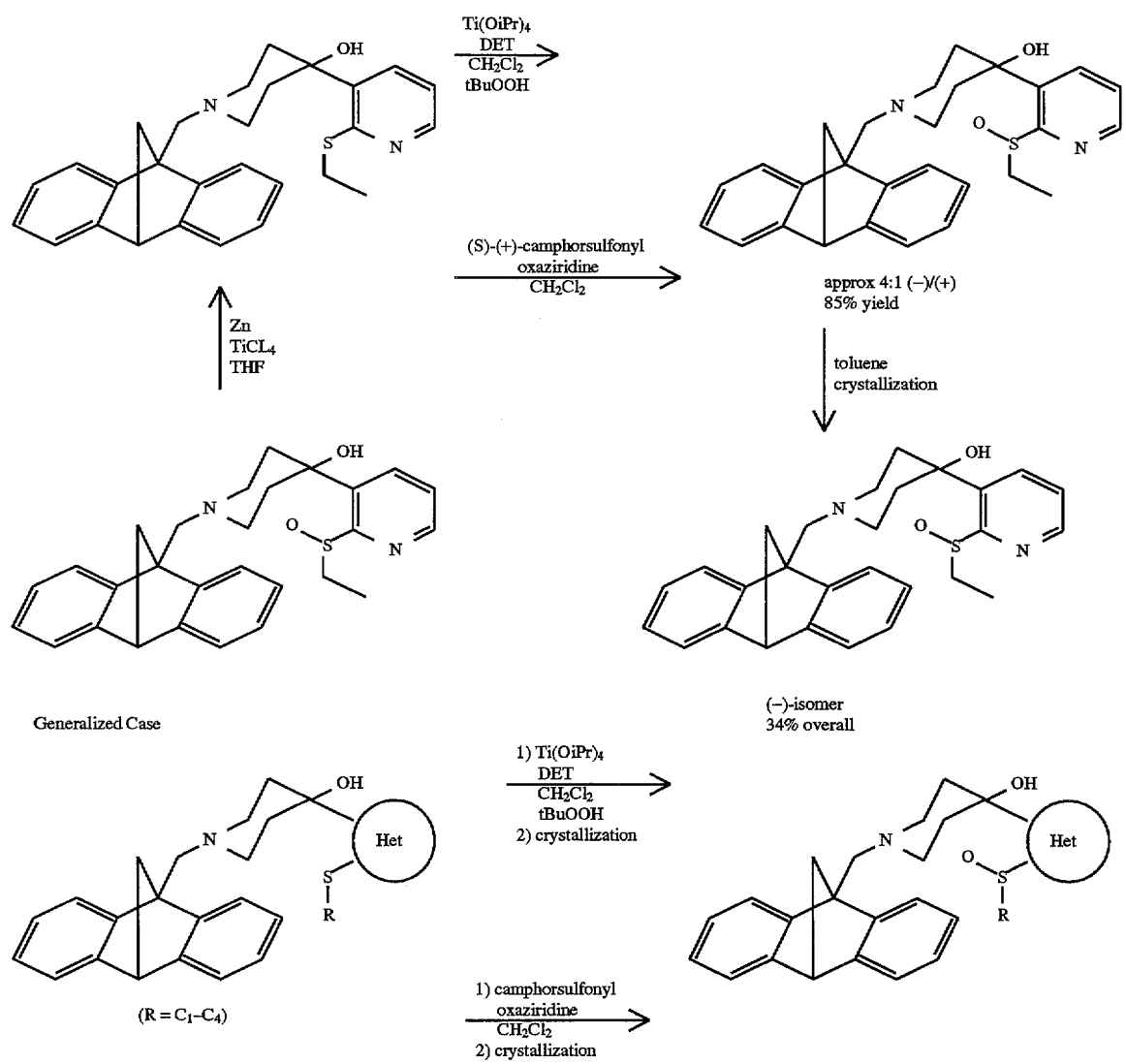

What is claimed is:

1. A compound of formula I

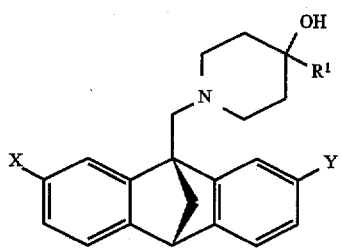

or a pharmaceutically acceptable salt thereof, wherein

X and Y are independently selected from hydrogen, halo, and (1–6C) (alkoxy; and $R^1$ is (1–6C)alkyl.

2. A compound as defined in claim 1, wherein X and Y are independently selected from hydrogen and halo.

3. A compound as defined in claim 2, wherein:

X and Y are independently selected from hydrogen and chloro; and $R^1$ is tert-butyl.

4. A compound as defined in claim 3, which is 1-((9S,10S)-2-Chloro-9,10-dihydro-9,10-methanoanthracen-9-yl-methyl)-4-(1,1-dimethylethyl)piperidin-4-ol.

5. A pharmaceutical composition comprising a compound of formula I,

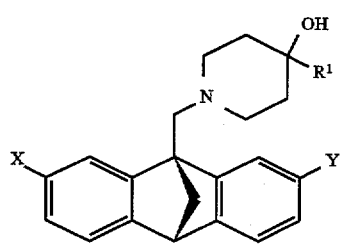

or a phramceutically acceptable salt thereof, wherein:

X and Y are indpendently selected from hydrogen, halo, and (1–6C)alkoxy; and $R^1$ is (1–6C)alkyl.

6. A composition as claimed in claim 5, wherein X and Y are independently selected from hydrogen and halo.

7. A composition as defined in claim 6, wherein:

X and Y are independently selected from hydrogen and chloro; and $R^1$ is tert-butyl.

8. A composition as defined in claim 7, wherein said compound is 1-((9S,10S)-2-Chloro-9,10-dihydro-9,10-methanoanthracen-9-yl-methyl)-4-(1,1-dimethylethyl)piperidin-4-ol.

9. A method of treating pyschoses, comprising administering to a mammal in need of such treatment an effective amount of a compound of formula I,

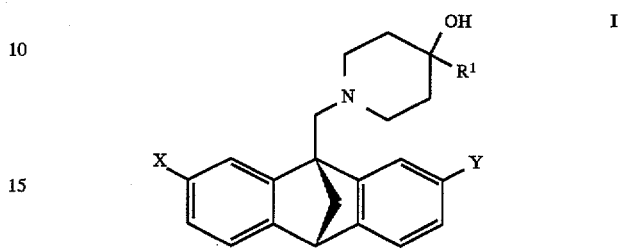

or a pharmaceutically acceptable salt thereof, wherein:

X and Y are independently selected from hydrogen, halo, and (1–6C)alkoxy; and $R^1$ is (1–6C)alkyl.

10. A method as defined in claim 9, wherein X and Y are independently selected from hydrogen and halo.

11. A method as defined in claim 10, wherein:

X and Y are independently selected from hydrogen and chloro; and $R^1$ is tert-butyl.

12. A method as defined in claim 11, wherein said compound is 1-((9S,10S)-2-Chloro-9,10-methanoanthracen-9-yl-methyl)4-(1,1-dimethylethyl)piperidin-4-ol.

13. A compound of the formula IIa,

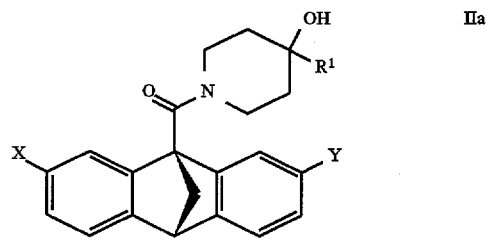

wherein X and Y are independently selected from hydrogen, halo, and (1–6C)alkoxy; and $R^1$ is (1–6C)alkyl.

* * * * *